(12) United States Patent
Schwartz et al.

(10) Patent No.: US 12,110,270 B2
(45) Date of Patent: Oct. 8, 2024

(54) SYSTEMS AND METHODS FOR GENERATION OF HYPERPOLARIZED MATERIALS

(71) Applicant: NVISION IMAGING TECHNOLOGIES GMBH, Ulm (DE)

(72) Inventors: Ilai Schwartz, Neu-Ulm (DE); Michael Keim, Neu-Ulm (DE); Stephan Knecht, Stuttgart (DE)

(73) Assignee: NVision Imaging Technologies GmbH, Ulm (DE)

( * ) Notice: Subject to any disclaimer, the term of this patent is extended or adjusted under 35 U.S.C. 154(b) by 0 days.

(21) Appl. No.: 18/473,243

(22) Filed: Sep. 23, 2023

(65) Prior Publication Data
US 2024/0018087 A1    Jan. 18, 2024

Related U.S. Application Data

(63) Continuation of application No. PCT/IB2022/000160, filed on Mar. 23, 2022.

(60) Provisional application No. 63/266,986, filed on Jan. 21, 2022, provisional application No. 63/260,631, filed on Aug. 27, 2021, provisional application No. 63/164,585, filed on Mar. 23, 2021.

(51) Int. Cl.
*C07C 69/732* (2006.01)
*C07B 59/00* (2006.01)
*C07C 67/40* (2006.01)

(52) U.S. Cl.
CPC .......... *C07C 69/732* (2013.01); *C07B 59/001* (2013.01); *C07C 67/40* (2013.01); *C07B 2200/05* (2013.01)

(58) Field of Classification Search
CPC .. C07C 69/732; C07B 59/001; C07B 2200/05
See application file for complete search history.

(56) References Cited

U.S. PATENT DOCUMENTS

| | | | |
|---|---|---|---|
| 8,961,933 B2* | 2/2015 | Reineri | A61K 49/10 424/9.1 |
| 9,034,928 B2* | 5/2015 | Millward | A61P 25/00 560/1 |

FOREIGN PATENT DOCUMENTS

DE        4417752 A1 *  11/1995   ........... C07C 69/732

OTHER PUBLICATIONS

D4417752 A1, Bayer AG, New and known alkyne derivs., English translation, 23 pages (Year: 1995).*
Breuning et al., Michael acceptor based antiplasmodial and antitrypanosomal cysteine protease inhibitors and unusual amino acids, Journal of Medicinal Chemistry, vol. 53, No. 5, pp. 1951-1963 (Year: 2010).*

(Continued)

*Primary Examiner* — Yate' K Cutliff
(74) *Attorney, Agent, or Firm* — Finnegan, Henderson, Farabow, Garrett & Dunner, LLP

(57) ABSTRACT

The present disclosure describes hyperpolarized materials for use in nuclear magnetic resonance, magnetic resonance imaging, or similar applications. The present disclosure describes methods for producing hyperpolarized materials for use in nuclear magnetic resonance, magnetic resonance imaging, or similar applications. The present disclosure describes precursor compounds for use in producing hyperpolarized materials for use in nuclear magnetic resonance, magnetic resonance imaging, or similar applications.

26 Claims, 22 Drawing Sheets

100

Provide a composition comprising a compound of Formula I.
110

↓

Hydrogenate a double bond or a triple bond in the compound of Formula I with parahydrogen to form a parahydrogenated derivative of the compound of Formula I, the parahydrogenated derivative having the structure of Formula II.
120

↓

Apply a polarization transferring waveform to transfer nuclear spin order from at least one H* in the compound of Formula II to any non-hydrogen nuclear spin in a biorelevant imaging agent, thereby forming a derivative of Formula II having a hyperpolarized biorelevant imaging agent.
130

(56) References Cited

OTHER PUBLICATIONS

Chukanov, N.V., et al., Synthesis of unsaturated precursors for parahydrogen-induced polarization and molecular imaging of 1-13C-acetates and 1-13C-pyruvates via side arm hydrogenation, American Chemical Society, Omega, 3, pp. 6673-6682 (Year: 2018).*

Reineri, F., et al., Hydrogenative-PHIP polarized metabolites for biological studies, Magnetic resonance Materials in Physical, Biology and Medicine, Feb. 2, 2021, 34:25-47 (Year: 2021).*

Barskiy, et al. "Rapid Catalyst Capture Enables Metal-Free para-Hydrogen-Based Hyperpolarized Contrast Agents", The Journal of Physical Chemistry. Letters, 2018, vol. 9, pp. 2721-2724.

Breuning et al. "Michael Acceptor Based Antiplasmodial and Antitrypanosomal Cysteine Protease Inhibitors with Unusual Amino Acids", Journal of Medicinal Chemistry, 2010, vol. 53, No. 5, pp. 1951-1963.

Chukanov et al. "Synthesis of Unsaturated Precursors for Parahydrogen-Induced Polarization and Molecular Imaging of 1-13 C-Acetates and 1-13C-Pyruvates via Side Arm Hydrogenation", ACS Omega, 2018, vol. 3, No. 6, pp. 6673-6682.

International Search Report and Written Opinion for International Application No. PCT/IB2022/000160, dated Nov. 7, 2022, 15 pages.

Kidd et al. "Facile Removal of Homogeneous SABRE Catalysts for Purifying Hyperpolarized Metronidazole, a Potential Hypoxia Sensor", The Journal of Physical Chemistry C, 2018, vol. 122, pp. 16848-16852.

Reineri et al. "Para-hydrogenated Glucose Derivatives as Potential 13C-Hyperpolarized Probes for Magnetic Resonance Imaging", Journal of The American Chemical Society, 2010, vol. 132, No. 20, pp. 7186-7193.

* cited by examiner

SYSTEMS AND METHODS FOR GENERATION OF HYPERPOLARIZED MATERIALS

CROSS-REFERENCES TO RELATED APPLICATIONS

This application is a continuation of international application no. PCT/IB2022/000160, filed Mar. 23, 2022, which designates the U.S. and claims priority to U.S. Provisional Patent Application No. 63/164,585, filed on Mar. 23, 2021, U.S. Provisional Patent Application No. 63/260,631, filed on Aug. 27, 2021, and U.S. Provisional Patent Application No. 63/266,986, filed on Jan. 21, 2022, each of which is incorporated herein by reference in its entirety for all purposes.

TECHNICAL FIELD

The disclosed embodiments generally relate to the generation of hyperpolarized materials for use in nuclear magnetic resonance, magnetic resonance imaging, or similar applications.

BACKGROUND

Parahydrogen induced polarization (PHIP) is a method for polarizing metabolites for hyperpolarized (HP) Magnetic Resonance Imaging (MRI), with low cost and high throughput. Parahydrogen induced polarization with side arm hydrogenation (PHIP-SAH) can be used to polarize metabolites, e.g., acetate molecules. However, existing PHIP-SAH polarization approaches may be unsuitable for preclinical or clinical HP MRI applications.

SUMMARY

In some embodiments, the present disclosure describes a composition comprising a compound of Formula (I):

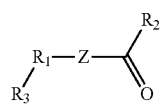

(I)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—); $R_1$ comprises a parahydrogen induced polarization (PHIP) transfer moiety; $R_2$ comprises an optionally substituted hydrocarbon, alkoxy group, primary amine, secondary amine, or tertiary amine; and $R_3$ comprises a biorelevant imaging agent comprising a non-hydrogen nuclear spin.

In some embodiments, the present disclosure describes a composition comprising a compound of Formula (II):

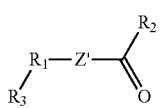

(II)

wherein Z' is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; wherein H* is a hydrogen having a spin order derived from parahydrogen; $R_1$ comprises a parahydrogen induced polarization (PHIP) transfer moiety; $R_2$ comprises an optionally substituted hydrocarbon, alkoxy group, primary amine, secondary amine, or tertiary amine; and $R_3$ comprises a biorelevant imaging agent comprising a non-hydrogen nuclear spin.

In some embodiments, the present disclosure describes a composition comprising: (i) biorelevant imaging agent comprising a non-hydrogen nuclear spin; and (ii) a compound of Formula (III):

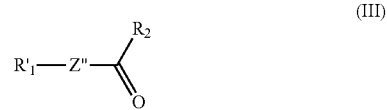

(III)

wherein Z" is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; $R_{1'}$ comprises a parahydrogen induced polarization (PHIP) transfer moiety; and $R_2$ comprises an optionally substituted hydrocarbon, alkoxy group, primary amine, secondary amine, or tertiary amine.

In some embodiments, the present disclosure describes a composition comprising: (i) hyperpolarized biorelevant imaging agent comprising a non-hydrogen nuclear spin; and (ii) a compound of Formula (IV):

(IV)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—); $R_{1'}$ comprises a parahydrogen induced polarization (PHIP) transfer moiety; $R_2$ comprises an optionally substituted hydrocarbon, alkoxy group, primary amine, secondary amine, or tertiary amine.

In some embodiments, the present disclosure describes compounds of Formula I, Formula II, Formula III, or Formula IV which comprise a PHIP transfer moiety. In some embodiments, the PHIP transfer moiety comprises an optionally substituted C1 hydrocarbon or an optionally substituted C2 hydrocarbon. In some embodiments, the PHIP transfer moiety comprises *CR$_4$R$_5$, *CR$_4$Y, *C=Y, or any deuterated version thereof, wherein: *C is a 12C or $^{13}$C carbon isotope; $R_4$ and $R_5$ are each independently selected from: $^1$H, $^2$H, $^3$H, a linear, branched, or cyclic C1-C10 alkyl hydrocarbon, a C6 aryl, a benzyl, a phenyl, a heteroaryl, and a haloalkyl group; and Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group. In some embodiments, the PHIP transfer moiety comprises *CR$_6$R$_7$—*CR$_8$R$_9$, or any deuterated version thereof, wherein: *C is a $^{12}$C or $^{13}$C carbon isotope; and R$_6$, R$_7$, R$_8$, and R$_9$ are each independently selected from: $^1$H, $^2$H, $^3$H, a linear, branched, or cyclic C1-C10 alkyl hydrocarbon, a C6 aryl, a benzyl, a phenyl, a heteroaryl, and a haloalkyl group. In some embodiments, the PHIP transfer moiety comprises *CH$_2$, *CH$_2$—*CH$_2$, *CHY, *C=Y, or any deuterated version thereof, wherein: *C is a $^{12}$C or $^{13}$C carbon isotope; and Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group. In some embodiments, the spin-1/2 atom is chosen from: $^1$H, $^{13}$C $^{15}$N, $^{19}$F, or $^{31}$P. In some embodiments, the PHIP transfer moiety includes at least one atom having a J-coupling with the non-hydrogen nuclear spin of at least 0.1 Hertz (Hz). In some embodiments, Z includes at least one atom having a J-coupling with the non-hydrogen nuclear spin of at least 0.1 Hertz (Hz).

In some embodiments, the present disclosure describes compounds of Formula I, Formula II, Formula III, or Formula IV in which R$_2$ comprises a solubilizing moiety. In some embodiments, R$_2$ comprises a hydrophobic and/or organophilic moiety. In some embodiments, R$_2$ comprises an organic solubilizing moiety. In some embodiments, R$_2$ comprises a hydrophilic and/or organophobic moiety. In some embodiments, R$_2$ comprises an optionally substituted hydrocarbon, alkoxy group, primary amine, secondary amine, or tertiary amine. In some embodiments, R$_2$ comprises, or is selected from: a methyl group, an ethyl group, a propyl group, an isopropyl group, an n-butyl group, an s-butyl group, a t-butyl group, an isobutyl group, a hydroxy group, a methyl alcohol group, an ethyl alcohol group, an n-propanol group, an isopropyl alcohol group a propionic alcohol group, an n-butyl alcohol group, an s-butyl alcohol group, a t-butyl alcohol group, an isobutyl alcohol group, a methoxy group, an ethoxy group, a propoxy group, an isopropxy, a propionic group, a butoxy group, a t-butoxy group, a s-butoxy group, an ester group, a phenyl group, a substituted phenyl group, a primary amine group, a secondary amine group, a tertiary amine group, a primary amide group, a secondary amide group, and a tertiary amide group.

In some embodiments, the present disclosure describes compounds of Formula I, Formula II, Formula III, or Formula IV which comprise a biorelevant imaging agent. In some embodiments, the biorelevant imaging agent comprises a compound of the formula R$_{10}$C(=O)X—; wherein R$_{10}$ is chosen from a linear, branched, or cyclic C1-C10 alkyl group, in which one or more C atoms are optionally replaced with C=C, CO, COH, CNH$_2$, COOH, CH$_2$COOH, CONH$_2$, OC(=O); and X is chosen from NR$_{11}$, S and O; wherein R$_1$ is selected from $^1$H, $^2$H, $^3$H and an amino protecting group, optionally selected from trifluoroacetyl, acetyl, benzoyl, carbobenzoxy, tert-butyl carbonate and benzyl. In some embodiments, the biorelevant imaging agent is selected from: pyruvate, glutamate, glutamine, lactate, acetate, acetoacetate, zymonate, alanine, fructose, fumarate, bicarbonate, urea, dehydroascorbate, alpha-ketoglutarate, dihydroxyacetone, glucose, ascorbate, and conjugate acids thereof. In some embodiments, the biorelevant imaging agent comprises pyruvate. In some embodiments, the biorelevant imaging agent comprises lactate. In some embodiments, the biorelevant imaging agent comprises alpha-ketoglutarate.

In some embodiments, composition of Formula I, Formula II, Formula III, or Formula IV has a solubility in water of less than 50 millimolar (mM). In some embodiments, composition of Formula I, Formula II, Formula III, or Formula IV has a solubility in an organic solvent (e.g., acetone, ethanol, chloroform, and toluene) of less than 50 millimolar (mM).

In some embodiments, composition reacting the composition of Formula I with parahydrogen results in a chemical yield of parahydrogenated product of at least 30%.

In some embodiments, the compositions of the present disclosure are for use in a parahydrogen induced polarization (PHIP) process.

In some embodiments, the present disclosure describes a method for preparing a hyperpolarized biorelevant imaging agent or a pharmaceutically acceptable salt thereof. In some embodiments, the method comprises: (a) providing a composition comprising a compound of Formula (I):

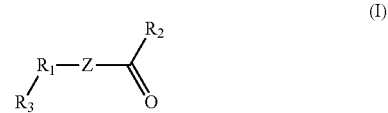

(I)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—); R$_1$ comprises a parahydrogen induced polarization (PHIP) transfer moiety; R$_2$ comprises an optionally substituted hydrocarbon, alkoxy group, primary amine, secondary amine, or tertiary amine; and R$_3$ comprises a biorelevant imaging agent comprising a non-hydrogen nuclear spin; (b) hydrogenating the double bond or the triple bond in the compound of Formula I with parahydrogen to form a parahydrogenated derivative of the compound of Formula I, the parahydrogenated derivative having the structure of Formula (II):

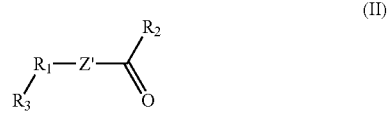

(II)

wherein Z' is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; wherein H* is a hydrogen having a spin order derived from parahydrogen; R$_1$ comprises a parahydrogen induced polarization (PHIP) transfer moiety; R$_2$ comprises an optionally substituted hydrocarbon, alkoxy group, primary amine, secondary amine, or tertiary amine; and $R_3$ comprises a biorelevant imaging agent comprising a non-hydrogen nuclear spin; and (c) applying a polarization transferring waveform to transfer nuclear spin order from at least one H* in the compound of Formula II to the non-hydrogen nuclear spin, thereby forming a derivative of Formula II having a hyperpolarized biorelevant imaging agent.

In some embodiments, the present disclosure describes a method for preparing a hyperpolarized biorelevant imaging agent or a pharmaceutically acceptable salt thereof, the method comprising: (a) providing a composition comprising a compound Formula (II):

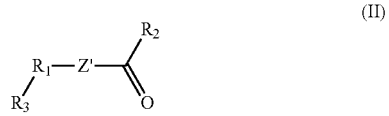

(II)

wherein Z' is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; wherein H* is a hydrogen having a spin order derived from parahydrogen; $R_1$ comprises a parahydrogen induced polarization (PHIP) transfer moiety; $R_2$ comprises an optionally substituted hydrocarbon, alkoxy group, primary amine, secondary amine, or tertiary amine; and $R_3$ comprises a biorelevant imaging agent comprising a non-hydrogen nuclear spin; and (b) applying a polarization transferring waveform to transfer nuclear spin order from at least one H* in the compound of Formula II to the non-hydrogen nuclear spin, thereby forming a derivative of Formula II having a hyperpolarized biorelevant imaging agent.

In some embodiments, the method further comprises hydrolyzing the derivative of Formula II to provide a composition comprising: (i) a hyperpolarized biorelevant imaging agent comprising a non-hydrogen nuclear spin; and (ii) a compound of Formula (III):

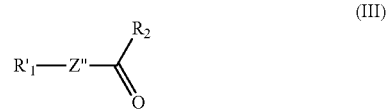

(III)

wherein Z" is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; $R_{1'}$ comprises a parahydrogen induced polarization (PHIP) transfer moiety; and $R_2$ comprises an optionally substituted hydrocarbon, alkoxy group, primary amine, secondary amine, or tertiary amine. In some embodiments, the method further comprises washing the hyperpolarized biorelevant imaging agent one or more times with an organic solvent. In some embodiments, the non-hydrogen nuclear spin has a non-hydrogen nuclear spin polarization above 10% after the washing step.

In some embodiments, the present disclosure describes a hyperpolarized biorelevant imaging agent or a pharmaceutically acceptable salt thereof, produced by a method of the present disclosure.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which comprise a part of this specification, illustrate several embodiments and, together with the description, serve to explain certain principles and features of the disclosed embodiments. In the drawings.

DETAILED DESCRIPTION

Figure 1:
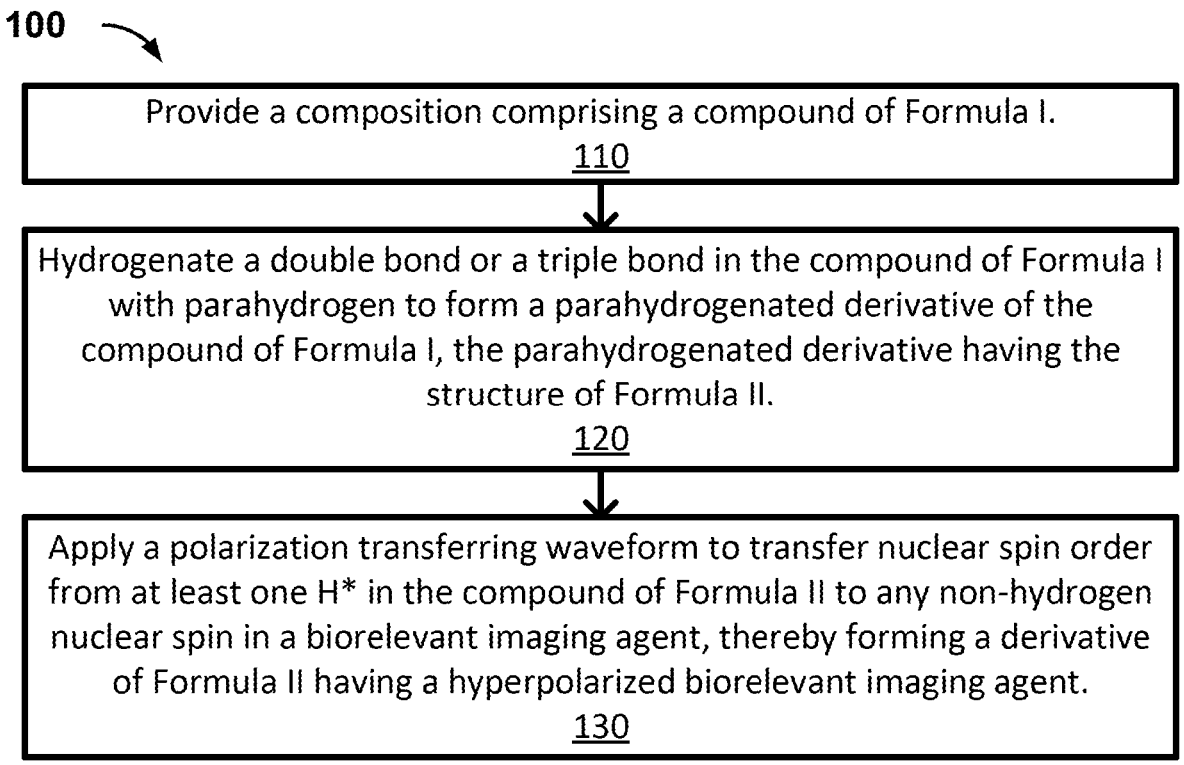
FIG. 1 depicts a first exemplary process for generating polarized biorelevant imaging agents, in accordance with various embodiments.

Reference will now be made in detail to exemplary embodiments, discussed with regards to the accompanying drawings. Unless otherwise defined, technical and/or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Recent work in the field of nuclear magnetic resonance (NMR) and magnetic resonance imaging (MRI) has demonstrated that NMR and MRI signals associated with a variety of biorelevant imaging agents can be enhanced by many orders of magnitude using a variety of so-called hyperpolarization techniques. This signal enhancement allows for improved spectroscopic analysis of the biorelevant imaging agent as it is metabolized by various tissues at different locations within a body. Analysis of the metabolic information determined by such spectroscopic imaging may allow for non-invasive determination of a health state of tissue within a body. For example, abnormal metabolism of a biorelevant imaging agent may be indicative of a disease such as cancer at some location in the body.

Existing techniques for hyperpolarizing biorelevant imaging agents include dissolution dynamic nuclear polarization (DNP), parahydrogen induced polarization (PHIP), PHIP-sidearm hydrogenation (PHIP-SAH), and signal amplification by reversible exchange (SABRE). In PHIP-SAH, a precursor of the biorelevant imaging agent is reacted with parahydrogen to form a parahydrogenated derivative of the precursor. Spin order is then transferred from the protons added via the parahydrogenation reaction to a nucleus of interest (such as a carbon-13 nucleus) contained within the biorelevant imaging agent. The parahydrogenated derivative of the precursor is cleaved (e.g., hydrolyzed) to yield the hyperpolarized biorelevant imaging agent. The biorelevant imaging agent is then purified and used in an NMR or MRI procedure. In some embodiments, the precursor can comprise a biorelevant imaging agent coupled to a sidearm containing at least one unsaturated bond (e.g., at least one carbon-carbon double bond or at least one carbon-carbon triple bond) suitable for reaction with parahydrogen. However, previous precursors have used sidearms that may not allow the generation of biorelevant imaging agents with clinically relevant polarizations, concentrations, volumes, or purities. Such behavior may be related to poor solubility of the precursors in organic solvents (where parahydrogen is highly soluble), poor yields in the reaction between the unsaturated bond and parahydrogen, or a variety of other factors. Accordingly, there is a need for new PHIP-SAH precursors that produce hyperpolarized biorelevant imaging agents with clinically relevant polarizations, concentrations, volumes, or purities.

The disclosed embodiments include systems and methods for producing biorelevant imaging agents, in clinically relevant polarizations concentrations, volumes and purity. Disclosed embodiments provide technical improvements in polarizing biorelevant imaging agents in solution. These technical improvements support increases in biorelevant imaging agent concentration and the degree of biorelevant polarization.

Hyperpolarization and Parahydrogen

As used in the present disclosure, hyperpolarization describes a condition in which an absolute value of a difference between a population of spin states (e.g., nuclear spin states, proton spin states, or the like) being in one state (e.g., spin up) and a population of a spin states being in another state (e.g., spin down) exceeds the absolute value of the corresponding difference at thermal equilibrium.

Parahydrogen can be used as a source of polarization, consistent with disclosed embodiments. Parahydrogen, as described herein, is a form of molecular hydrogen in which the two proton spins are in the singlet state. The disclosed embodiments are not limited to a particular method of generating parahydrogen. Parahydrogen may be formed in a gas form or in a liquid form. In some embodiments, parahydrogen is generated in gas form by flowing hydrogen gas at low temperature through a chamber with a catalyst (e.g., iron oxide or another suitable catalyst). The hydrogen gas can contain both parahydrogen and orthohydrogen. The low temperature can bring the hydrogen gas to thermodynamic equilibrium in the chamber, increasing the population of parahydrogen.

The disclosed embodiments are not limited to a particular parahydrogen generation location or use location. Parahydrogen can be generated at a first location and subsequently transported to a second location for use. In some embodiments, the first location is a chamber, which may be part of a container, bottle, holder or other regions capable of holding a gas or a liquid. Such a chamber may be maintained at a suitable pressure or temperature. In some embodiments, the first location is a physical location such as a room, a lab, a particular warehouse, hospital or other location where the parahydrogen is generated.

The disclosed embodiments are not limited to a particular parahydrogen transport method. The generated parahydrogen may be transported in a chamber, which may be different from the chamber where the parahydrogen was generated. The chamber transporting the parahydrogen gas may be maintained at a suitable pressure or temperature, which may be transported by vehicle or persons. Transporting the parahydrogen may involve moving the parahydrogen from one container to a different container. Transporting the parahydrogen may involve moving the parahydrogen within the same location, such as from one part of a room to another part of the room. Transporting the parahydrogen may involve moving the parahydrogen from one room in a building to a different room in the same building or to a nearby building. Transporting the parahydrogen may involve moving the parahydrogen to a different location in another part of the same city, or a different city. Transporting the parahydrogen may involve bringing the parahydrogen into the vicinity of a polarizer, an NMR device, or an MRI device. Transporting the parahydrogen may involve packaging or shipping the parahydrogen in suitable containers.

In some embodiments, a population difference between two spin states is the difference between the population of the two spin states divided by the total population of the two spin states. A population difference may be expressed as a fractional population difference or a percentage population difference. In some embodiments, the fractional population difference is at least about 0.1, 0.2, 0.3, 0.4, 0.5, 0.6, 0.7, 0.8, 0.9, or more, at most about 0.9, 0.8, 0.7, 0.6, 0.5, 0.4, 0.3, 0.2, 0.1, or less, or within a range defined by any two of the preceding values.

Hydrogen gas can exhibit a population difference between proton spin states which greatly exceeds the population difference between proton spin states at thermal equilibrium. Parahydrogen can have a large population difference between the singlet spin state and any of the triplet spin states. In the case of IzIIz2, there is a large population difference, for example, between the spin state $|\uparrow\rangle|\downarrow\rangle$ and the spin state $|\uparrow\rangle|\uparrow\rangle$. The population difference in proton spin states can be at least about 0.1 (e.g., a 10% difference in spin states-55% of the parahydrogen molecules in a sample being in the singlet state and 45% in the triplet state), 0.2, 0.3, 0.4, 0.5, 0.6, 0.7, 0.8, 0.9, or more, at most about 0.9, 0.8, 0.7, 0.6, 0.5, 0.4, 0.3, 0.2, 0.1, or less, or within a range defined by any two of the preceding values.

Biorelevant Imaging Agents

The disclosed embodiments include systems and methods for producing and utilizing biorelevant imaging agents with clinically relevant polarizations, concentrations, volumes, or purities. In some embodiments, the method is for preparing an NMR material. In some embodiments, the NMR material is suitable for use in NMR or MRI operations. In some embodiments, the NMR material increases NMR or MRI signal and signal-to-noise ratio (SNR). In some embodiments, the NMR material is suitable for use in solution NMR spectroscopy. In some embodiments, the NMR material is a chemical compound. In some embodiments, the NMR material is a metabolite (e.g., a molecule with a biological relevance such as an amino acid, a saccharide, a derivative thereof, or the like), such as a metabolite suitable for use in an NMR metabolomics application. In some embodiments, the NMR material is suitable for in-vitro probing of the metabolism of a cell culture or other biological tissue. In some embodiments, the NMR material is used in an NMR probe to investigate a transient effect in which high signal enhancement due to hyperpolarization is needed, such as proton exchange between water and biomolecules. In some embodiments, the NMR material is a small molecule or metabolite suitable for injection into a cell, tissue or organism for detection in an MRI scan. In some embodiments, the NMR material is introduced into a chamber for further analysis by NMR or MRI operations. In some embodiments, the NMR material is enriched with one or more deuterium ($^2$H) or carbon-13 ($^{13}$C) atoms.

Consistent with disclosed embodiments, NMR material can include biorelevant imaging agents. In some embodiments, the biorelevant imaging agent can be suitable for use in NMR or MRI operations. In some embodiments, the biorelevant imaging agent may increase NMR or MRI signal or signal-to-noise ratio (SNR). In some embodiments, the biorelevant imaging agent can be suitable for use in solution NMR spectroscopy. In some embodiments, the biorelevant imaging agent may be a metabolite (e.g., a molecule with a biological relevance such as an amino acid, a saccharide, a derivative thereof, or the like), such as a metabolite suitable for use in an NMR metabolomics application. In some embodiments the biorelevant imaging agent is used for perfusion imaging or contrast enhanced imaging in MRI scans. In some embodiments, the biorelevant imaging agent is suitable for in-vitro probing of the metabolism of a cell culture or other biological tissue. In some embodiments, the biorelevant imaging agent is used for in-vitro probing of the metabolism of a cell culture or other biological tissue. In some embodiments, the biorelevant imaging agent is used in an NMR probe to investigate a transient effect in which high signal enhancement due to hyperpolarization is needed, such as proton exchange between water and biomolecules. In some embodiments, the biorelevant imaging agent is a small molecule or metabolite suitable for injection into a cell, tissue or organism for detection in an MRI scan. In some embodiments, the biorelevant imaging agent is introduced into a chamber for further analysis by NMR or MRI operations. In some embodiments, the biorelevant imaging agent is enriched with one or more 2H or $^{13}$C atoms.

In some embodiments, the biorelevant imaging agent comprises pyruvate, lactate, alpha-ketoglutarate, bicarbonate, fumarate, urea, dehydroascorbate, glutamate, glutamine, acetate, dihydroxyacetone, acetoacetate, glucose, ascorbate, zymonate, alanine, fructose, imidazole, nicotinamide, nitroimidazole, pyrazinamide, isoniazid, a conjugate acid of any of the foregoing, natural and unnatural amino acids, esters thereof, or $^2$H, $^{13}$C, or nitrogen-15 ($^{15}$N) enriched versions of any of the foregoing. In some embodiments, the biorelevant imaging agent comprises pyruvate, lactate, alpha-ketoglutarate. In some embodiments, the biorelevant imaging agent comprises pyruvate. In some embodiments, the biorelevant imaging agent comprises lactate. In some embodiments, the biorelevant imaging agent comprises alpha-ketoglutarate (e.g., ethyl alpha-ketoglutarate).

In some embodiments, the biorelevant imaging agent comprises at least one non-hydrogen nuclear spin. In some embodiments, the non-hydrogen nuclear comprises at least one spin-1/2 atom. In some embodiments, the non-hydrogen nuclear spin comprises $^{13}$C or $^{15}$N. In some embodiments, the biorelevant imaging agent is at least partially isotopically labeled with the non-hydrogen nuclear spin. In some embodiments, the biorelevant imaging agent is at least partially enriched with the non-hydrogen nuclear spin when compared to an analog of the biorelevant imaging agent that features the non-hydrogen nuclear spin at its natural abundance. In some embodiments, the biorelevant imaging agent is enriched to feature the non-hydrogen nuclear spin at an abundance of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more, at most about 99%, 98%, 97%, 96%, 95%, 94%, 93%, 92%, 91%, 90%, 85%, 80%, 75%, 70%, 65%, 60%, 55%, 50%4, 45%, 40%, 35%, 30%, 25%, 20%, 15%, 10%, 9%, 8%, 7%, 6%, 5%, 4%, 3%, 2%, 1%, or less, or an abundance that is within a range defined by any two of the preceding values.

In some embodiments, the non-hydrogen nuclear spin replaces an NMR-inactive (i.e., spin-0) nucleus (e.g., $^{12}$C or a quadrupolar (i.e., spin>1/2) nucleus (e.g., nitrogen-14, $^{14}$N) of the analog of the biorelevant imaging agent that features the non-hydrogen nuclear spin at its natural abundance. For example, an analog of pyruvate that features $^{13}$C at its natural abundance may include about 98.9% $^{12}$C and about 1.1% $^{13}$C at either C* in the structure H$_3$C—C*(=O)—C*OOH. As a biorelevant imaging agent, pyruvate may instead be isotopically enriched with $^{13}$C such that one or both C* comprises $^{13}$C at any abundance described herein. As used herein, *C and C* describe a carbon that can be either a $^2$C or $^{13}$C carbon isotope. As another example, an analog of urea that features $^{15}$N at its natural abundance may include about 99.6% $^{14}$N and about 0.4% $^{15}$N at either N* in the structure H$_2$N*—C(=O)—*NH$_2$. As a biorelevant imaging agent, urea may instead be isotopically enriched with $^{15}$N such that one or both N* comprises $^5$N at any abundance described herein. As used herein, *N and N* describe a nitrogen that can be either a $^{14}$N or $^{15}$N nitrogen isotope.

Biorelevant Imaging Agent Precursors

In some embodiments, the present disclosure describes precursors (i.e., precursor compounds) which comprise a biorelevant imaging agent and a sidearm. In some embodiments, the biorelevant imaging agent is covalently attached to the sidearm. In some embodiments, the biorelevant imaging agent is attached to the sidearm through a transfer moiety, such as a PHIP transfer moiety, which is part of the sidearm. The sidearm can be parahydrogenated using parahydrogen (e.g., by mixing the precursor and the parahydrogen).

In some embodiments, the hydrogenation creates IzIIz2 order, the lower energy state between $|\uparrow\rangle|\downarrow\rangle$, $|\downarrow\rangle|\uparrow\rangle$ or singlet spin order on two hydrogens spins, depending on whether the hydrogenation is performed at a low magnetic field or high magnetic field.

In some embodiments, the precursor is chosen such that, following hydrogenation and other optional chemical reactions, the biorelevant imaging agent is suitable for use in hyperpolarized NMR or MRI applications. In some embodiments, additional chemical reactions following hydrogenation can be used to separate the biorelevant imaging agent from the precursor. Such additional chemical reactions may include cleaving the side arm of the precursor, e.g., by hydrolysis. For example, the biorelevant imaging agent can be a metabolite molecule, such that the precursor can a derivative of the metabolite molecule, with the derivative having the generic chemical structure of Formula I. The biorelevant imaging agent can be polarized using the PHIP-SAH method (i.e., parahydrogenation of the sidearm and subsequent polarization transfer to the biorelevant imaging agent). Following hydrogenation and polarization transfer, the linking bond in the precursor (e.g., ester bond) may be hydrolyzed to produce a polarized biorelevant imaging agent and a separate sidearm element.

As used herein, hydrolysis is defined as the cleavage of a molecule via a nucleophilic substitution reaction, with the addition of the elements of water. Hydrolysis can be also performed under anhydrous conditions in the presence of hydroxide ions.

Consistent with disclosed embodiments, precursors of the general chemical form presented in Formula I can be used as precursors for PHIP-SAH. Following hydrogenation of such precursors, the two $^1$H spins exhibiting the spin order are near (e.g., only three, four, or five bonds away) from the target carbon or nitrogen on the metabolite, which can be $^{13}C$ enriched or $^{15}N$ enriched as described herein. In some embodiments, a high J-coupling between the $^{13}C$ or $^{15}N$ spin and at least one of the $^{1}H$ spins derived from parahydrogen is achieved. In some embodiments, a J-coupling is achieved of at least about 0.1 hertz (Hz), 0.2 Hz, 0.3 Hz, 0.4 Hz, 0.5 Hz, 0.6 Hz, 0.7 Hz, 0.8 Hz, 0.9 Hz, 1 Hz, 2 Hz, 3 Hz, 4 Hz, 5 Hz, 6 Hz, 7 Hz, 8 Hz, 9 Hz, 10 Hz, or more, at most about 10 Hz, 9 Hz, 8 Hz, 7 Hz, 6 Hz, 5 Hz, 4 Hz, 3 Hz, 2 Hz, 1 Hz, 0.9 Hz, 0.8 Hz, 0.7 Hz, 0.6 Hz, 0.5 Hz, 0.4 Hz, 0.3 Hz, 0.2 Hz, 0.1 Hz, or less, or a J-coupling that is within a range defined by any two of the preceding values. For instance, in some embodiments, the J-coupling is between 1 Hz and 2 Hz, between 1 Hz and 3 Hz, between 1 Hz and 4 Hz, between 1 Hz and 5 Hz, between 1 Hz and 6 Hz, between 1 Hz and 7 Hz, between 1 Hz and 8 Hz, between 1 Hz and 9 Hz, between 1 Hz and 10 Hz, between 2 Hz and 3 Hz, between 2 Hz and 4 Hz, between 2 Hz and 5 Hz, between 2 Hz and 6 Hz, between 2 Hz and 7 Hz, between 2 Hz and 8 Hz, between 2 Hz and 9 Hz, between 2 Hz and 10 Hz, between 3 Hz and 4 Hz, between 3 Hz and 5 Hz, between 3 Hz and 6 Hz, between 3 Hz and 7 Hz, between 3 Hz and 8 Hz, between 3 Hz and 9 Hz, between 3 Hz and 10 Hz, between 4 Hz and 5 Hz, between 4 Hz and 6 Hz, between 4 Hz and 7 Hz, between 4 Hz and 8 Hz, between 4 Hz and 9 Hz, between 4 Hz and 10 Hz, between 5 Hz and 6 Hz, between 5 Hz and 7 Hz, between 5 Hz and 8 Hz, between 5 Hz and 9 Hz, between 5 Hz and 10 Hz, between 6 Hz and 7 Hz, between 6 Hz and 8 Hz, between 6 Hz and 9 Hz, between 6 Hz and 10 Hz, between 7 Hz and 8 Hz, between 7 Hz and 9 Hz, between 7 Hz and 10 Hz, between 8 Hz and 9 Hz, between 8 Hz and 10 Hz, or between 9 Hz and 10 Hz. Such a J-coupling may enable efficient polarization of the $^{13}C$ spin.

Disclosed herein are novel precursors, including the compounds of Formulas I, II, III, and IV, tautomers thereof, deuterated derivatives of those compounds and their tautomers, salts thereof, and $^{13}C$ or $^{15}N$ enriched derivatives at one or more sites within the molecule (which may be in turn subject to hyperpolarization), and the subsequent generation of precursors given by the general Formulas I, II, III, and IV.

Precursors of Formula I

In some embodiments, the precursor comprises a compound of Formula I. Formula I encompasses the following structure:

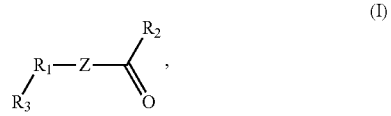

(I)

and includes tautomers thereof, deuterated derivatives of those compounds and their tautomers, pharmaceutically acceptable salts thereof, and $^{13}C$ or $^{15}N$ enriched derivatives at one or more sites. In some embodiments, Z describes: (i) a carbon-carbon double bond (—C=C—) which is substituted to include $^{1}H$ (proton), $^{2}H$ (deuterium), or a combination thereof (e.g., —C$^{1}$H=C$^{1}$H—C$^{1}$H=C$^{2}$H—, —C$^{2}$H=C$^{2}$H—) or (ii) a carbon-carbon triple bond (—C≡C—). In some embodiments, $R_1$ comprises a parahydrogen induced polarization (PHIP) transfer moiety, as described herein. In some embodiments, $R_2$ comprises an optionally substituted hydrocarbon, alkoxy group, primary amine, secondary amine, or tertiary amine, as described herein. In some embodiments, $R_3$ comprises a biorelevant imaging agent, as described herein. In Formula I, all moieties to the right of the $R_3$—$R_1$ bond (i.e., —$R_1$—Z—(C=O)—$R_2$) may be collectively referred to as a sidearm.

In some embodiments, the compound of Formula I has a solubility in water of at least about 1 millimolar (mM), 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1,000 mM, or more, at most about 1,000 mM, 950 mM, 900 mM, 850 mM, 800 mM, 750 mM, 700 mM, 650 mM, 600 mM, 550 mM, 500 mM, 450 mM, 400 mM, 350 mM, 300 mM, 250 mM, 200 mM, 150 mM, 100 mM, 90 mM, 80 mM, 70 mM, 60 mM, 50 mM, 40 mM, 30 mM, 20 mM, 10 mM, 9 mM, 8 mM, 7 mM, 6 mM, 5 mM, 4 mM, 3 mM, 2 mM, 1 mM, or less, or a solubility in water that is within a range defined by any two of the preceding values.

In some embodiments, the compound of Formula I has a solubility in an organic solvent (e.g., acetone, ethanol, chloroform, toluene) of at least about 1 millimolar (mM), 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1,000 mM, or more, at most about 1,000 mM, 950 mM, 900 mM, 850 mM, 800 mM, 750 mM, 700 mM, 650 mM, 600 mM, 550 mM, 500 mM, 450 mM, 400 mM, 350 mM, 300 mM, 250 mM, 200 mM, 150 mM, 100 mM, 90 mM, 80 mM, 70 mM, 60 mM, 50 mM, 40 mM, 30 mM, 20 mM, 10 mM, 9 mM, 8 mM, 7 mM, 6 mM, 5 mM, 4 mM, 3 mM, 2 mM, 1 mM, or less, or a solubility in an organic solvent that is within a range defined by any two of the preceding values.

In some embodiments, the compound of Formula I comprises methyl 4-((2-oxopropanoyl)oxy)but-2-ynoate. In some embodiments, the compound of Formula I comprises methyl 4-((2-hydroxypropanoyl)oxy)but-2-ynoate. In some embodiments, the compound of Formula I comprises 5-((4-methoxy-4-oxobut-2-yn-1-yl)oxy)-4,5-dioxopentanoic acid.

In some embodiments, the compound of Formula I comprises isopropyl 4-((2-oxopropanoyl)oxy)but-2-ynoate. In some embodiments, the compound of Formula I comprises isopropyl 4-((2-hydroxypropanoyl)oxy)but-2-ynoate. In some embodiments, the compound of Formula I comprises 5-((4-isopropoxy-4-oxobut-2-yn-1-yl)oxy)-4,5-dioxopentanoic acid.

In some embodiments, the compound of Formula I comprises tert-butyl 4-((2-oxopropanoyl)oxy)but-2-ynoate. In some embodiments, the compound of Formula I comprises tert-butyl 4-((2-hydroxypropanoyl)oxy)but-2-ynoate. In some embodiments, the compound of Formula I comprises 5-((4-(tert-butoxy)-4-oxobut-2-yn-1-yl)oxy)-4,5-dioxopentanoic acid.

In some embodiments, the compound of Formula I comprises tert-butyl 4-((2-oxopropanoyl-1-$^{13}C$)oxy)but-2-ynoate. In some embodiments, the compound of Formula I comprises tert-butyl 4-((2-hydroxypropanoy-1-$^{13}Cl$)oxy)but-2-ynoate. In some embodiments, the compound of Formula I comprises 5-((4-(tert-butoxy)-4-oxobut-2-yn-1-yl)oxy)-4,5-dioxopentanoic $^{13}C$ acid.

In some embodiments, the compound of Formula I comprises 2-(Methyl-d$_3$)propan-2-yl-1,1,1,3,3,3-d$_6$ 4-((2-oxopropanoyl-1-13C)oxy)but-2-ynoate. In some embodiments, the compound of Formula I comprises 2-(Methyl-d$_3$)propan-2-yl-1,1,1,3,3,3-d$_6$ 4-((2-hydroxypropanoyl-1-13C)oxy)but-2-ynoate. In some embodiments, the compound of Formula I comprises 5-((4-((2-(methyl-d$_3$)propan-2-yl-1,1,1,3,3,3-d$_6$)oxy)-4-oxobut-2-yn-1-yl)oxy)-4,5-dioxopentanoic acid.

In some embodiments, the compound of Formula I comprises tert-butyl 4-((2-oxopropanoyl)oxy)but-2-ynoate-4-d. In some embodiments, the compound of Formula I comprises tert-butyl 4-((2-hydroxypropanoyl)oxy)but-2-ynoate-4-d. In some embodiments, the compound of Formula I comprises 5-((4-(tert-butoxy)-4-oxobut-2-yn-1-yl-1-d)oxy)-4,5-dioxopentanoic acid.

In some embodiments, the compound of Formula I comprises tert-butyl 4-((2-oxopropanoyl)oxy)pent-2-ynoate. In some embodiments, the compound of Formula I comprises tert-butyl 4-((2-hydroxypropanoyl)oxy)pent-2-ynoate. In some embodiments, the compound of Formula I comprises 5-((5-(tert-butoxy)-5-oxopent-3-yn-2-yl)oxy)-4,5-dioxopentanoic acid.

In some embodiments, the compound of Formula I comprises tert-butyl 4-((2-oxopropanoyl)oxy)-4-phenylbut-2-ynoate. In some embodiments, the compound of Formula I comprises tert-butyl 4-((2-hydroxypropanoyl)oxy)-4-phenylbut-2-ynoate. In some embodiments, the compound of Formula I comprises 5-((4-(tert-butoxy)-4-oxo-1-phenylbut-2-yn-1-yl)oxy)-4,5-dioxopentanoic acid.

In some embodiments, the compound of Formula I comprises benzhydryl 4-((2-oxopropanoyl)oxy)but-2-ynoate. In some embodiments, the compound of Formula I comprises benzhydryl 4-((2-hydroxypropanoyl)oxy)but-2-ynoate. In some embodiments, the compound of Formula I comprises 5-((4-(benzhydryloxy)-4-oxobut-2-yn-1-yl)oxy)-4,5-dioxopentanoic acid.

In some embodiments, the compound of Formula I comprises 4-oxo-4-phenylbut-2-yn-1-yl 2-oxopropanoate. In some embodiments, the compound of Formula I comprises 4-oxo-4-phenylbut-2-yn-1-yl 2-hydroxypropanoate. In some embodiments, the compound of Formula I comprises 4,5-dioxo-5-((4-oxo-4-phenylbut-2-yn-1-yl)oxy)pentanoic acid.

In some embodiments, the compound of Formula I comprises 4-oxo-4-(phenyl-d$_5$)but-2-yn-1-yl 2-oxopropanoate. In some embodiments, the compound of Formula I comprises 4-oxo-4-(phenyl-d$_5$)but-2-yn-1-yl 2-hydroxypropanoate. In some embodiments, the compound of Formula I comprises 4,5-dioxo-5-((4-oxo-4-(phenyl-d$_5$)but-2-yn-1-yl)oxy)pentanoic acid.

In some embodiments, the compound of Formula I comprises tert-butyl 4-acetoxybut-2-ynoate. In some embodiments, the compound of Formula I comprises 1-(4-(Tert-butoxy)-4-oxobut-2-yn-1-yl) 5-ethyl 2-oxopentanedioate.

In some embodiments, the compound of Formula I comprises Methyl 4-(2,2-dichloroacetoxy)but-2-ynoate.

In some embodiments, the compound of Formula I comprises trityl 4-((2-oxopropanoyl)oxy)but-2-ynoate. In some embodiments, the compound of Formula I comprises trityl 4-((2-hydroxypropanoyl)oxy)but-2-ynoate. In some embodiments, the compound of Formula I comprises 4,5-dioxo-5-((4-oxo-4-(trityloxy)but-2-yn-1-yl)oxy)pentanoic acid.

In some embodiments, the compound of Formula I comprises 4-(diphenylamino)-4-oxobut-2-yn-1-yl 2-oxopropanoate. In some embodiments, the compound of Formula I comprises 4-(diphenylamino)-4-oxobut-2-yn-1-yl 2-hydroxypropanoate. In some embodiments, the compound of Formula I comprises 5-((4-(diphenylamino)-4-oxobut-2-yn-1-yl)oxy)-4,5-dioxopentanoic acid.

In some embodiments, the compound of Formula I comprises 4-(diisopropylamino)-4-oxobut-2-yn-1-yl 2-oxopropanoate. In some embodiments, the compound of Formula I comprises 4-(diisopropylamino)-4-oxobut-2-yn-1-yl 2-hydroxypropanoate. In some embodiments, the compound of Formula I comprises 5-((4-(diisopropylamino)-4-oxobut-2-yn-1-yl)oxy)-4,5-dioxopentanoic acid.

In some embodiments, the compound of Formula I comprises 4-oxopent-2-yn-1-yl 2-oxopropanoate. In some embodiments, the compound of Formula I comprises 4-oxopent-2-yn-1-yl 2-hydroxypropanoate. In some embodiments, the compound of Formula I comprises 4,5-dioxo-5-((4-oxopent-2-yn-1-yl)oxy)pentanoic acid.

In some embodiments, the compound of Formula I comprises 4-oxo-4-(pyridin-2-yl)but-2-yn-1-yl 2-oxopropanoate. In some embodiments, the compound of Formula I comprises 4-oxo-4-(pyridin-2-yl)but-2-yn-1-yl 2-hydroxypropanoate. In some embodiments, the compound of Formula I comprises 4,5-dioxo-5-((4-oxo-4-(27yridine-2-yl)but-2-yn-1-yl)oxy)pentanoic acid.

In some embodiments, the compound of Formula I comprises 4-(1-methyl-TH-imidazol-2-yl)-4-oxobut-2-yn-1-yl 2-oxopropanoate. In some embodiments, the compound of Formula I comprises 4-(1-methyl-TH-imidazol-2-yl)-4-oxobut-2-yn-1-yl 2-hydroxypropanoate. In some embodiments, the compound of Formula I comprises 5-((4-(1-methyl-1H-imidazol-2-yl)-4-oxobut-2-yn-1-yl)oxy)-4,5-dioxopentanoic acid.

Parahydrogenated Precursors of Formula II

In some embodiments, the compound of Formula I is parahydrogenated (i.e., modified via the addition of parahydrogen protons across Z via a hydrogenation reaction between Formula I and a parahydrogen), as described herein. In some embodiments, parahydrogenation of a compound of Formula I yields a compound of Formula II. Formula II encompasses the following structure:

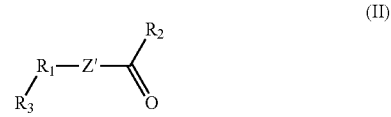

(II)

and includes tautomers thereof, deuterated derivatives of those compounds and their tautomers, pharmaceutically acceptable salts thereof, and $^{13}$C or $^{15}$N enriched derivatives at one or more sites. In some embodiments, Z' is: (i) a parahydrogenated carbon-carbon single bond (—CH*—CH*—) which is substituted to include $^1$H (proton), $^2$H (deuterium), or a combination thereof (e.g., —CH$_2$H*—CH$_2$H*—, —CHDH*—CH$_2$H*—, —CD$_2$H*—CH$_2$H*—), or (ii) a parahydrogenated carbon-carbon double bond (—CH*=CH*—) which is substituted to include $^1$H (proton), $^2$H (deuterium), or a combination thereof. In some embodiments, H* denotes a hydrogen having a spin order derived from parahydrogen (i.e., a hydrogen atom or proton added across the carbon-carbon double bond or the carbon-carbon triple bond Z via a hydrogenation reaction between a compound of Formula I and a parahydrogen, as described herein). In some embodiments, H* denotes a hydrogen having a spin order derived from parahydrogen (e.g., before polarization transfer). In some embodiments, R$_1$ comprises a PHIP transfer moiety, as described herein. In some embodiments, $R_2$ comprises an optionally substituted hydrocarbon, alkoxy group, primary amine, secondary amine, or tertiary amine, as described herein. In some embodiments, $R_3$ comprises a biorelevant imaging agent, as described herein. In Formula II, all moieties to the right of the $R_3$—$R_1$ bond (i.e., —$R_1$—Z'—(C=O)—$R_2$) may be collectively referred to as a parahydrogenated sidearm.

In some embodiments, the compound of Formula II has a solubility in water of at least about 1 millimolar (mM), 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1,000 mM, or more, at most about 1,000 mM, 950 mM, 900 mM, 850 mM, 800 mM, 750 mM, 700 mM, 650 mM, 600 mM, 550 mM, 500 mM, 450 mM, 400 mM, 350 mM, 300 mM, 250 mM, 200 mM, 150 mM, 100 mM, 90 mM, 80 mM, 70 mM, 60 mM, 50 mM, 40 mM, 30 mM, 20 mM, 10 mM, 9 mM, 8 mM, 7 mM, 6 mM, 5 mM, 4 mM, 3 mM, 2 mM, 1 mM, or less, or a solubility in water that is within a range defined by any two of the preceding values.

In some embodiments, the compound of Formula II has a solubility in an organic solvent (e.g., acetone, ethanol, chloroform, toluene) of at least about 1 millimolar (mM), 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1,000 mM, or more, at most about 1,000 mM, 950 mM, 900 mM, 850 mM, 800 mM, 750 mM, 700 mM, 650 mM, 600 mM, 550 mM, 500 mM, 450 mM, 400 mM, 350 mM, 300 mM, 250 mM, 200 mM, 150 mM, 100 mM, 90 mM, 80 mM, 70 mM, 60 mM, 50 mM, 40 mM, 30 mM, 20 mM, 10 mM, 9 mM, 8 mM, 7 mM, 6 mM, 5 mM, 4 mM, 3 mM, 2 mM, 1 mM, or less, or a solubility in an organic solvent that is within a range defined by any two of the preceding values.

In some embodiments, when the composition of Formula I is reacted with parahydrogen, the chemical yield (e.g., chemical yield of a compound of Formula II) is at least about 30%, 35%, 40%, 45%, 50%, 55%, 60%, 65%, 70%, 75%, 80%, 85%, 90%, 95%, or more, at most about 95%, 90%, 85%, 80%, 75%, 70%, 65%, 60%, 55%, 50%, 45%, 40%, 35%, 30%, or less, or within a range defined by any two of the preceding values. For instance, in some embodiments, when the composition of Formula I is reacted with parahydrogen, the chemical yield is between 30% and 35%, between 30% and 40%, between 30% and 45%, between 30% and 50%, between 30% and 55%, between 30% and 60%, between 30% and 65%, between 30% and 70%, between 30% and 75%, between 30% and 80%, between 30% and 85%, between 30% and 90%, between 30% and 95%, between 35% and 40%, between 35% and 45%, between 35% and 50%, between 35% and 55%, between 35% and 60%, between 35% and 65%, between 35% and 70%, between 35% and 75%, between 35% and 80%, between 35% and 85%, between 35% and 90%, between 35% and 95%, between 40% and 45%, between 40% and 50%, between 40% and 55%, between 40% and 60%, between 40% and 65%, between 40% and 70%, between 40% and 75%, between 40% and 80%, between 40% and 85%, between 40% and 90%, between 40% and 95%, between 45% and 50%, between 45% and 55%, between 45% and 60%, between 45% and 65%, between 45% and 70%, between 45% and 75%, between 45% and 80%, between 45% and 85%, between 45% and 90%, between 45% and 95%, between 50% and 55%, between 50% and 60%, between 50% and 65%, between 50% and 70%, between 50% and 75%, between 50% and 80%, between 50% and 85%, between 50% and 90%, between 50% and 95%, between 55% and 60%, between 55% and 65%, between 55% and 70%, between 55% and 75%, between 55% and 80%, between 55% and 85%, between 55% and 90%, between 55% and 95%, between 60% and 65%, between 60% and 70%, between 60% and 75%, between 60% and 80%, between 60% and 85%, between 60% and 90%, between 60% and 95%, between 65% and 70%, between 65% and 75%, between 65% and 80%, between 65% and 85%, between 65% and 90%, between 65% and 95%, between 70% and 75%, between 70% and 80%, between 70% and 85%, between 70% and 90%, between 70% and 95%, between 75% and 80%, between 75% and 85%, between 75% and 90%, between 75% and 95%, between 80% and 85%, between 80% and 90%, between 80% and 95%, between 85% and 90%, between 85% and 95%, or between 90% and 95%.

Cleaved Precursors of Formula III

In some embodiments, a compound of Formula II is cleaved (e.g., hydrolyzed), as described herein. In some embodiments, a compound of Formula II is cleaved (e.g., hydrolyzed), as described herein, to provide a sidearm compound and a corresponding biorelevant imaging agent. In some embodiments, cleavage of a compound of Formula II yields a compound of Formula III and a corresponding biorelevant imaging agent, as described herein. Formula III encompasses the following structure:

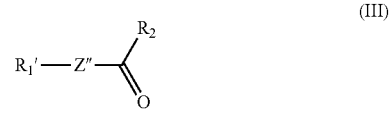

(III)

and includes tautomers thereof, deuterated derivatives of those compounds and their tautomers, pharmaceutically acceptable salts thereof, and $^{13}$C or $^{15}$N enriched derivatives at one or more sites. In some embodiments, Z" is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof. In some embodiments, $R_{1'}$ comprises a PHIP transfer moiety, as described herein. In some embodiments, $R_2$ comprises an optionally substituted hydrocarbon, alkoxy group, primary amine, secondary amine, or tertiary amine, as described herein. In Formula III, all of moieties $R_1$—Z"—(C=O)—$R_2$ may be collectively referred to as a cleaved sidearm or a hydrolyzed sidearm.

In some embodiments, the compound of Formula III has a solubility in water of at least about 1 millimolar (mM), 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1,000 mM, or more, at most about 1,000 mM, 950 mM, 900 mM, 850 mM, 800 mM, 750 mM, 700 mM, 650 mM, 600 mM, 550 mM, 500 mM, 450 mM, 400 mM, 350 mM, 300 mM, 250 mM, 200 mM, 150 mM, 100 mM, 90 mM, 80 mM, 70 mM, 60 mM, 50 mM, 40 mM, 30 mM, 20 mM, 10 mM, 9 mM, 8 mM, 7 mM, 6 mM, 5 mM, 4 mM, 3 mM, 2 mM, 1 mM, or less, or a solubility in water that is within a range defined by any two of the preceding values.

In some embodiments, the compound of Formula III has a solubility in an organic solvent (e.g., acetone, ethanol, chloroform, toluene) of at least about 1 millimolar (mM), 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1,000 mM, or more, at most about 1,000 mM, 950 mM, 900 mM, 850 mM, 800 mM, 750 mM, 700 mM, 650 mM, 600 mM, 550 mM, 500 mM, 450 mM, 400 mM, 350 mM, 300 mM, 250 mM, 200 mM, 150 mM, 100 mM, 90 mM, 80 mM, 70 mM, 60 mM, 50 mM, 40 mM, 30 mM, 20 mM, 10 mM, 9 mM, 8 mM, 7 mM, 6 mM, 5 mM, 4 mM, 3 mM, 2 mM, 1 mM, or less, or a solubility in an organic solvent that is within a range defined by any two of the preceding values.

Sidearms of Formula IV

In some embodiments, biorelevant imaging agents and sidearms, such as the sidearm compound of Formula IV, are conjugated to form precursor compounds, such as the compound of Formula I, as described herein. Formula IV encompasses the following structure:

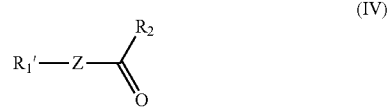

(IV)

and includes tautomers thereof, deuterated derivatives of those compounds and their tautomers, pharmaceutically acceptable salts thereof, and $^{13}$C or $^{15}$N enriched derivatives at one or more sites. In some embodiments, Z describes: (i) a carbon-carbon double bond (—C═C—) which is substituted to include $^{1}$H (proton), $^{2}$H (deuterium), or a combination thereof (e.g., —C$^{1}$H═C$^{1}$H—, —C$^{1}$H═C$^{2}$H—, —C$^{2}$H═C$^{2}$H—) or (ii) a carbon-carbon triple bond (—C≡C—). In some embodiments, R$_1$ comprises a parahydrogen induced polarization (PHIP) transfer moiety, as described herein. In some embodiments, R$_2$ comprises a solubilizing moiety, as described herein. In some embodiments, R$_2$ comprises an optionally substituted hydrocarbon, alkoxy group, primary amine, secondary amine, or tertiary amine. In some embodiments, conjugation of a compound of Formula IV with a biorelevant imaging agent yields a compound of Formula I, as described herein.

PHIP Transfer Moieties

In some embodiments, a PHIP transfer moiety described herein comprises a chemical moiety configured to permit or enhance polarization transfer from one or more parahydrogenated protons H* (e.g., H* in a sidearm) to one or more non-hydrogen nuclear spins of a biorelevant imaging agent (such as one or more $^{13}$C or $^{15}$N atoms of a biorelevant imaging agent, as described herein). In some embodiments, the PHIP transfer moiety permits or enhances polarization transfer from the parahydrogen protons H* in the sidearm of the compound of Formula II to the non-hydrogen nuclear spins of the corresponding biorelevant imaging agent of the compound of Formula II. In some embodiments, the PHIP transfer moiety permits or enhances polarization transfer from the parahydrogen protons H* in the sidearm of the compound of Formula II to the non-hydrogen nuclear spins of the corresponding biorelevant imaging agent of the compound of Formula II, following the parahydrogenation reaction between Formula I and parahydrogen.

In some embodiments, the PHIP transfer moiety comprises an optionally substituted C1 hydrocarbon or an optionally substituted C2 hydrocarbon.

In some embodiments, the PHIP transfer moiety comprises a chemical moiety of the form *CR$_4$R$_5$, *CR$_4$Y, *C═Y, or any deuterated version thereof. In some embodiments, *C is a $^{12}$C or $^{13}$C carbon isotope. In some embodiments, R$_4$ and R$_5$ are each independently selected from: $^{1}$H, $^{2}$H, $^{3}$H, a linear, branched, or cyclic C1-C10 alkyl hydrocarbon, a C6 aryl, a benzyl, a phenyl, a heteroaryl, and a haloalkyl group. In some embodiments, Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group. In some embodiments, the spin-1/2 atom is selected from: $^{1}$H, $^{13}$C, $^{15}$N, $^{19}$F, and $^{31}$P. In some embodiments, the $^{15}$N can be substituted with a nitro group, amine group, amide group, or imine group. In some embodiments, the $^{31}$P can be substituted with one or more keto groups, one or more nitro groups, one or more amine groups, one or more amide groups, or one or more imine groups.

In some embodiments, the PHIP transfer moiety comprises a chemical moiety of the form *CR$_6$R$_7$—*CR$_8$R$_9$, or any deuterated version thereof. In some embodiments, *C is a $^{12}$C or $^{13}$C carbon isotope. In some embodiments, R$_6$, R$_7$, R$_8$, and R$_9$ are each independently selected from: $^{1}$H, $^{2}$H, 3H, a linear, branched, or cyclic C1-C10 alkyl hydrocarbon, a C6 aryl, a benzyl, a phenyl, a heteroaryl, and a haloalkyl group.

In some embodiments, the PHIP transfer moiety comprises a chemical moiety of the form *CH$_2$, *CH$_2$—*CH$_2$, *CHY, *C═Y, or any deuterated version thereof. In some embodiments, *C is a $^{12}$C or $^{13}$C carbon isotope. In some embodiments, Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group. In some embodiments, the spin-1/2 atom is selected from: $^{1}$H, $^{13}$C, $^{15}$N, $^{19}$F, and $^{31}$P.

In some embodiments, the compositions described herein comprise a first J-coupling $J_{12}$ between a spin-1/2 atom described herein and a non-hydrogen nuclear spin described herein. In some embodiments, the compositions described herein comprise a second J-coupling $J_{13}$ between the spin-1/2 atom described herein and a parahydrogen protons H* described herein. In some embodiments, the compositions described herein comprise a third J-coupling $J_{23}$ between the non-hydrogen nuclear spin described herein and the parahydrogen protons H* described herein. In some embodiments, $J_{12}$ and/or $J_{13}$ is greater than $J_{23}$. In such cases, the PHIP transfer moiety may permit or enhance polarization transfer.

In some embodiments, the PHIP transfer moiety induces a J-coupling between one or both of the *H nuclear spins with the non-hydrogen nuclear spins of at least about 0.1 Hz, 0.2 Hz, 0.3 Hz, 0.4 Hz, 0.5 Hz, 0.6 Hz, 0.7 Hz, 0.8 Hz, 0.9 Hz, 1 Hz, 2 Hz, 3 Hz, 4 Hz, 5 Hz, 6 Hz, 7 Hz, 8 Hz, 9 Hz, 10 Hz, or more, at most about 10 Hz, 9 Hz, 8 Hz, 7 Hz, 6 Hz, 5 Hz, 4 Hz, 3 Hz, 2 Hz, 1 Hz, 0.9 Hz, 0.8 Hz, 0.7 Hz, 0.6 Hz, 0.5 Hz, 0.4 Hz, 0.3 Hz, 0.2 Hz, 0.1 Hz, or less, or a J-coupling with the non-hydrogen nuclear spins that is within a range defined by any two of the preceding values. For instance, in some embodiments, the J-coupling is between 1 Hz and 2 Hz, between 1 Hz and 3 Hz, between 1 Hz and 4 Hz, between 1 Hz and 5 Hz, between 1 Hz and 6 Hz, between 1 Hz and 7 Hz, between 1 Hz and 8 Hz, between 1 Hz and 9 Hz, between 1 Hz and 10 Hz, between 2 Hz and 3 Hz, between 2 Hz and 4 Hz, between 2 Hz and 5 Hz, between 2 Hz and 6 Hz, between 2 Hz and 7 Hz, between 2 Hz and 8 Hz, between 2 Hz and 9 Hz, between 2 Hz and 10 Hz, between 3 Hz and 4 Hz, between 3 Hz and 5 Hz, between 3 Hz and 6 Hz, between 3 Hz and 7 Hz, between 3 Hz and 8 Hz, between 3 Hz and 9 Hz, between 3 Hz and 10 Hz, between 4 Hz and 5 Hz, between 4 Hz and 6 Hz, between 4 Hz and 7 Hz, between 4 Hz and 8 Hz, between 4 Hz and 9 Hz, between 4 Hz and 10 Hz, between 5 Hz and 6 Hz, between 5 Hz and 7 Hz, between 5 Hz and 8 Hz, between 5 Hz and 9 Hz, between 5 Hz and 10 Hz, between 6 Hz and 7 Hz, between 6 Hz and 8 Hz, between 6 Hz and 9 Hz, between 6 Hz and 10 Hz, between 7 Hz and 8 Hz, between 7 Hz and 9 Hz, between 7 Hz and 10 Hz, between 8 Hz and 9 Hz, between 8 Hz and 10 Hz, or between 9 Hz and 10 Hz.

$R_2$ Groups

In some embodiments, an $R_2$ group described herein comprises an optionally substituted hydrocarbon, alkoxy group, primary amine, secondary amine, or tertiary amine. In some embodiments, an $R_2$ group described herein comprises an optionally substituted hydrocarbon, alkoxy group, primary amine, secondary amine, or tertiary amine that functions as a solubilizing moiety. In some embodiments, an $R_2$ group described herein comprises a solubilizing moiety. In some embodiments, the solubilizing moiety comprises any chemical moiety configured to permit or enhance the solubility of a compound, such as any of the compounds of Formula I, II, III, and/or IV in a solution in which the parahydrogenation reaction or the cleavage (e.g., hydrolysis) reaction takes place. In some embodiments, the enhancement of the solubility is measured with respect to a variant of the compound of Formula I, II, III, or IV that utilizes one or more protons in place of the $R_2$ group. In some embodiments, the enhancement of the solubility is measured with respect to a variant of the compound of Formula I, II, III, or IV that utilizes a methyl group as the $R_2$ group.

In some embodiments, the solubilizing moiety comprises a hydrophobic moiety or an organophilic moiety. In some embodiments, the solubilizing moiety comprises an organic solubilizing moiety. For example, in some embodiments, the solubilizing moiety comprises a hydrophobic moiety, an organophilic moiety, or an organic solubilizing moiety. In some embodiments, the solubilizing moiety comprises a hydrophilic moiety or an organophobic moiety.

In some embodiments, the $R_2$ group comprises, or is selected from: a methyl group, an ethyl group, a propyl group, an isopropyl group, an n-butyl group, an s-butyl group, a t-butyl group, an isobutyl group, a hydroxy group, a methyl alcohol group, an ethyl alcohol group, an n-propanol group, an isopropyl alcohol group a propionic alcohol group, an n-butyl alcohol group, an s-butyl alcohol group, a t-butyl alcohol group, an isobutyl alcohol group, a methoxy group, an ethoxy group, a propoxy group, an isopropxy, a propionic group, a butoxy group, a t-butoxy group, a s-butoxy group, an ester group, a phenyl group, a substituted phenyl group, a primary amine group, a secondary amine group, a tertiary amine group, a primary amide group, a secondary amide group, and a tertiary amide group. In some embodiments, the substituted phenyl group is selected from fluorobenzene, chlorobenzene, bromobenzene, iodobenzene, toluene, cumene, ethylbenzene, styrene, ortho-xylene, meta-xylene, para-xylene, phenol, benzoic acid, benzaldehyde, acetophenone, methyl benzoate, anisole, aniline, nitrobenzene, benzonitrile, benzamide, benzenesulfonic acid, naphthalene, and anthracene.

$R_3$ Groups

In some embodiments, an $R_3$ group described herein comprises a biorelevant imaging agent. In some embodiments, the biorelevant imaging agent has the formula $R_4C(=O)X-$. In some embodiments, $R_4$ is chosen from a linear, branched, or cyclic C1-C10 alkyl group, in which one or more C atoms are optionally substituted with CO, COOH, $CH_2COOH$, $CONH_2$, an OH, an amino (NR'R''), one or more halogen atoms, one or more halo-alkyl groups, or one or more carbocycles, wherein the carbocycle is optionally substituted with one or more aliphatic or aromatic ring, which is optionally substituted by one or more functional groups. In some embodiments, X is chosen from NR''' and O. In some embodiments, R', R'', and R''' are each independently selected from $^1H$, $^2H$, $^3H$, and an amino protecting group, optionally selected from trifluoroacetyl, acetyl, benzoyl, carbobenzoxy, tert-butyl carbonate and benzyl. In some embodiments, the $R_3$ group comprises any biorelevant imaging agent described herein.

In some embodiments, the $R_3$ group comprises at least one non-hydrogen nuclear spin. In some embodiments, the non-hydrogen nuclear comprises at least one spin-1/2 atom. In some embodiments, the non-hydrogen nuclear spin comprises $^{13}C$ or $^{15}N$. In some embodiments, the $R_3$ group is at least partially isotopically labeled with the non-hydrogen nuclear spin. In some embodiments, the $R_3$ group is at least partially enriched with the non-hydrogen nuclear spin when compared to an analog of the $R_3$ group that features the non-hydrogen nuclear spin at its natural abundance. In some embodiments, the $R_3$ group is enriched to feature the non-hydrogen nuclear spin at an abundance of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%9, 92%, 93%, 94%, 95%, 96%, 97%, 98%, 99%, or more, at most about 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less, or an abundance that is within a range defined by any two of the preceding values.

In some embodiments, the non-hydrogen nuclear spin replaces an NMR-inactive (i.e., spin-0) nucleus (e.g., $^{12}C$ or a quadrupolar (i.e., spin>1/2) nucleus (e.g., $^{14}N$) of the analog of the $R_3$ group that features the non-hydrogen nuclear spin at its natural abundance, as described herein. In some embodiments, the non-hydrogen nuclear spin is located no more than about 1 or 2 chemical bonds from the carbonyl (C=O) carbon in the $R_3$ group.

Parahydrogenation

Consistent with disclosed embodiments, a precursor to the biorelevant imaging agent (such as a compound of Formula I, as described herein) can be parahydrogenated by combining the precursor, parahydrogen, and a hydrogenation catalyst. The disclosed embodiments are not limited to a particular method of generating a parahydrogenated precursor. In some embodiments, the precursor is added to a mixture containing parahydrogen. In some embodiments, parahydrogen gas is added to a solution containing the precursor (e.g., the parahydrogen gas can be bubbled into such a solution). In hydrogenating the precursor, the parahydrogen can create IzIIz2 order, preferential population of the lower energy state between |↑>|↓>, |↓>|↑> or singlet spin order on two hydrogens spins in the precursor.

The precursor can have an unsaturated bond (such as an unsaturated carbon-carbon double bond or an unsaturated carbon-carbon triple bond) that can be hydrogenated by the parahydrogen gas. Following combination of the precursor and the parahydrogen, at least about 10%, 20%, 30%, 40%, 50%, 60%, 70%, 80%, 90%, or more of the precursor, at most about 90%, 80%, 70%, 60%, 50%, 40%, 30%, 20%, 10%, or less of the precursor, or a percentage of the precursor that is within a range defined by any two of the preceding values may be hydrogenated.

In some embodiments, the parahydrogenated precursor has a population difference in the parahydrogenated proton spin states of at least about 1%, 2%, 3%, 4%, 5%, 6%, 7%, 8%, 9%, 10%, 15%, 20%, 25%, 30%, 40%, 45%, 50%, or more, at most about 50%, 45%, 40%, 35%, 30%, 25%, 20%1, 5%1, 0%, 9%, 8%, 7%, 6%, 5%, 4%, 3%, 2%, 1%, or less, or a population difference that is within a range defined by any two of the preceding values. For instance, in some embodiments, the population difference is between 10% and 15%, between 10% and 20%, between 10% and 25%, between 10% and 30%, between 10% and 35%, between 10% and 40%, between 10% and 45%, between 10% and 50%, between 15% and 20%, between 15% and 25%, between 15% and 30%, between 15% and 35%, between 15% and 40%, between 15% and 45%, between 15% and 50%, between 20% and 25%, between 20% and 30%, between 20% and 35%, between 20% and 40%, between 20% and 45%, between 20% and 50%, between 25% and 30%, between 25% and 35%, between 25% and 40%, between 25% and 45%, between 25% and 50%, between 30% and 35%, between 30% and 40%, between 30% and 45%, between 30% and 50%, between 35% and 40%, between 35% and 45%, between 35% and 50%, between 40% and 45%, between 40% and 50%, or between 45% and 50%. In some embodiments, the population difference is between spin states which include the parahydrogenated protons as well as other nuclear spins, for example additional protons on the compound. In some embodiments, the parahydrogenated precursor includes a sidearm and the parahydrogenated spins can be located on the sidearm.

In some embodiments, the concentration of the hydrogenation catalyst during hydrogenation is at least about 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, or more, at most about 100 mM, 90 mM, 80 mM, 70 mM, 60 mM, 50 mM, 40 mM, 30 mM, 20 mM, 10 mM, 9 mM, 8 mM, 7 mM, 6 mM, 5 mM, 4 mM, 3 mM, 2 mM, 1 mM, 0.9 mM, 0.8 mM, 0.7 mM, 0.6 mM, 0.5 mM, 0.4 mM, 0.3 mM, 0.2 mM, 0.1 mM, or less, or within a range defined by any two of the preceding values.

The disclosed embodiments can include methods implemented by the disclosed systems for generating a hyperpolarized biorelevant imaging agent. The disclosed methods can include mixing (e.g., by a mixing mechanism) a solution which includes a precursor to the biorelevant imaging agent and a hydrogenation catalyst. A mixing mechanism may be a device for introducing, holding, and facilitating a blend, mixture, or solution of two or more materials. In some embodiments, the mixing mechanism is disposed in a chamber, and the mixing occurs inside the chamber. In some embodiments, the solution is mixed at a location away from the chamber. The solution may be at least about 1 milliliter (ml), 2 ml, 3 ml, 4 ml, 5 ml, 6 ml, 7 ml, 8 ml, 9 ml, 10 ml, 20 ml, 30 ml, 40 ml, 50 ml, 60 ml, 70 ml, 80 ml, 90 ml, 100 ml, or more in volume, at most about 100 ml, 90 ml, 80 ml, 70 ml, 60 ml, 50 ml, 40 ml, 30 ml, 20 ml, 10 ml, 9 ml, 8 ml, 7 ml, 6 ml, 5 ml, 4 ml, 3 ml, 2 ml, 1 ml, or less in volume, or within a volume range defined by any two of the preceding values.

In some embodiments, the mixing mechanism is a gas-liquid exchange mechanism. For example, the gas-liquid exchange mechanism may be a bubbler or a diffusion system. In some embodiments, the mixing mechanism comprises membranes adapted to permit diffusion of molecular hydrogen. In some embodiments the mixing can be performed using a spray chamber, where the solution is sprayed into a chamber filled with pressurized parahydrogen.

In some embodiments, the catalyst is a molecule, complex or particle system that catalyzes hydrogenation. In some embodiment, the catalyst comprises a homogeneous metal catalyst such as a rhodium complex or a ruthenium complex. The rhodium complex can be used for coordination and activation of precursor molecules and parahydrogen. In some embodiments, a heterogeneous metal catalyst is connected to a nanoparticle.

Various embodiments of the present disclosure describe introducing a solution which includes a precursor to the biorelevant imaging agent and a hydrogenation catalyst into a chamber configured to hold the solution during polarization transfer. In some embodiments, the solution is mixed in the chamber. In some embodiments, the solution is hydrogenated in the chamber. In some embodiments, the chamber is within a magnetic shield (e.g., a mu metal shield). The magnetic shield can reduce the effect of the Earth's magnetic field (or other extraneous magnetic fields), permitting modulation of the amplitude of a low-level magnetic field applied to the solution. Accordingly, placing the solution within the chamber can include placing the solution within the magnetic shield.

As described herein, in some embodiments parahydrogenation occurs prior to polarization transfer (e.g., prior to the modulation of the amplitude the magnetic field applied to the solution, or the like). In some embodiments, parahydrogenation occurs during polarization transfer. For example, parahydrogen can be combined with (e.g., flowed or bubbled through the solution) the solution during modulation of the amplitude of the magnetic field.

In some embodiments, the parahydrogen gas is combined with the solution in a hydrogenation chamber at pressure. The pressure can be at least about 10 bar, 15 bar, 20 bar, 30 bar, 50 bar, or more, at most about 50 bar, 30 bar, 20 bar, 15 bar, 10 bar or less, or within a range defined by any two of the preceding values. In some embodiments, the parahydrogen is combined with the solution in a metallic chamber capable of withstanding the pressure. The parahydrogen can be combined with the solution for (or the dissolution of the parahydrogen can occur in less than) a time interval. The time interval can be at most about 90 seconds, 60 seconds, 30 seconds, 20 seconds, 10 seconds, 9 seconds, 8 seconds, 7 seconds, 6 seconds, 5 seconds, 4 seconds, 3 seconds, 2 seconds, 1 second, or less, at least about 1 second, 2 seconds, 3 seconds, 4 seconds, 5 seconds, 6 seconds, 7 seconds, 8 seconds, 9 seconds, 10 seconds, 20 seconds, 30 seconds, 60 seconds, 90 seconds, or more, or within a range defined by any two of the preceding values. In some embodiments, the hydrogenation is carried out or occurs within the time interval.

Polarization Transfer Using Radiofrequency Waveforms

In some embodiments, the concentration of the precursor in the solution prior to polarization transfer is at least about 10 mM, 20 mM, 30 mM, 40 mM, 50 mM, 60 mM, 70 mM, 80 mM, 90 mM, 100 mM, 200 mM, 300 mM, 400 mM, 500 mM, 600 mM, 700 mM, 800 mM, 900 mM, 1,000 mM, or more, at most about 1,000 mM, 900 mM, 800 mM, 700 mM, 600 mM, 500 mM, 400 mM, 300 mM, 200 mM, 100 mM, 90 mM, 80 mM, 70 mM, 60 mM, 50 mM, 40 mM, 30 mM 20 mM, 10 mM, or less, or within a range defined by any two of the preceding values. The volume of the solution can be at least about 1 ml, 2 ml, 3 ml, 4 ml, 5 ml, 6 ml, 7 ml, 8 ml, 9 ml, 10 ml, 20 ml, 30 ml, 40 ml, 50 ml, 60 ml, 70 ml, 80 ml, 90 ml, 100 ml, 200 ml, 300 ml, 400 ml, 500 ml, 600 ml, 700 ml, 800 ml, 900 ml, 1000 ml, 2000 ml, or more, at most about 2000 ml, 1000 ml, 900 ml, 800 ml, 700 ml, 600 ml, 500 ml, 400 ml, 300 ml, 200 ml, 100 ml, 90 ml, 80 ml, 70 ml, 60 ml, 50 ml, 40 ml, 30 ml, 20 ml, 10 ml, 9 ml, 8 ml, 7 ml, 6 ml, 5 ml, 4 ml, 3 ml, 2 ml, 1 ml, or less, or within a range defined by any two of the preceding values.

Various embodiments of the present disclosure describe applying a polarization transferring magnetic perturbation aimed to generate a magnetic field around the solution (e.g., around a solution containing Formula II described herein). In some embodiments, the magnetic field has a strength of at least about 0.1 gauss (G), 0.2 G, 0.3 G, 0.4 G, 0.5 G, 0.6 G, 0.7 G, 0.8 G, 0.9 G, 1 G, 2 G, 3 G, 4 G, 5 G, 6 G, 7 G, 8 G, 9 G, 10 G, 20 G, 30 G, 40 G, 50 G, 60 G, 70 G, 80 G, 90 G, 100 G, 200 G, 300 G, 400 G, 500 G, 600 G, 700 G, 800 G, 900 G, 1,000 G, 2,000 G, 3,000 G, 4,000 G, 5,000 G, 6,000 G, 7,000 G, 8,000 G, 9,000 G, 10,000 G, 20,000 G, 30,000 G, 40,000 G, 50,000 G, 60,000 G, 70,000 G, 80,000 G, 90,000 G, 100,000 G, 200,000 G, or more, at most about 200,000 G, 100,000 G, 90,000 G, 80,000 G, 70,000 G, 60,000 G, 50,000 G, 40,000 G, 30,000 G, 20,000 G, 10,000 G, 9,000 G, 8,000 G, 7,000 G, 6,000 G, 5,000 G, 4,000 G, 3,000 G, 2,000 G, 1,000 G, 900 G, 800 G, 700 G, 600 G, 500 G. 400 G, 300 G. 200 G, 100 G, 90 G, 80 G, 70 G, 60 G, 50 G, 40 G, 30 G, 20 G, 10 G, 9 G, 8 G, 7 G, 6 G, 5 G, 4 G, 3 G, 2 G, 1 G, 0.9 G, 0.8 G, 0.7 G, 0.6 G, 0.5 G, 0.4 G, 0.3 G, 0.2 G, 0.1 G, or less, or within a range defined by any two of the preceding values. In some embodiments, the magnetic field has a strength of 0.1 G to 200,000 G around the solution. The magnetic perturbation can be produced by an electro-magnet or a permanent magnet. The magnetic field can be applied to the sample in pulses or in a continuous wave (CW). The magnetic perturbation can be static or time varying.

A signal generator can be configured to generate one or more radiofrequency (RF) waveforms that can be applied to the sample to transfer polarization. The signal generator can include one more computing unit, processors, controllers, associate memories, PCs, computers services, or any devices capable of carrying computational operations using inputs and producing outputs. In some embodiments, RF coils may radiate, or 'apply' the pulse sequences, including the first RF waveform. In some embodiments, the RF coils may have one or more channels. Channels may be pathways for RF signals. There may be provided at least one channel for each different type of NMR spectroscopy. In some embodiments, there is at least one channel for $^1H$ and at least one channel for any of $^2H$, $^{13}C$, $^{15}N$, $^{19}F$, and $^{31}P$. For example, a first RF waveform can be applied to a $^1H$ channel of the one or more radiofrequency coils (RF coils) disposed around the sample. In some embodiments, a second RF waveform is applied to a $^{13}C$ channel of the RF coils. In some embodiments, the RF waveforms on the $^1H$ channel and $^{13}C$ channel are configured to apply a polarization transfer sequence, such as PH-INEPT, Goldman's sequence, S2M, S2hM, SLIC, ADAPT or ESOTERIC.

In some embodiments, the RF waveforms is configured to support polarization transfer, even in the presence of a large proton full width half maximum (FWHM). Such RF waveforms can include a pulse sequence, which can include tens to hundreds of RF pulses. The sequence can be configured such that the pulses protect against the detrimental effects of magnetic field inhomogeneities on polarization transfer.

In some embodiments, a pulse sequence for polarization is configured to transfer the spin order from non-equivalent two $^1H$ hydrogenated spins, e.g., when the chemical shift difference is larger than the J-coupling between them. ESOTHERIC, for example, may be a pulse sequence suited for polarization transfer in this regime.

In some embodiments, the pulse sequence is configured to transfer the spin order from equivalent $^1H$ hydrogen spins, e.g., when the chemical shift difference is smaller than the J-coupling between them. Such pulse sequences may be used in magnetic fields having a strength of at least about 0.01 millitesla (mT), 0.02 mT, 0.03 mT, 0.04 mT, 0.05 mT, 0.06 mT, 0.07 mT, 0.08 mT, 0.09 mT, 0.1 mT, 0.2 mT, 0.3 mT, 0.4 mT, 0.5 mT, 0.6 mT, 0.7 mT, 0.8 mT, 0.9 mT, 1 mT, 2 mT, 3 mT, 4 mT, 5 mT, 6 mT, 7 mT, 8 mT, 9 mT, 10 mT, 20 mT, 30 mT, 40 mT, 50 mT, 60 mT, 70 mT, 80 mT, 90 mT, 100 mT, 200 mT, 300 mT, 400 mT, 500 mT, 600 mT, 700 mT, 800 mT, 900 mT, 1,000 mT, 2,000 mT, 3,000 mT, 4,000 mT, 5,000 mT, 6,000 mT, or more, at most about 6,000 mT, 5,000 mT, 4,000 mT, 3,000 mT, 2,000 mT, 1,000 mT, 900 mT, 800 mT, 700 mT, 600 mT, 500 mT, 400 mT, 300 mT, 200 mT, 100 mT, 90 mT, 80 mT, 70 mT, 60 mT, 50 mT, 40 mT, 30 mT, 20 mT, 10 mT, 9 mT, 8 mT, 7 mT, 6 mT, 5 mT, 4 mT, 3 mT, 2 mT, 1 mT, 0.9 mT, 0.8 mT, 0.7 mT, 0.6 mT, 0.5 mT, 0.4 mT, 0.3 mT, 0.2 mT, 0.1 mT, 0.09 mT, 0.08 mT, 0.07 mT, 0.06 mT, 0.05 mT, 0.04 mT, 0.03 mT, 0.02 mT, 0.01 mT, or less, or within a range defined by any two of the preceding values. An example of such a sequence may be Goldman's sequence (M. Goldman, H. Jóhannesson, C. R. Phys. 2005, 6, 575-581, which is incorporated herein by reference as related to pulse sequence configurations to transfer spin order), the singlet to heteronuclear magnetization (S2hM) sequence, or other sequences used in singlet NMR (e.g. ADAPT, SLIC, etc.).

In some embodiments, a magnetic shield is configured to maintain a magnetic field applied to the solution of at least about 0 mG, 0.1 mG, 0.2 mG, 0.3 mG, 0.4 mG, 0.5 mG, 0.6 mG, 0.7 mG, 0.8 mG, 0.9 mG, 1 mG, 2 mG, 3 mG, 4 mG, 5 mG, 6 mG, 7 mG, 8 mG, 9 mG, 10 mG, 20 mG, 30 mG, 40 mG, 50 mG, 60 mG, 70 mG, 80 mG, 90 mG, 100 mG, or more, at most about 100 mG, 90 mG, 80 mG, 70 mG, 60 mG, 50 mG, 40 mG, 30 mG, 20 mG, 10 mG, 9 mG, 8 mG, 7 mG, 6 mG, 5 mG, 4 mG, 3 mG, 2 mG, 1 mG, 0.9 mG, 0.8 mG, 0.7 mG, 0.6 mG, 0.5 mG, 0.4 mG, 0.3 mG, 0.2 mG, 0.1 mG or less, or a magnetic field that is within a range defined by any two of the preceding values. The magnetic shield can maintain the magnetic field strength within the polarization chamber at such amplitudes during application of the polarization waveform to the one or more radiofrequency coils.

Consistent with disclosed embodiments, the RF waveform can be applied to a solution containing a parahydrogenated precursor.

Transferring Polarization Using Magnetic Field Modulation

In some embodiments, the polarization transfer magnetic perturbation is performed in a magnetic shield (e.g., a mu shield, or the like) to achieve a homogenous, low magnetic field. The magnetic shield enables performance of polarization transfer to $^{13}C$ nuclear spins at microtesla ($\mu T$) magnetic fields, below the earth's magnetic field. The low magnetic field can be at least about 0 mG, 0.1 mG, 0.2 mG, 0.3 mG, 0.4 mG, 0.5 mG, 0.6 mG, 0.7 mG, 0.8 mG, 0.9 mG, 1 mG, 2 mG, 3 mG, 4 mG, 5 mG, 6 mG, 7 mG, 8 mG, 9 mG, 10 mG, 20 mG, 30 mG, 40 mG, 50 mG, 60 mG, 70 mG, 80 mG, 90 mG, 100 mG, or more, at most about 100 mG, 90 mG, 80 mG, 70 mG, 60 mG, 50 mG, 40 mG, 30 mG, 20 mG, 10 mG, 9 mG, 8 mG, 7 mG, 6 mG, 5 mG, 4 mG, 3 mG, 2 mG, 1 mG, 0.9 mG, 0.8 mG, 0.7 mG, 0.6 mG, 0.5 mG, 0.4 mG, 0.3 mG, 0.2 mG, 0.1 mG, or less, or within a range defined by any two of the preceding values.

At such fields, the polarization is transferred by utilizing level avoided crossings (LAC) between the proton spins and other spin species of interest, including $^2H$, $^{13}C$, $^{15}N$, $^{19}F$, and $^{31}P$. In some embodiments, the magnetic field can be tuned to a specific magnetic field strength for the LAC. In various embodiments, to enable robust polarization transfer in larger-volume samples, the magnetic field strength can be temporally modulated. For example, the magnetic field strength can be swept through the LAC conditions. Alternatively or additionally, the sample can be physically moved inside the magnetic field. Such modulation can relax constraints on magnetic field homogeneity and on magnetic field offsets. Thus, robust polarization transfer can be performed at larger volumes and with greater efficiency. Furthermore, relaxing the constraints on magnetic field homogeneity and on magnetic field offsets can permit using of less complex, precise, or expensive polarization systems.

A lower bound of the magnetic field modulation can at least about −10 $\mu T$, −9 $\mu T$, −8 $\mu T$, −7 $\mu T$, −6 $\mu T$, −5 $\mu T$, −4 $\mu T$, −3 $\mu T$, −2 $\mu T$, −1 $\mu T$, −0.9 $\mu T$, −0.8 $\mu T$, −0.7 $\mu T$, −0.6 $\mu T$, −0.5 $\mu T$, −0.4 $\mu T$, −0.3 $\mu T$, −0.2 $\mu T$, −0.1 $\mu T$, or more, at most about −0.1 $\mu T$, −0.2 $\mu T$, −0.3 $\mu T$, −0.4 $\mu T$, −0.5 $\mu T$, −0.6 $\mu T$, −0.7 $\mu T$, −0.8 $\mu T$, −0.9 $\mu T$, −1 $\mu T$, −2 $\mu T$, −3 $\mu T$, −4 $\mu T$, −5 $\mu T$, −6 $\mu T$, −7 $\mu T$, −8 $\mu T$, −9 $\mu T$, −10 $\mu T$, or less, or within a range defined by any two of the preceding values. An upper bound of the modulation can be at least about 0.1 $\mu T$, 0.2 $\mu T$, 0.3 $\mu T$, 0.4 $\mu T$, 0.5 $\mu T$, 0.6 $\mu T$, 0.7 $\mu T$, 0.8 $\mu T$, 0.9 $\mu T$, 1 $\mu T$, 2 $\mu T$, 3 $\mu T$, 4 $\mu T$, 5 $\mu T$, 6 $\mu T$, 7 $\mu T$, 8 $\mu T$, 9 $\mu T$, 10 $\mu T$, or more, at most about 10 $\mu T$, 9 $\mu T$, 8 $\mu T$, 7 $\mu T$, 6 $\mu T$, 5 $\mu T$, 4 $\mu T$, 3 $\mu T$, 2 $\mu T$, 1 $\mu T$, 0.9 $\mu T$, 0.8 $\mu T$, 0.7 $\mu T$, 0.6 $\mu T$, 0.5 $\mu T$, 0.4 $\mu T$, 0.3 $\mu T$, 0.2 $\mu T$, 0.1 $\mu T$, or less, or within a range defined by any two of the preceding values.

The magnetic field can have such an amplitude over a volume of at least about 1 ml, 2 ml, 3 ml, 4 ml, 5 ml, 6 ml, 7 ml, 8 ml, 9 ml, 10 ml, 20 ml, 30 ml, 40 ml, 50 ml, 60 ml, 70 ml, 80 ml, 90 ml, 100 ml, 200 ml, 300 ml, 400 ml, 500 ml, 600 ml, 700 ml, 800 ml, 900 ml, 1,000 ml, 2,000 ml, or more, at most about 2,000 ml, 1,000 ml, 900 ml, 800 ml, 700 ml, 600 ml, 500 ml, 400 ml, 300 ml, 200 ml, 100 ml, 90 ml, 80 ml, 70 ml, 60 ml, 50 ml, 40 ml, 30 ml, 20 ml, 10 ml, 9 ml, 8 ml, 7 ml, 6 ml, 5 ml, 4 ml, 3 ml, 2 ml, 1 ml, or less, or a volume that is within a range defined by any two of the preceding values. The modulation can be performed over a duration. The duration can be at least about 100 milliseconds (ms), 200 ms, 300 ms, 400 ms, 500 ms, 600 ms, 700 ms, 800 ms, 900 ms, 1,000 ms, 2,000 ms, 3,000 ms, 4,000 ms, 5,000 ms, 6,000 ms, 7,000 ms, 8,000 ms, 9,000 ms, 10,000 ms, 20,000 ms, 30,000 ms, 40,000 ms, 50,000 ms, or more, at most about 50,000 ms, 40,000 ms, 30,000 ms, 20,000 ms, 10,000 ms, 9,000 ms, 8,000 ms, 7,000 ms, 6,000 ms, 5,000 ms, 4,000 ms, 3,000 ms, 2,000 ms, 1,000 ms, 900 ms, 800 ms, 700 ms, 600 ms, 500 ms, 400 ms, 300 ms, 200 ms, 100 ms, or less, or within a range defined by any two of the preceding values.

Accordingly, the rate of change of the amplitude of the magnetic field can be at least about 0.01 T per second, 0.02 T per second, 0.03 T per second, 0.04 T per second, 0.05 $\mu T$ per second, 0.06 $\mu T$ per second, 0.07 $\mu T$ per second, 0.08 $\mu T$ per second, 0.09 $\mu T$ per second, 0.1 $\mu T$ per second, 0.2 $\mu T$ per second, 0.03 $\mu T$ per second, 0.4 $\mu T$ per second, 0.5 $\mu T$ per second, 0.6 $\mu T$ per second, 0.7 $\mu T$ per second, 0.8 $\mu T$ per second, 0.9 $\mu T$ per second, 1 $\mu T$ per second, or more, at most about 1 $\mu T$ per second, 0.9 $\mu T$ per second, 0.8 $\mu T$ per second, 0.7 $\mu T$ per second, 0.6 $\mu T$ per second, 0.5 $\mu T$ per second, 0.4 $\mu T$ per second, 0.3 $\mu T$ per second, 0.2 $\mu T$ per second, 0.1 $\mu T$ per second, or less, or within a range defined by any two of the preceding values. The upper bound on the rate of change of the amplitude of the magnetic field may be determined by the capabilities of the equipment used to perform the sweep.

In some embodiments, when the magnetic field is within the upper and lower bounds, disclosed above, the spatial deviation of the magnetic field over the volume during modulation is less than about half (or a quarter, or an eighth, or a tenth) of the amplitude of the magnetic field. For example, when the magnetic field strength is less than 2 $\mu T$ (or greater than −2 $\mu T$) then the spatial deviation of the magnetic field over the volume during modulation can be less than 1 $\mu T$. As an additional example, when the magnetic field strength is less than 10 $\mu T$ (or greater than −10 $\mu T$) then the spatial deviation of the magnetic field over the volume during modulation can be less than 5 $\mu T$. The spatial deviation can be measured for example by taking at least about 10, 20, 30, 40, 50, 60, 70, 80, 90, 100, 200, 300, 400, 500, or more spatially randomly sampled or spatially equally distributed measurements of the magnetic field within the volume and calculating the standard deviation of the sampled magnetic field measurements. Such homogeneity can be achieved for example in a large homogeneous magnetic shield by having a large piercing solenoid through the magnetic shield or by using large Helmholtz coils with a large homogeneous region for producing the magnetic field amplitude modulation. In some embodiments the modulation is a sweep of the magnetic field. In some embodiments, the magnetic field amplitude modulation includes a diabatic jump, monotonous amplitude variation or combinations thereof.

In some embodiments, following the polarization transfer step, a non-hydrogen nuclear spin of the biorelevant imaging agent (such as a $^{13}C$ or $^{15}N$ of the biorelevant imaging agent) has nuclear spin polarization of at least about 1%, 2%, 3%, 4%, 5%, 6%, 7%, 8%, 9%, 10%, 15%, 20%, 25%, 30%, 35%, 40%, 45%, 50%, or more, at most about 50%, 45%, 40%, 35%, 30%, 25%, 20%, 15%, 10%, 9%, 8%, 7%, 6%, 5%, 4%, 3%, 2%, 1% or less, or a polarization that is within a range defined by any two of the preceding values. For example, in some embodiments, following the polarization transfer step, a non-hydrogen nuclear spin of the biorelevant imaging agent has nuclear spin polarization between 10% and 15%, between 10% and 20%, between 10% and 25%, between 10% and 30%, between 10% and 35%, between 10% and 40%, between 10% and 45%, between 10% and 50%, between 15% and 20%, between 15% and 25%, between 15% and 30%, between 15% and 35%, between 15% and 40%, between 15% and 45%, between 15% and 50%, between 20% and 25%, between 20% and 30%, between 20% and 35%, between 20% and 40%, between 20% and 45%, between 20% and 50%, between 25% and 30%, between 25% and 35%, between 25% and 40%, between 25% and 45%, between 25% and 50%, between 30% and 35%, between 30% and 40%, between 30% and 45%, between 30% and 50%, between 35% and 40%, between 35% and 45%, between 35% and 50%, between 40% and 45%, between 40% and 50%, or between 45% and 50%.

In some embodiments this polarization is achieved for a solution volume of at least about 1 ml, 2 ml, 3 ml, 4 ml, 5 ml, 6 ml, 7 ml, 8 ml, 9 ml, 10 ml, 20 ml, 30 ml, 40 ml, 50 ml, 60 ml, 70 ml, 80 ml, 90 ml, 100 ml, 200 ml, 300 ml, 400 ml, 500 ml, or more, at most about 500 ml, 400 ml, 300 ml, 200 ml, 100 ml, 90 ml, 80 ml, 70 ml, 60 ml, 50 ml, 40 ml, 30 ml, 20 ml, 10 ml, 9 ml, 8 ml, 7 ml, 6 ml, 5 ml, 4 ml, 3 ml, 2 ml, 1 ml, or less, or a volume that is within a range defined by any two of the preceding values.

In some embodiments, following polarization transfer a portion of the population difference in parahydrogenated proton spin states has been transferred to polarization of the target (e.g., $^{13}C$ or $^{15}N$) nuclear spin of the biorelevant imaging agent. This portion can be at least about 1%, 2%, 3%, 4%, 5%, 6%, 7%, 8%, 9%, 10%, 15%, 20%, 25%, 30%, 35%, 40%, 45%, 50%, or more, at most about 50%, 45%, 40%, 35%, 30%, 25%, 20%, 15%, 10%, 9%, 8%, 7%, 6% 5%, 4%, 3%, 2%, 1% or less, or within a range defined by any two of the preceding values. For example, in some embodiments, this portion is between 10% and 15%, between 10% and 20%, between 10% and 25%, between 10% and 30%, between 10% and 35%, between 10% and 40%, between 10% and 45%, between 10% and 50%, between 15% and 20%, between 15% and 25%, between 15% and 30%, between 15% and 35%, between 15% and 40%, between 15% and 45%, between 15% and 50%, between 20% and 25%, between 20% and 30%, between 20% and 35%, between 20% and 40%, between 20% and 45%, between 20% and 50%, between 25% and 30%, between 25% and 35%, between 25% and 40%, between 25% and 45%, between 25% and 50%, between 30% and 35%, between 30% and 40%, between 30% and 45%, between 30% and 50%, between 35% and 40%, between 35% and 45%, between 35% and 50%, between 40% and 45%, between 40% and 50%, or between 45% and 50%.

In some embodiments, the magnetic field modulation includes a diabatic jump of the magnetic field. The diabatic jump can be performed to a magnetic field where a level avoided crossing including the proton spins and a non-proton spin occur. Given the J-couplings between the nuclear spins in the system, this value can be calculated analytically or identified by plotting the energy levels of the Hamiltonian for different magnetic fields and identifying the LAC. In some embodiments, the duration where the magnetic field amplitude is at the LAC condition is at most about 5 seconds, 4 seconds, 3 seconds, 2 seconds, 1 second, 0.9 seconds, 0.8 seconds, 0.7 seconds, 0.6 seconds, 0.5 seconds, 0.4 seconds, 0.3 seconds, 0.2 seconds, 0.1 seconds, or less, at least about 0.1 seconds, 0.2 seconds, 0.3 seconds, 0.4 seconds, 0.5 seconds, 0.6 seconds, 0.7 seconds, 0.8 seconds, 0.9 seconds, 1 seconds, 2 seconds, 3 seconds, 4 seconds, 5 seconds, or more or within a range defined by any two of the preceding values.

In some embodiments, modulation of the amplitude of the magnetic field includes varying the magnetic field amplitude monotonically (or monotonically over each of a limited number of interval—such as one to ten increasing interval and/or one to ten decreasing intervals). In some embodiments, the modulation of the amplitude of the magnetic field comprises linearly varying the amplitude of the magnetic field. The initial magnetic field amplitude of the sweep, the end magnetic field amplitude and the total duration of the sweep can be optimized for the target molecule. In some embodiments the magnetic field amplitude during the sweep is within a lower bound and an upper bound. The lower bound can be at least about $-2\ \mu T$, $-1\ \mu T$, $-0.9\ \mu T$, $-0.8\ \mu T$, $-0.7\ \mu T$, $-0.6\ \mu T$, $-0.5\ \mu T$, $-0.4\ \mu T$, $-0.3\ \mu T$, $-0.2\ \mu T$, $-0.1\ \mu T$, or more, at most about $-0.1\ \mu T$, $-0.2\ \mu T$, $-0.3\ \mu T$, $-0.4\ \mu T$, $-0.5\ \mu T$, $-0.6\ \mu T$, $-0.7\ \mu T$, $-0.8\ \mu T$, $-0.9\ \mu T$, $-1\ \mu T$, $-2\ \mu T$, or less, or within a range defined by any two of the preceding values. The upper bound can be at least about $0.1\ \mu T$, $0.2\ \mu T$, $0.3\ \mu T$, $0.4\ \mu T$, $0.5\ \mu T$, $0.6\ \mu T$, $0.7\ \mu T$, $0.8\ \mu T$, $0.9\ \mu T$, $1\ \mu T$, $2\ \mu T$, or more, at most about $2\ \mu T$, $1\ \mu T$, $0.9\ \mu T$, $0.8\ \mu T$, $0.7\ \mu T$, $0.6\ \mu T$, $0.5\ \mu T$, $0.4\ \mu T$, $0.3\ \mu T$, $0.2\ \mu T$, $0.1\ \mu T$, or less, or within a range defined by any two of the preceding values. In some embodiments the duration of modulation can be at least about 100 ms, 200 ms, 300 ms, 400 ms, 500 ms, 600 ms, 700 ms, 800 ms, 900 ms, 1,000 ms, 2,000 ms, 3,000 ms, 4,000 ms, 5,000 ms, 6,000 ms, 7,000 ms, 8,000 ms, 9,000 ms, 10,000 ms, or more, at most about 10,000 ms, 9,000 ms, 8,000 ms, 7,000 ms, 6,000 ms, 5,000 ms, 4,000 ms, 3,000 ms, 2,000 ms, 1,000 ms, 900 ms, 800 ms, 700 ms, 600 ms, 500 ms, 400 ms, 300 ms, 200 ms, 100 ms, or less, or within a range defined by any two of the preceding values. In some embodiments, the rate of amplitude change is varied along the amplitude profile. In some embodiments, a constant-adiabaticity sweep is calculated by choosing a certain subset of level avoided crossings of the spin system. In some embodiments, the magnetic amplitude modulation includes a combination of diabatic jumps, monotonous amplitude modulation and rate of change sign reversals.

Purification and Separation

In some embodiments, the precursor may be chosen or designed such that following the hydrogenation and other potential chemical reactions, one of the products is a biorelevant imaging agent usable in hyperpolarized NMR or MRI applications. In some embodiments, the biorelevant imaging agent is produced through additional chemical reactions following hydrogenation. Such additional chemical reactions may include cleaving of a sidearm of the molecule (e.g., cleavage of the compound of Formula II, as described herein) to form the biorelevant imaging agent and a sidearm (e.g., a compound of Formula III described herein), e.g., by hydrolysis. Following hydrogenation and polarization transfer, the parahydrogenated precursor (e.g., a compound of Formula II, as described herein) may be cleaved to produce the hyperpolarized biorelevant imaging agent.

The volume of the solution which includes the biorelevant imaging agent, following cleavage (and concentration of the biorelevant imaging agent produced) can depend on the volume of the solution used for polarization transfer and concentration of the precursor in that solution. Exemplary ranges of solution volumes and precursor concentrations are described herein. As further specific examples, at least about 1 ml, 2 ml, 3 ml, 4 ml, 5 ml, 6 ml, 7 ml, 8 ml, 9 ml, 10 ml, or more of solution including at least about 10 mM, 20 mM, 30 mM, 40 mM, 50 mM, 60 mM, 70 mM, 80 mM, 90 mM, 100 mM, 200 mM, 300 mM, 400 mM, 500 mM, or more of the biorelevant imaging agent can be produced.

Consistent with disclosed embodiments, following polarization transfer and cleaving of the precursor to generate the hyperpolarized biorelevant imaging agent, the properties of the solution containing the hyperpolarized biorelevant imaging agent can be modified to induce precipitation of the hyperpolarized biorelevant imaging agent.

Such precipitation can enable separation of the hyperpolarized biorelevant imaging agent from other substances in the solution (e.g., sidearm fragments). The precipitate can form crystals, amorphous solid particles, polycrystal material, or the like. Following the precipitation, at least a fraction of the solid hyperpolarized biorelevant imaging agents (or the hyperpolarized precursor) can be separated from the solution and other substances in the solution. For example, a mixture of the precipitate and solution can be filtered to remove the particles. The filtered precipitate can be washed using a second solvent. The second solvent can be selected to remove residue of the original solvent and the other substances in the solution without fully dissolving the filtered precipitate. In some embodiments the washing step occurs in at most about 300 seconds, 200 seconds, 100 seconds, 90 seconds, 80 seconds, 70 seconds, 60 seconds, 50 seconds, 30 seconds, 20 seconds, 10 seconds, in at least about 10 seconds, 20 seconds, 30 seconds, 50 seconds, 60 seconds, 70 seconds, 80 seconds, 90 seconds, 100 seconds, 200 seconds, 300 seconds, or more, or in a period of time that is within a range defined by any two of the preceding values.

Precipitation can be performed using an aqueous solution or a solution including an organic solvent, such as acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphoroustriamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, water, heavy water, o-xylene, m-xylene, p-xylene. In some embodiments, an organic solvent is used for polarization and precipitation steps. For example, parahydrogen may be more soluble in a range of organic solvents than in an aqueous solution. Thus, hydrogenation can occur more efficiently in such solvents. Accordingly, PHIP can occur in a solution formed with an organic solvent. In some embodiments, an aqueous solution is used for hydrogenation and the polarization transfer. In some embodiments, the aqueous solution can be mixed with a miscible organic solvent before precipitation of the hyperpolarized biorelevant imaging agent.

In some embodiments, precipitation of the biorelevant imaging agent is induced by changing the pH of the solvent. In organic solvents, certain biorelevant imaging agents (e.g., carboxylic acids, pyridine, and the like) can be soluble in concentrations suitable for polarization using PHIP. However, salts of these biorelevant imaging agents can be very insoluble. For example, such salts may be insoluble at concentrations of at most about 10 mM, 9 mM, 8 mM, 7 mM, 6 mM, 5 mM, 4 mM, 3 mM, 2 mM, 1 mM, 1 mM, 0.9 mM, 0.8 mM, 0.7 mM, 0.6 mM, 0.5 mM, 0.4 mM, 0.3 mM, 0.2 mM, 0.1 mM, 0.09 mM, 0.08 mM, 0.07 mM, 0.06 mM, 0.05 mM, 0.04 mM, 0.03 mM, 0.02 mM, 0.01 mM, or less, at least about 0.01 mM, 0.02 mM, 0.03 mM, 0.04 mM, 0.05 mM, 0.06 mM, 0.07 mM, 0.08 mM, 0.09 mM, 0.1 mM, 0.2 mM, 0.3 mM, 0.04 mM, 0.05 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, or more, or concentrations that are within a range defined by any two of the preceding values. An organic solution can contain a biorelevant imaging agent in a concentration suitable for hyperpolarization using PHIP. Following polarization, the pH of the organic solution can be changed to induce precipitation of the salt of the biorelevant imaging agent. In aqueous solutions, the salt of certain biorelevant imaging agents (e.g., fumarate, glutamate, and the like) is more soluble than the acidic form. Thus, an aqueous solution can contain a biorelevant imaging agent in a concentration suitable for hyperpolarization using PHIP. Following polarization, the pH of the aqueous solution can be lowered to induce precipitation of the acidic form of the biorelevant imaging agent.

Consistent with disclosed embodiments, the change of pH can be induced by addition of an acidic or a basic molecule to the solution, such as sodium chloride or sodium hydroxide. In some embodiments, the change of pH can be induced by mixing the solution with another solution that has a substantially different pH. In some embodiments the precipitation due to change of pH occurs in at most about 100 seconds, 90 seconds, 80 seconds, 70 seconds, 60 seconds, 50 seconds, 40 seconds, 30 seconds, 20 seconds, 10 seconds, 9 seconds, 8 seconds, 7 seconds, 6 seconds, 5 seconds, 4 seconds, 3 seconds, 2 second, 1 second, or less, at least about 1 second, 2 seconds, 3 seconds, 4 seconds, 5 seconds, 6 seconds, 7 seconds, 8 seconds, 9 seconds, 10 second, 20 seconds, 30 seconds, 40 seconds, 50 seconds, 60 seconds, 70 seconds, 80 seconds, 90 seconds, 100 seconds, or more, or in a period of time that is within a range defined by any two of the preceding values.

In some embodiments, precipitation of the biorelevant imaging agent is induced without changing the pH of the solution of inducing the hyperpolarized biorelevant imaging agent to change between a salt and an acid form.

In some embodiments, hydrogenation and polarization transfer occurs in a first solution having a first solvent. The biorelevant imaging agent may have a high solubility in the first solvent. Precipitation can be induced by mixing the first solution with a second solvent to form a second solution. The second solvent can be chosen such that the solubility of the biorelevant imaging agent in the second solution is low enough to initiate precipitation.

In some embodiments, the temperature of the solution is changed, thereby lowering the solubility of the hyperpolarized molecules and initiating precipitation. In most solvents the solubility decreases as the temperature decreases. The change in temperature to the desired temperature with the lower solubility may be performed within at most about 100 seconds, 90 seconds, 80 seconds, 70 seconds, 60 seconds, 50 seconds, 40 seconds, 30 seconds, 20 seconds, 10 seconds, 9 seconds, 8 seconds, 7 seconds, 6 seconds, 5 seconds, 4 seconds, 3 seconds, 2 second, 1 second, or less, at least about 1 second, 2 seconds, 3 seconds, 4 seconds, 5 seconds, 6 seconds, 7 seconds, 8 seconds, 9 seconds, 10 second, 20 seconds, 30 seconds, 40 seconds, 50 seconds, 60 seconds, 70 seconds, 80 seconds, 90 seconds, 100 seconds, or more, or in a period of time that is within a range defined by any two of the preceding values. For example, the maximal mole fraction of acetic acid in n-heptane is 0.935 at 14.8° C., only 0.02 at −29.2° C. and lower at even colder temperatures. The selected temperature for precipitation can be selected as a temperature above the freezing point of the solvent.

In some embodiments, the surface area of the solution is increased to induce nucleation of the precipitate. This can be achieved for example by spraying the solution through a nozzle to create very small droplets with a high surface area.

In some embodiments, microcrystal seeds (which may be of the biorelevant imaging agent, or another biocompatible compound) are added to the solution to induce precipitation.

In some embodiments, the pressure of the solution is changed, thereby lowering the solubility of the hyperpolarized compounds and initiating precipitation.

In some embodiments, the concentration of the hyperpolarized biorelevant imaging agent is raised above its solubility limit, thereby inducing precipitation without lowering the compound solubility level in the solvent. This can be achieved for example by adding unpolarized molecules of the biorelevant imaging agent or by evaporating a certain volume of the solvent, thereby increasing the concentration of the biorelevant imaging agent above its solubility limit.

In some embodiments, the parameters for the PHIP polarization are optimized for a high concentration, such as above the solubility limit for the biorelevant imaging agent in its acid or salt form, even at the expense of achieving a lower polarization. This can be achieved, for example, by starting with a high concentration of the precursors for hydrogenation and choosing a long hydrogenation time, which can cause polarization to be lowered due to relaxation, to achieve a high biorelevant imaging agent concentration.

In some embodiments the precipitation is accelerated by the addition of mechanical energy or improved mixing of the mixture for a certain duration. This can be performed for example by applying ultrasonic waves on the mixture through an ultrasound solicitor, or by mechanical or magnetic mixing of the sample. In some embodiments, the additional mixing or introduction of mechanical energy is performed for at least about 0.1 seconds, 0.2 seconds, 0.3 seconds, 0.4 seconds, 0.5 seconds, 0.6 seconds, 0.7 seconds, 0.8 seconds, 0.9 seconds, 1 second, 2 seconds, 3 seconds, 4 seconds, 5 seconds, 6 seconds, 7 seconds, 8 seconds, 9 seconds, 10 seconds, or more, at most about 10 seconds, 9 seconds, 8 seconds, 7 seconds, 6 seconds, 5 seconds, 4 seconds, 3 seconds, 2 seconds, 1 second, 0.9 seconds, 0.8 seconds, 0.7 seconds, 0.6 seconds, 0.5 seconds, 0.4 seconds, 0.3 seconds, 0.2 seconds, 0.1 seconds, or less, or for a period of time that is within a range defined by any two of the preceding values.

In some embodiments, precipitation is induced by a chemical reaction involving a hyperpolarized biorelevant imaging agent. The hyperpolarized biorelevant imaging agent can react with another compound or in response to an external stimulus such as electromagnetic radiation (e.g., ultraviolet irradiation). The product of this reaction may have a reduced solubility in comparison to the hyperpolarized biorelevant imaging agent, thereby inducing the precipitation. For example, the external stimulus can modify a structure of the hyperpolarized biorelevant imaging agent, thereby reducing the solubility of the hyperpolarized biorelevant imaging agent. Following redissolution of the precipitate, additional reactions can be performed to produce a desired final product (e.g., a biorelevant imaging agent, NMR material, or the like).

In some embodiments, a hydrolysis of the precursor induces the precipitation. In some embodiments, a solvent is selected such that the precursor is more soluble than the biorelevant imaging agent. The concentration of the precursor in the solution can be selected such that, following cleavage of the sidearm and generation of the biorelevant imaging agent, the biorelevant imaging agent precipitates out of the solution. In some such embodiments, the cleavage is initiated by changing the pH of the solution. For example, the cleavage can be initiated by adding a base (e.g., sodium hydroxide or another suitable base). In some embodiments, the solution is formed with an organic solvent and the cleavage can be performed under basic conditions. Following the cleavage, the less soluble biorelevant imaging agent undergoes rapid precipitation while preserving its polarization. The same solution can be used for hydrogenation, polarization transfer, and precipitation, or another solvent can be mixed into the solution used for hydrogenation and polarization transfer.

In some embodiments, the precipitation of the precursor occurs before cleavage. Such embodiments may be suitable when the precursor is more stable than the biorelevant imaging agent. Precipitation of the precursor can be induced by modifying the pH of the solution such that the solubility of the precursor is reduced, or by mixing in a solution or compound which lowers the solubility of the precursor. In such embodiments, cleavage of the precursor can be performed after re-dissolution of the precursor in a solvent. The precursor can be filtered and washed as described herein to remove other substances present in the original solution, such as hydrogenation catalysts. The precursor can then be reacted (e.g., by cleaving a sidearm) to form the biorelevant imaging agent. The biorelevant imaging agent can be separated from other reaction products by liquid-liquid extraction or by an additional precipitation step, consistent with the precipitation methods described herein. In some embodiments, precipitation can occur after generation of the biorelevant imaging agent from the precursor. Such precipitation can be performed according to the methods described herein.

In some embodiments, the conversion of spin order to polarization occurs before the compounds are made to solidify and precipitate. In other embodiments, the conversion happens after re-dissolution of the crystals with the biorelevant imaging agents.

In some embodiments, several steps of precipitation, washing and redissolution are performed. This can be advantageous in further purifying the biorelevant imaging agents, increasing the relaxation time of the precipitate or further separating the polarization and cleavage steps. For example, the first precipitation can be used for washing out the catalyst, while the second precipitation is of a crystal form with a longer relaxation time, and which can be used for transport. In some embodiments, the first precipitation is of a compound of the Formula II, following hydrogenation and polarization transfer, and the second precipitation is performed after the cleavage.

Consistent with disclosed embodiments, steps of precipitation (and optionally washing) can separate the hyperpolarized biorelevant imaging agent from other substances in the original solution (e.g., catalysts, the original solvent(s), reaction products, or the like). For example, most of the hydrogenation catalyst present in the original solution can be retained in the original solution following precipitation of the biorelevant imaging agent. In some embodiments, the precipitate (optionally following washing) can retain at most about 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, or less of the hydrogenation catalyst, at least about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, or more of the hydrogenation catalyst, or an amount of the hydrogenation catalyst that is within a range defined by any two of the preceding values. Similarly, the precipitate can retain at most about 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, or less of the cleavage byproducts (e.g., the sidearm or other residues of the cleavage), at least about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 10%, or more of the cleavage byproducts, or an amount of the cleavage byproducts that is within a range defined by any two of the preceding values.

In some embodiments, following the precipitation and separation from the original solvent (and potentially transport of the hyperpolarized precipitate), the precipitate is redissolved in a solvent (e.g., for use as an agent in hyperpolarized NMR or MRI). The solvent may be a biocompatible solvent, such as an aqueous solution. In some embodiments the redissolution is performed in at most about 60 seconds, 50 seconds, 40 seconds, 30 seconds, 20 seconds, 10 seconds, 9 seconds, 8 seconds, 7 seconds, 6 seconds, 5 seconds, 4 seconds, 3 seconds, 2 seconds, 1 second, or less, at least about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds, 60 seconds, or more, or in a period of time that is within a range defined by any two of the preceding values.

In some embodiments, following re-dissolution, the biorelevant imaging agent is present in a higher concentration than the concentration used during the PHIP polarization. In some embodiments the concentration of the hyperpolarized biorelevant imaging agent after re-dissolution is at least about 100 mM, 150 mM, 200 mM, 250 mM, 300 mM, 350 mM, 400 mM, 450 mM, 500 mM, or more, at most about 500 mM, 450 mM, 400 mM, 350 mM, 300 mM, 250 mM, 200 mM, 150 mM, 100 mM, or less, or within a range defined by any two of the preceding values. Thus, the concentration of the precursor or biorelevant imaging agent during polarization can be independent of the concentration of the molecules in the injection solution. The concentration of the precursor or biorelevant imaging agent during polarization can be selected for efficient polarization transfer. In some embodiments, this polarization concentration is less than the concentration of the hyperpolarized biorelevant imaging agent after re-dissolution. For example, the polarization concentration can be at least about 300 mM, 200 mM, 150 mM, 140 mM, 130 mM, 120 mM, 110 mM, 100 mM, 90 mM, 80 mM, 70 mM, 60 mM, 50 mM, 40 mM, 30 mM, 20 mM, 10 mM, or less, or most about 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 200 mM, 300 mM, or more, or within a range defined by any two of the preceding values.

In some embodiments, samples of the precipitate exhibit polarization of at least about 1%, 2%3, 3%, 4%, 5%, 6%, 7%, 8%, 9%, 10%, 15%, 20%, 25%, 30%, 40%, 45%, 50%, more, at most about 50%, 45%, 40%, 35%, 30%, 25%, 20%, 15%, 10%, 9%, 8%, 7%, 6%, 5%, 4%, 3%, 2%, 1%, or less, or polarization that is within a range defined by any two of the preceding values. For example, in some embodiments, samples of the precipitate exhibit polarization between 10% and 15%, between 10% and 20%, between 10% and 25%, between 10% and 30%, between 10% and 35%, between 10% and 40%, between 10% and 45%, between 10% and 50%, between 15% and 20%, between 15% and 25%, between 15% and 30%, between 15% and 35%, between 15% and 40%, between 15% and 45%, between 15% and 50%, between 20% and 25%, between 20% and 30%, between 20% and 35%, between 20% and 40%, between 20% and 45%, between 20% and 50%, between 25% and 30%, between 25% and 35%, between 25% and 40%, between 25% and 45%, between 25% and 50%, between 30% and 35%, between 30% and 40%, between 30% and 45%, between 30% and 50%, between 35% and 40%, between 35% and 45%, between 35% and 50%, between 40% and 45%, between 40% and 50%, or between 45% and 50%.

Following re-dissolution of the particulate, the concentration of catalysts, the precursor, or cleavage byproducts may each be at most about 1 µM, 900 nanomolar (nM), 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, or less, at least about 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 µM, or more, or within a range defined by any two of the preceding values. In some embodiments, the purity of the hyperpolarized biorelevant imaging agent following redissolution is at least about 90% 91%, 92%, 93%, 94%, 95%, 96%, 97%, 98%, 99%, or more, at most about 99%, 98%, 97%, 96%, 95%, 94%, 93%, 92%, 91%, 90%, or less, or within a range defined by any two of the preceding values. In some embodiments, at least a fraction of the hyperpolarized compounds is separated from the cleaved sidearms, or other reaction byproducts, if such exist.

Transportation

Consistent with disclosed embodiments, polarization transfer and use of the biorelevant imaging agent can occur at different locations. In some embodiments, the precursor (in the solution used for polarization transfer or as a precipitate) is transported to another location following precipitation. In some embodiments, the biorelevant imaging agent (in the solution used for polarization transfer, as a precipitate, or redissolved) is transported to another location. The disclosed embodiments are not necessarily limited to any particular transport distance or duration. Instead, a maximum distance or duration can be determined based on the target molecule, the original degree or polarization, the required final degree of polarization, and the transport conditions. In some embodiments, the precipitate is transported at least one meter in a suitable transportation device.

Consistent with disclosed embodiments, a transportation device can be configured to transport samples of the precursor or biorelevant imaging agent. The transportation device can be arranged and configured for transporting one or more samples simultaneously. The transportation device can include a transport chamber configured to receive the one or more samples. The transportation device can be configured to maintain the transport chamber within a predetermined temperature range and a predetermined magnetic field strength. The transportation device can be configured to maintain the one or more samples in a magnetic field of at least about 10 G, 20 G, 30 G, 40 G, 50 G, 60 G, 70 G, 80 G, 90 G, 100 G, 200 G, 300 G, 400 G, 500 G, 600 G, 700 G, 800 G, 900 G, 1,000 G, or more, at most about 1,000 G, 900 G, 800 G, 700 G, 600 G, 500 G, 400 G, 300 G, 200 G, 100 G, 90 G, 80 G, 70 G, 60 G, 50 G, 40 G, 30 G, 20 G, 10 G, or less, or within a magnetic field that is within a range defined by any two of the previous values.

A permanent magnet or an electromagnet included in the transportation device can provide the magnetic field. In some embodiments, the permanent magnet or electromagnet is shielded to reduce the strength of the magnetic field outside the transportation device. The transportation device can also include a cooling system. The cooling system can be configured to maintain samples at a predetermined temperature or within a predetermined range of temperatures during transport. For example, the cooling system can be configured to maintain the samples at a temperature below 270 K, below 80 K, or below 4 K. In some embodiments, the transportation device is configured to maintain the samples at approximately the temperature of liquid nitrogen. The transportation device can include insulation between the cooling system and the exterior of the transportation device, to minimize heat exchange with the external environment. In some embodiments, the cooling system is configured to maintain the temperature of the samples using a cold gas flow. In some embodiments, the cooling system is configured to maintain the temperature of the samples using a liquid coolant. In some embodiments, the transportation device includes a Dewar to provide cooling of the samples. In order to distribute the hyperpolarized samples also across large distances, the container can be transported by standard transportation vehicles, such as planes, trains, trucks, cars and ships.

In some embodiments, the hyperpolarized precipitated particles are transported in the transportation device. In some embodiments the relaxation time of the hyperpolarized precipitated particles in the transportation device at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, or more, at most about 10 hours, 9 hours, 8 hours, 7 hours, 6 hours, 5 hours, 4 hours, 3 hours, 2 hours, 1 hour, 50 minutes, 40 minutes, 30 minutes, 20 minutes, 10 minutes, 9 minutes, 8 minutes, 7 minutes, 6 minutes, 5 minutes, 4 minutes, 3 minutes, 2 minutes, 1 minute, or less, or a relaxation time that is within a range defined by any two of the preceding values.

Generation of Polarized Biorelevant Imaging Agents

FIG. 1 depicts a first exemplary process 100 for generating polarized biorelevant imaging agents, in accordance with various embodiments. In the example shown, the process 100 comprises providing a composition comprising a compound of Formula I at step 110. In some embodiments, the compound of Formula I comprises: a Z group comprising: (i) a carbon-carbon double bond (—C═C—) which is substituted to include $^1$H (proton), $^2$H (deuterium), or a combination thereof or (ii) a carbon-carbon triple bond (—C≡C—), as described herein; an $R_1$ group comprising a PHIP transfer moiety descried herein; an $R_2$ group comprising an optionally substituted hydrocarbon, alkoxy group, primary amine, secondary amine, or tertiary amine, or a solubilizing moiety, as described herein; and an $R_3$ group comprising a biorelevant imaging agent, as described herein.

At step 120, the double bond or the triple bond in the compound of Formula I is hydrogenated with parahydrogen to form a parahydrogenated derivative of the compound of Formula I, wherein the parahydrogenated derivative is a compound having the structure of Formula II. In some embodiments, the compound of Formula II comprises: a Z' which is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*═CH*—) which is substituted to include $^1$H (proton), $^2$H (deuterium), or a combination thereof, wherein H* is a hydrogen having a spin order derived from parahydrogen; an $R_1$ group comprising a PHIP transfer moiety, as described herein; an $R_2$ group comprising an optionally substituted hydrocarbon, alkoxy group, primary amine, secondary amine, or tertiary amine, or a solubilizing moiety, as described herein; and an $R_3$ group comprising a biorelevant imaging agent, as described herein. In some embodiments, the compound of Formula I is hydrogenated with parahydrogen using a hydrogenation process described herein.

At step 130, a polarization transferring waveform is applied to transfer nuclear spin order from at least one H* in the sidearm of the compound of Formula II to any non-hydrogen nuclear spin in the biorelevant imaging agent of the compound of Formula II, as described herein, thereby forming a derivative of the compound of Formula II having a hyperpolarized biorelevant imaging agent. In some embodiments, the nuclear spin order is transferred using any polarization transfer process described herein.

Figure 2:
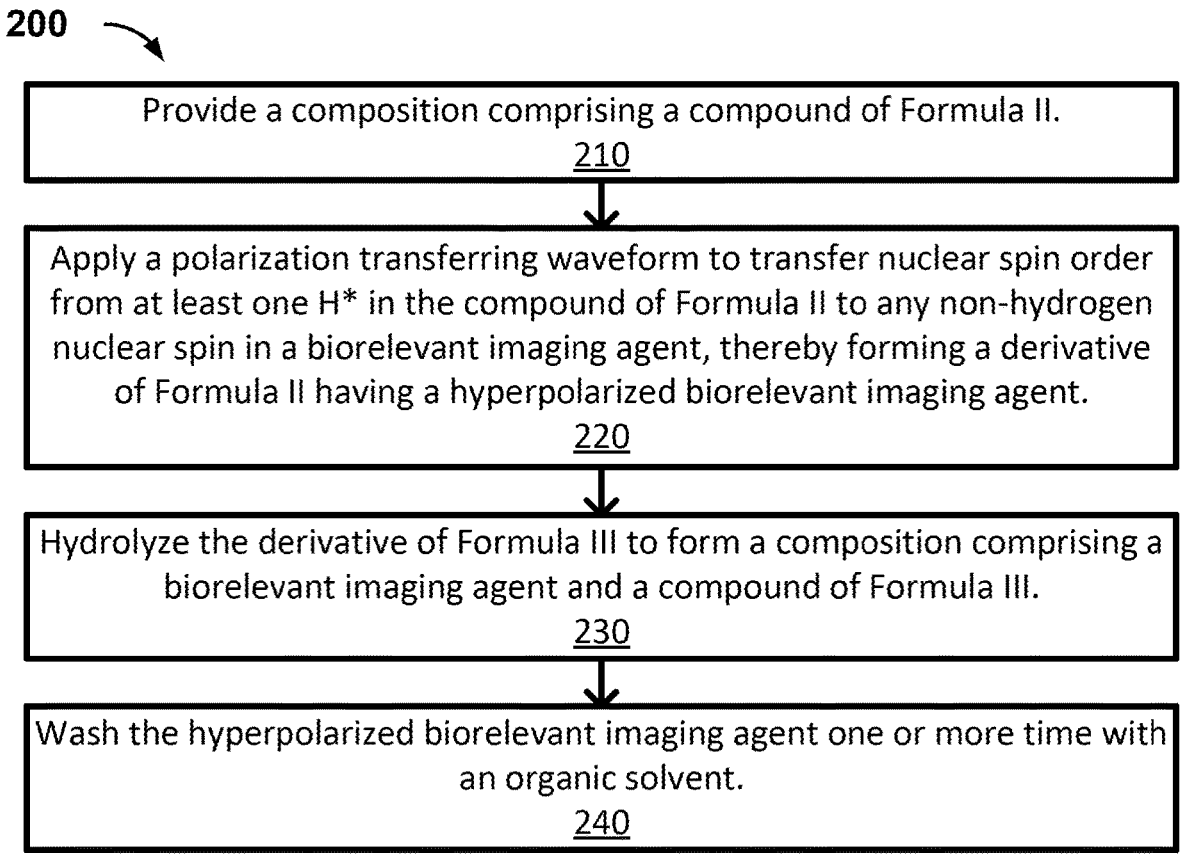
FIG. 2 depicts a second exemplary process for generating polarized biorelevant imaging agents, in accordance with various embodiments.

FIG. 2 depicts a second exemplary process 200 for generating polarized biorelevant imaging agents, in accordance with various embodiments of the present disclosure. In the example shown, the process 200 comprises providing a composition comprising a compound of Formula II at step 210. In some embodiments, Formula II comprises a Z' group which is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*═CH*—) which is substituted to include $^1$H (proton), $^2$H (deuterium), or a combination thereof, as described herein, wherein H* is a hydrogen having a spin order derived from parahydrogen; an $R_1$ group comprising a PHIP transfer moiety, as described herein; an $R_2$ group comprising an optionally substituted hydrocarbon, alkoxy group, primary amine, secondary amine, or tertiary amine, or a solubilizing moiety, as described herein; and an $R_3$ group comprising a biorelevant imaging agent, as described herein.

At step 220, a polarization transferring waveform is applied to the transfer nuclear spin order from at least one H* in the sidearm of the compound of Formula II to any non-hydrogen nuclear spin in the biorelevant imaging agent of the compound of Formula II, as descried herein, thereby forming a derivative of the compound of Formula II having a hyperpolarized biorelevant imaging agent.

At step 230, the derivative compound of Formula II is hydrolyzed to form a composition comprising a hyperpolarized biorelevant imaging agent and a separate sidearm compound of Formula III. In some embodiments, the compound of Formula III comprises a Z″ which is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*═CH*—) which is substituted to include $^1$H (proton), $^2$H (deuterium), or a combination thereof, as described herein; an $R_{1'}$ group comprising a parahydrogen induced polarization (PHIP) transfer moiety, as described herein; and an $R_2$ group comprising an optionally substituted hydrocarbon, alkoxy group, primary amine, secondary amine, or tertiary amine, or a solubilizing moiety, as described herein.

At step 240, the hyperpolarized biorelevant imaging agent is washed one or more times with an organic solvent. In some embodiments, the non-hydrogen nuclear spin in the biorelevant imaging agent has a non-hydrogen spin polarization after the washing step of at least about 1%, 2%, 3%, 4%, 5%, 6%, 7%, 8%, 9%, 10%, 15%, 20%, 25%, 30%, 35%, 40%, 45%, 50%, or more, at most about 50%, 45%, 40%, 35%, 30%, 25%, 20%, 15%, 10%, 9%, 8%, 7%, 6%, 5%, 4%, 3%, 2%, 1%, or less, or a non-hydrogen spin polarization that is within a range defined by any two of the preceding values.

In some embodiments, process 100 or process 200 comprises one or more additional steps or operations. In some embodiments, process 100 or process 200 omits one or more steps or operations. In some embodiments, one or more steps or operations of process 100 are combined with one or more steps or operations of process 200. In some embodiments, all steps or operations of process 100 and process 200 are combined to yield a complete process for generating a hyperpolarized imaging agent from a precursor having the structure of Formula I.

Enumerated Embodiments

Non-limiting embodiments of the foregoing disclosed herein include:

Embodiment 1. A composition comprising a compound of Formula (I):

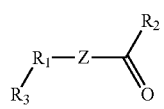

(I)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—); $R_1$ comprises a parahydrogen induced polarization (PHIP) transfer moiety; $R_2$ comprises an optionally substituted hydrocarbon, alkoxy group, primary amine, secondary amine, or tertiary amine; and $R_3$ comprises a biorelevant imaging agent comprising a non-hydrogen nuclear spin.

Embodiment 2. A composition comprising a compound of Formula (II):

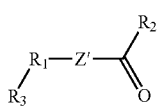

(II)

wherein Z' is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; wherein H* is a hydrogen having a spin order derived from parahydrogen; $R_1$ comprises a parahydrogen induced polarization (PHIP) transfer moiety; $R_2$ comprises an optionally substituted hydrocarbon, alkoxy group, primary amine, secondary amine, or tertiary amine; and $R_3$ comprises a biorelevant imaging agent comprising a non-hydrogen nuclear spin.

Embodiment 3. A composition comprising: (i) biorelevant imaging agent comprising a non-hydrogen nuclear spin; and (ii) a compound of Formula (III):

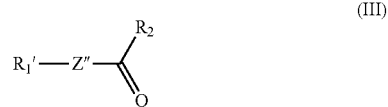

(III)

wherein Z" is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; $R_{1'}$ comprises a parahydrogen induced polarization (PHIP) transfer moiety; and $R_2$ comprises an optionally substituted hydrocarbon, alkoxy group, primary amine, secondary amine, or tertiary amine.

Embodiment 4. A composition comprising: (i) hyperpolarized biorelevant imaging agent comprising a non-hydrogen nuclear spin; and (ii) a compound of Formula (IV):

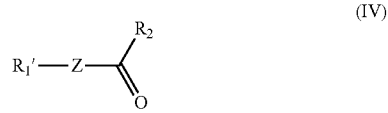

(IV)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—); $R_{1'}$ comprises a parahydrogen induced polarization (PHIP) transfer moiety; $R_2$ comprises an optionally substituted hydrocarbon, alkoxy group, primary amine, secondary amine, or tertiary amine.

Embodiment 5. The composition of any one of Embodiments 1 to 4, wherein the PHIP transfer moiety comprises an optionally substituted C1 hydrocarbon or an optionally substituted C2 hydrocarbon.

Embodiment 6. The composition of any one of Embodiments 1-5, wherein the PHIP transfer moiety comprises *$CR_4R_5$, *$CR_4Y$, *C=Y, or any deuterated version thereof, wherein: *C is a $^{12}$C or $^{13}$C carbon isotope; $R_4$ and $R_5$ are each independently selected from: $^1$H, $^2$H, $^3$H, a linear, branched, or cyclic C1-C10 alkyl hydrocarbon, a C6 aryl, a benzyl, a phenyl, a heteroaryl, and a haloalkyl group; and Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group.

Embodiment 7. The composition of any one of Embodiments 1-5, wherein the PHIP transfer moiety comprises *$CR_6R_7$—*$CR_8R_9$, or any deuterated version thereof, wherein: *C is a $^{12}$C or $^{13}$C carbon isotope; and $R_6$, $R_7$, $R_8$, and $R_9$ are each independently selected from: $^1$H, $^2$H, $^3$H, a linear, branched, or cyclic C1-C10 alkyl hydrocarbon, a C6 aryl, a benzyl, a phenyl, a heteroaryl, and a haloalkyl group.

Embodiment 8. The composition of any one of Embodiments 1 to 5, wherein the PHIP transfer moiety comprises *CH$_2$, *CH$_2$—*CH$_2$, *CHY, *C=Y, or any deuterated version thereof, wherein: *C is a $^{12}$C or $^{13}$C carbon isotope; and Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group.

Embodiment 9. The composition of Embodiment 6 or Embodiment 8, wherein the spin-1/2 atom is chosen from: $^1$H, $^{13}$C $^{15}$N, $^{19}$F, or $^{31}$P.

Embodiment 10. The composition of any one of Embodiments 1 to 9, wherein the PHIP transfer moiety includes at least one atom having a J-coupling with the non-hydrogen nuclear spin of at least 0.1 Hertz (Hz).

Embodiment 11. The composition of any one of Embodiments 1 to 10, wherein Z includes at least one atom having a J-coupling with the non-hydrogen nuclear spin of at least 0.1 Hertz (Hz).

Embodiment 12. The composition of any one of Embodiments 1 to 11, wherein R$_2$ comprises a solubilizing moiety.

Embodiment 13. The composition of any one of Embodiments 1 to 12, wherein R$_2$ comprises a hydrophobic and/or organophilic moiety.

Embodiment 14. The composition of Embodiment 13, wherein R$_2$ comprises an organic solubilizing moiety.

Embodiment 15. The composition of any one of Embodiments 1 to 12, wherein R$_2$ comprises a hydrophilic and/or organophobic moiety.

Embodiment 16. The composition of any one of Embodiments 1 to 15, wherein R$_2$ comprises, or is selected from: a methyl group, an ethyl group, a propyl group, an isopropyl group, an n-butyl group, an s-butyl group, a t-butyl group, an isobutyl group, a hydroxy group, a methyl alcohol group, an ethyl alcohol group, an n-propanol group, an isopropyl alcohol group a propionic alcohol group, an n-butyl alcohol group, an s-butyl alcohol group, a t-butyl alcohol group, an isobutyl alcohol group, a methoxy group, an ethoxy group, a propoxy group, an isopropxy, a propionic group, a butoxy group, a t-butoxy group, a s-butoxy group, an ester group, a phenyl group, a substituted phenyl group, a primary amine group, a secondary amine group, a tertiary amine group, a primary amide group, a secondary amide group, and a tertiary amide group.

Embodiment 17. The composition of any one of Embodiments 1 to 16, wherein the biorelevant imaging agent comprises a compound of the formula R$_{10}$C(=O)X—; wherein R$_{10}$ is chosen from a linear, branched, or cyclic C1-C10 alkyl group, in which one or more C atoms are optionally replaced with C=C, CO, COH, CNH$_2$, COOH, CH$_2$COOH, CONH$_2$, OC(=O); and X is chosen from NR$_{11}$, S and O; wherein R$_1$ is selected from $^1$H, $^2$H, $^3$H and an amino protecting group, optionally selected from trifluoroacetyl, acetyl, benzoyl, carbobenzoxy, tert-butyl carbonate and benzyl.

Embodiment 18. The composition of any one of Embodiments 1 to 17, wherein the biorelevant imaging agent is selected from: pyruvate, glutamate, glutamine, lactate, acetate, acetoacetate, zymonate, alanine, fructose, fumarate, bicarbonate, urea, dehydroascorbate, alpha-ketoglutarate, dihydroxyacetone, glucose, ascorbate, and conjugate acids thereof.

Embodiment 19. The composition of any one of Embodiments 1 to 18, wherein the composition has a solubility in water of less than 50 millimolar (mM).

Embodiment 19a. The composition of any one of Embodiments 1 to 18, wherein the composition has a solubility in an organic solvent (e.g., acetone, ethanol, chloroform, toluene) of less than 50 millimolar (mM).

Embodiment 20. The composition of any one of Embodiments 1 to 19a, wherein reacting the composition with parahydrogen results in a chemical yield of parahydrogenated product of at least 30%.

Embodiments 21. The composition of any one of Embodiments 1 to 20, for use in a parahydrogen induced polarization (PHIP) process.

Embodiment 22. A method for preparing a hyperpolarized biorelevant imaging agent or a pharmaceutically acceptable salt thereof, the method comprising: (a) providing a composition comprising a compound of Formula (I):

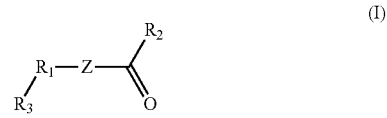

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—); R$_1$ comprises a parahydrogen induced polarization (PHIP) transfer moiety; R$_2$ comprises an optionally substituted hydrocarbon, alkoxy group, primary amine, secondary amine, or tertiary amine; and R$_3$ comprises a biorelevant imaging agent comprising a non-hydrogen nuclear spin; (b) hydrogenating the double bond or the triple bond in the compound of Formula I with parahydrogen to form a parahydrogenated derivative of the compound of Formula I, the parahydrogenated derivative having the structure of Formula (II):

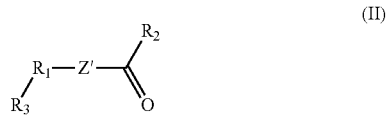

wherein Z' is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof, wherein H* is a hydrogen having a spin order derived from parahydrogen; R$_1$ comprises a parahydrogen induced polarization (PHIP) transfer moiety; R$_2$ comprises an optionally substituted hydrocarbon, alkoxy group, primary amine, secondary amine, or tertiary amine; and R$_3$ comprises a biorelevant imaging agent comprising a non-hydrogen nuclear spin; and (c) applying a polarization transferring waveform to transfer nuclear spin order from at least one H* in the compound of Formula II to the non-hydrogen nuclear spin, thereby forming a derivative of Formula II having a hyperpolarized biorelevant imaging agent.

Embodiment 23. A method for preparing a hyperpolarized biorelevant imaging agent or a pharmaceutically acceptable salt thereof, the method comprising: (a) providing a composition comprising a compound Formula (II):

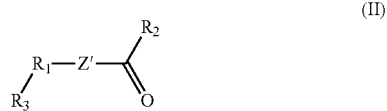

(II)

wherein Z' is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof, wherein H* is a hydrogen having a spin order derived from parahydrogen; $R_1$ comprises a parahydrogen induced polarization (PHIP) transfer moiety; $R_2$ comprises an optionally substituted hydrocarbon, alkoxy group, primary amine, secondary amine, or tertiary amine; and $R_3$ comprises a biorelevant imaging agent comprising a non-hydrogen nuclear spin; and (b) applying a polarization transferring waveform to transfer nuclear spin order from at least one H* in the compound of Formula II to the non-hydrogen nuclear spin, thereby forming a derivative of Formula II having a hyperpolarized biorelevant imaging agent.

Embodiment 24. The method of Embodiment 22 or Embodiment 23, further comprising hydrolyzing the derivative of Formula II to provide a composition comprising: (i) a hyperpolarized biorelevant imaging agent comprising a non-hydrogen nuclear spin; and (ii) a compound of Formula (III):

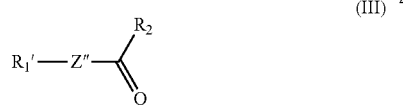

(III)

wherein Z" is: (i) a parahydrogenated carbon-carbon single bond (—CH*—CH*—) which is substituted to include $^1$H (proton), $^2$H (deuterium), or a combination thereof, or (ii) a parahydrogenated carbon-carbon double bond (—CH*=CH*—) which is substituted to include $^1$H (proton), $^2$H (deuterium), or a combination thereof; $R_{1'}$ comprises a parahydrogen induced polarization (PHIP) transfer moiety; and $R_2$ comprises an optionally substituted hydrocarbon, alkoxy group, primary amine, secondary amine, or tertiary amine.

Embodiment 25. The method of Embodiment 24, further comprising washing the hyperpolarized biorelevant imaging agent one or more times with an organic solvent.

Embodiment 26. The method of Embodiment claim 25, where the non-hydrogen nuclear spin has a non-hydrogen nuclear spin polarization above 10% after the washing step.

Embodiment 27. The method of any one of Embodiments 22 to 26, wherein the PHIP transfer moiety comprises an optionally substituted C1 hydrocarbon or an optionally substituted C2 hydrocarbon.

Embodiment 28. The method of any one of Embodiments 22 to 26, wherein the PHIP transfer moiety comprises *CR$_4$R$_5$, *CR$_4$Y, *C=Y, or any deuterated version thereof, wherein: *C is a $^{12}$C or $^{13}$C carbon isotope; R$_4$ and R$_5$ are each independently selected from: $^1$H, $^2$H, $^3$H, a linear, branched, or cyclic C1-C10 alkyl hydrocarbon, a C6 aryl, a benzyl, a phenyl, a heteroaryl, and a haloalkyl group; and Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group.

Embodiment 29. The method of any one of Embodiments 22 to 26, wherein the PHIP transfer moiety comprises *CR$_6$R$_7$—*CR$_8$R$_9$, or any deuterated version thereof, wherein: *C is a $^{12}$C or $^{13}$C carbon isotope; and R$_6$, R$_7$, R$_8$, and R$_9$ are each independently selected from: $^1$H, $^2$H, $^3$H, a linear, branched, or cyclic C1-C10 alkyl hydrocarbon, a C6 aryl, a benzyl, a phenyl, a heteroaryl, and a haloalkyl group.

Embodiment 30. The method of any one of Embodiments 22 to 26, wherein the PHIP transfer moiety comprises *CH$_2$, *CH$_2$—*CH$_2$, *CHY, *C=Y, or any deuterated version thereof, wherein: *C is a $^{12}$C or $^{13}$C carbon isotope; and Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom such as N, O, S, optionally substituted with a linear, branched, or cyclic C1-C10 alkyl hydrocarbon, a C6 aryl, benzyl, phenyl, heteroaryl, halogen or haloalkyl group.

Embodiment 31. The method of Embodiment 28 or Embodiment 30, wherein the spin-1/2 atom is chosen from: $^1$H, $^{13}$C $^{15}$N, $^{19}$F, or $^{31}$P.

Embodiment 32. The method of any one of Embodiments 22 to 31, wherein the PHIP transfer moiety includes at least one atom having a J-coupling with the non-hydrogen nuclear spin of at least 0.1 Hertz (Hz).

Embodiment 33. The method of any one of Embodiments 22 to 32, wherein Z or Z' includes at least one atom having a J-coupling with the non-hydrogen nuclear spin of at least 0.1 Hertz (Hz).

Embodiment 34. The method of any one of Embodiments 22 to 33, wherein R$_2$ comprises a solubilizing moiety.

Embodiment 35. The method of any one of Embodiments 22 to 34, wherein R$_2$ comprises a hydrophobic and/or organophilic moiety.

Embodiment 36. The method of Embodiment 35, wherein R$_2$ comprises an organic solubilizing moiety.

Embodiment 37. The method of any one of Embodiments 22 to 33, wherein R$_2$ comprises a hydrophilic and/or organophobic moiety Embodiment 38. The method of any one of Embodiments 22 to 37, wherein R$_2$ comprises, or is selected from: a methyl group, an ethyl group, a propyl group, an isopropyl group, an n-butyl group, an s-butyl group, a t-butyl group, an isobutyl group, a hydroxy group, a methyl alcohol group, an ethyl alcohol group, an n-propanol group, an isopropyl alcohol group a propionic alcohol group, an n-butyl alcohol group, an s-butyl alcohol group, a t-butyl alcohol group, an isobutyl alcohol group, a methoxy group, an ethoxy group, a propoxy group, an isopropxy, a propionic group, a butoxy group, a t-butoxy group, a s-butoxy group, an ester group, a phenyl group, a substituted phenyl group, a primary amine group, a secondary amine group, a tertiary amine group, a primary amide group, a secondary amide group, and a tertiary amide group.

Embodiment 39. The method of any one of Embodiments 22 to 38, wherein the biorelevant imaging agent comprises a compound of the formula $R_{10}C(=O)X-$; wherein $R_{10}$ is chosen from a linear, branched, or cyclic C1-C10 alkyl group, in which one or more C atoms are optionally replaced with $C=C$, CO, COH, $CNH_2$, COOH, $CH_2COOH$, $CONH_2$, $OC(=O)$; and X is chosen from $NR_{11}$, S and 0; wherein Rn is selected from $^1H$, $^2H$, $^3H$ and an amino protecting group, optionally selected from trifluoroacetyl, acetyl, benzoyl, carbobenzoxy, tert-butyl carbonate and benzyl.

Embodiment 40. The method of any one of Embodiments 22 to 39, wherein the biorelevant imaging agent is selected from pyruvate, glutamate, glutamine, lactate, acetate, acetoacetate, zymonate, alanine, fructose, fumarate, bicarbonate, urea, dehydroascorbate, alpha-ketoglutarate, dihydroxyacetone, glucose, ascorbate, and conjugate acids thereof.

Embodiment 41. A hyperpolarized biorelevant imaging agent or a pharmaceutically acceptable salt thereof, produced by the method of any one of Embodiments 22 to 40.

EXAMPLES

Example 1—NMR Procedures

NMR spectra were recorded on a Bruker Avance Neo 400 MHz spectrometer operating at 400.13 MHz for $^1H$ and 100.61 MHz for $^{13}C$. Trichloromethane ($CHCl_3$) was utilized as a solvent for $^1H$ NMR experiments, while deuterated trichloromethane ($CDCl_3$) was utilized as the solvent for $^{13}C$ NMR experiments. NMR chemical shifts (δ) are reported in ppm. For the $^1H$ and $^{13}C$ spectra the solvent signal was utilized for internal calibration [$^1H$ NMR: δ($CHCl_3$) 7.26; $^{13}C$ NMR: δ($CDCl_3$) 77.16]. $^{13}C$ NMR spectra were recorded in the proton-decoupled mode. Flash chromatography was carried out with a Biotage® Selekt Flash Purification System using a Biotage® Sfar HC Duo column as the solid phase and a mixture of cyclohexane and ethyl acetate as the mobile phase. Column chromatography was performed on silica gel (silica 60, 63-200 μm, Macherey-Nagel) using a mixture of cyclohexane and ethyl acetate as the mobile phase.

Example 2—General Synthetic Procedures

Synthesis of Esters with a,b-Unsaturated Sidearms

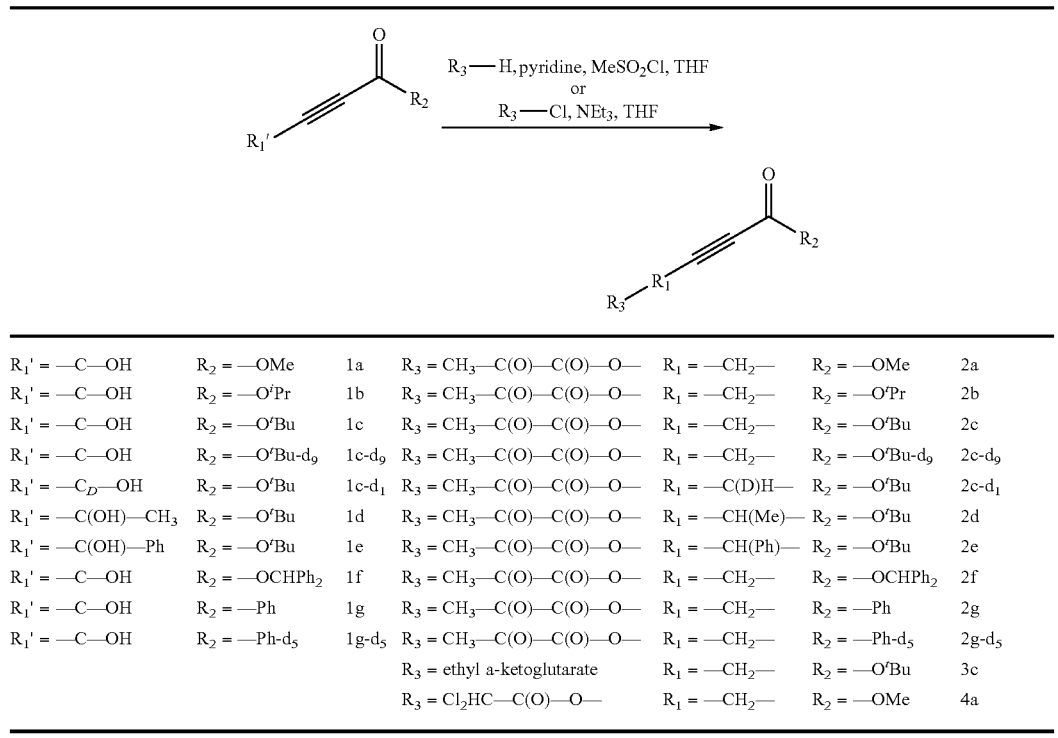

| $R_1'$ = —C—OH | $R_2$ = —OMe | 1a | $R_3$ = $CH_3$—C(O)—C(O)—O— | $R_1$ = —$CH_2$— | $R_2$ = —OMe | 2a |
| $R_1'$ = —C—OH | $R_2$ = —O$^i$Pr | 1b | $R_3$ = $CH_3$—C(O)—C(O)—O— | $R_1$ = —$CH_2$— | $R_2$ = —O$^i$Pr | 2b |
| $R_1'$ = —C—OH | $R_2$ = —O$^t$Bu | 1c | $R_3$ = $CH_3$—C(O)—C(O)—O— | $R_1$ = —$CH_2$— | $R_2$ = —O$^t$Bu | 2c |
| $R_1'$ = —C—OH | $R_2$ = —O$^t$Bu-$d_9$ | 1c-$d_9$ | $R_3$ = $CH_3$—C(O)—C(O)—O— | $R_1$ = —$CH_2$— | $R_2$ = —O$^t$Bu-$d_9$ | 2c-$d_9$ |
| $R_1'$ = —$C_D$—OH | $R_2$ = —O$^t$Bu | 1c-$d_1$ | $R_3$ = $CH_3$—C(O)—C(O)—O— | $R_1$ = —C(D)H— | $R_2$ = —O$^t$Bu | 2c-$d_1$ |
| $R_1'$ = —C(OH)—$CH_3$ | $R_2$ = —O$^t$Bu | 1d | $R_3$ = $CH_3$—C(O)—C(O)—O— | $R_1$ = —CH(Me)— | $R_2$ = —O$^t$Bu | 2d |
| $R_1'$ = —C(OH)—Ph | $R_2$ = —O$^t$Bu | 1e | $R_3$ = $CH_3$—C(O)—C(O)—O— | $R_1$ = —CH(Ph)— | $R_2$ = —O$^t$Bu | 2e |
| $R_1'$ = —C—OH | $R_2$ = —OCHPh$_2$ | 1f | $R_3$ = $CH_3$—C(O)—C(O)—O— | $R_1$ = —$CH_2$— | $R_2$ = —OCHPh$_2$ | 2f |
| $R_1'$ = —C—OH | $R_2$ = —Ph | 1g | $R_3$ = $CH_3$—C(O)—C(O)—O— | $R_1$ = —$CH_2$— | $R_2$ = —Ph | 2g |
| $R_1'$ = —C—OH | $R_2$ = —Ph-$d_5$ | 1g-$d_5$ | $R_3$ = $CH_3$—C(O)—C(O)—O— | $R_1$ = —$CH_2$— | $R_2$ = —Ph-$d_5$ | 2g-$d_5$ |
| | | | $R_3$ = ethyl a-ketoglutarate | $R_1$ = —$CH_2$— | $R_2$ = —O$^t$Bu | 3c |
| | | | $R_3$ = $Cl_2$HC—C(O)—O— | $R_1$ = —$CH_2$— | $R_2$ = —OMe | 4a |

Syntheses of Sidearms 1a-g

Alcohols 1a, 1c, 1d, and 1g were prepared in accordance with published procedures (1a: T. Yoshinao, K. Masanari, T. Shuji, K. Sigeru, Y. Zenichi, *Bull. Chem. Soc. Jpn.* 1994, 67, 2838-2849; 1c: B. R. Blank, I. P. Andrews, O. Kwon, *ChemCatChem* 2020, 12, 4352-4372; 1d: G. C. Tsui, K. Villeneuve, E. Carlson, W. Tam, *Organometallics* 2014, 33, 3847-3856; 1g: L. Pauli, R. Tannert, R. Scheil, A. Pfaltz, *Chem. Eur. J* 2015, 21, 1482-1487, each of which is incorporated herein by reference as related to methods for synthesizing Alcohols 1a, 1c, 1d, and 1g). Alcohol 1b was prepared starting from tetrahydro-2-(2-propynyloxy)-2H-pyran and isopropyl chloroformate by performing the procedure used to synthesize 1a followed by deprotection of the THP group with pyridinium p-toluenesulfonate. The synthesis of 1c-d$_9$ with a selective deuteration of the tert-butyl group was performed according to the synthesis of 1c with di-tert-butyl decarbonate-d18 substituted for di-tert-butyl decarbonate. Selective mono-deuteration in 1c-d$_1$ was performed by the followed reaction scheme:

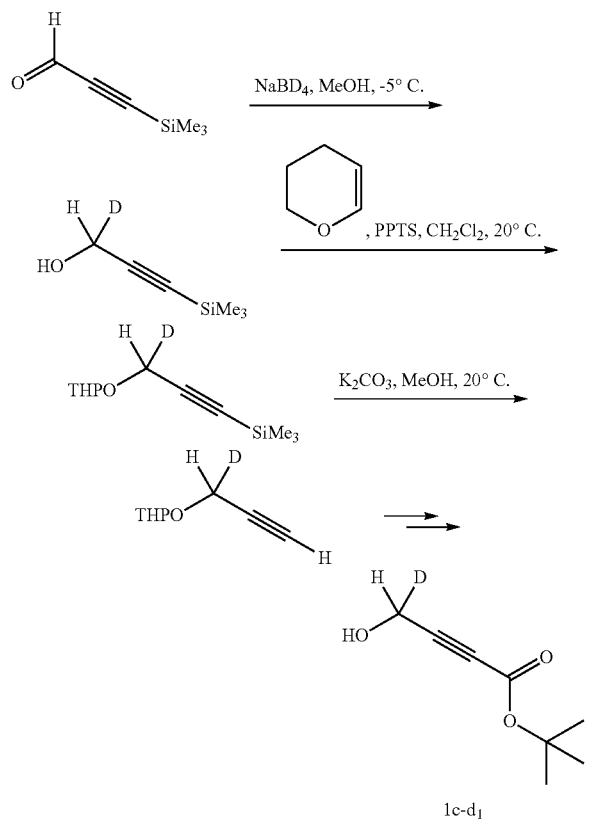

1c-d$_1$

Alcohol 1e was prepared in accordance with a published one-step synthesis from tert-butyl propiolate and benzaldehyde (A. Kondoh, R. Ozawa, M. Terada, *Chem. Lett.* 2019, 48, 1164-1167, which is incorporated herein by reference as related to methods for synthesizing Alcohols 1e). Alcohol 1f was prepared starting form tetrahydro-2-(2-propynyloxy)-2H-pyran via carboxylation using CO2 followed by the esterification with benzhyrol under Mitsunobu conditions according to literature known procedures (as described in O. Mitsunobu, Y. Yamada, *Bulletin Chem. Soc. Japan* 1967, 40(1), 2380-2382, which is incorporated herein by reference as related to methods for synthesizing Alcohols 1f) and THP-cleavage according to 1c. Alcohol 1g-d$_5$ was prepared according to 1g using benzoyl chloride-d$_5$ instead of benzoyl chloride.

Syntheses of Esters 2-4 with a,b-Unsaturated Sidearms

General Procedure A

The target carboxylic acid (1.0-2.0 equivalents) was dissolved in anhydrous tetrahydrofuran (THF, 200-350 millimolar), the corresponding alcohol 1a-g was added, and the solution was cooled to 0° C. with an ice/water bath. At this temperature, pyridine (4.0-5.0 equivalents) was added dropwise over a period of 5 minutes followed by the dropwise addition of methanesulfonyl chloride (1.2-2.0 equivalents) (or p-toluenesulfonyl chloride dissolved in THF) over a period of 10 minutes. The mixture was stirred until all of the corresponding alcohol 1a-g was consumed (monitored via $^1$H NMR, 2-5 hours at 0° C. if methanesulfonyl chloride and pyruvic acid were used in a high excess, up to 18 hours at ambient temperature if only a slight excess of methanesulfonyl chloride or p-toluenesulfonyl chloride was used). During the reaction, a colorless precipitate formed in all cases. After the reaction was completed, the reaction mixture was poured into a stirred mixture of aqueous 0.5 N HCl (same volume as solvent for the reaction) and diethyl ether (same volume as solvent for the reaction). The phases were separated, the organic phase was collected and the aqueous phase was washed with diethyl ether (2×200 mL). The combined organic phases were washed with saturated aqueous NaHCO$_3$ (100 mL) followed by washing with brine (100 mL). The organic phase was dried over Na$_2$SO$_4$, and the volatile components were removed under reduced pressure (800→1 mbar, 40° C. water bath). The crude product was purified via flash chromatography or by column chromatography.

General Procedure B

The corresponding alcohol 1a-g (1.0 equivalents) was dissolved in anhydrous THF (200 millimolar) and cooled to −78° C. with an acetone/dry-ice bath. To the clear mixture, anhydrous triethylamine (NEt$_3$, 1.0 equivalents) was added in one portion followed by the dropwise addition of the acid chloride of the target carboxylic acid (1.0 equivalents) over a period of 3 minutes. After complete addition of the acid chloride, the cooling bath was removed and the mixture was allowed to warm up to ambient temperature. The reaction was quenched by pouring the suspension into a stirred mixture of aqueous 0.5 N HCl (same volume as solvent for the reaction) and diethyl ether (same volume as solvent for the reaction). The phases were separated, the organic phase was collected, and the aqueous phase was washed with diethyl ether (2×200 mL). The combined organic phases were washed with saturated aqueous NaHCO$_3$ (100 mL) followed by washing with brine (100 mL). The organic phase was dried over Na$_2$SO$_4$, and the volatile components were removed under reduced pressure (800→1 mbar, 40° C. water bath). The crude product was purified via flash chromatography if necessary.

Example 3—Methyl 4-((2-oxopropanoyl)oxy)but-2-ynoate (2a)

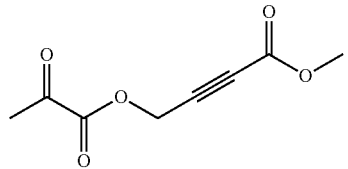

Structure 2a was prepared from alcohol 1a (7.08 grams (g), 62.1 millimole (mmol)), pyruvic acid (10.9 g, 124 mmol, 2.0 equivalents (eq.)), pyridine (25 mL, 310 mmol, 5.0 eq.) and methanesulfonyl chloride (9.6 mL, 124 mmol, 2.0 eq.) in THF (300 mL) for 4 hours (h) at 0° C. according to general procedure A. Purification was via column chromatography yielding 2a as a colorless, slightly viscous liquid (7.1 g, 38 mmol, 61% yield).

Figure 3A:
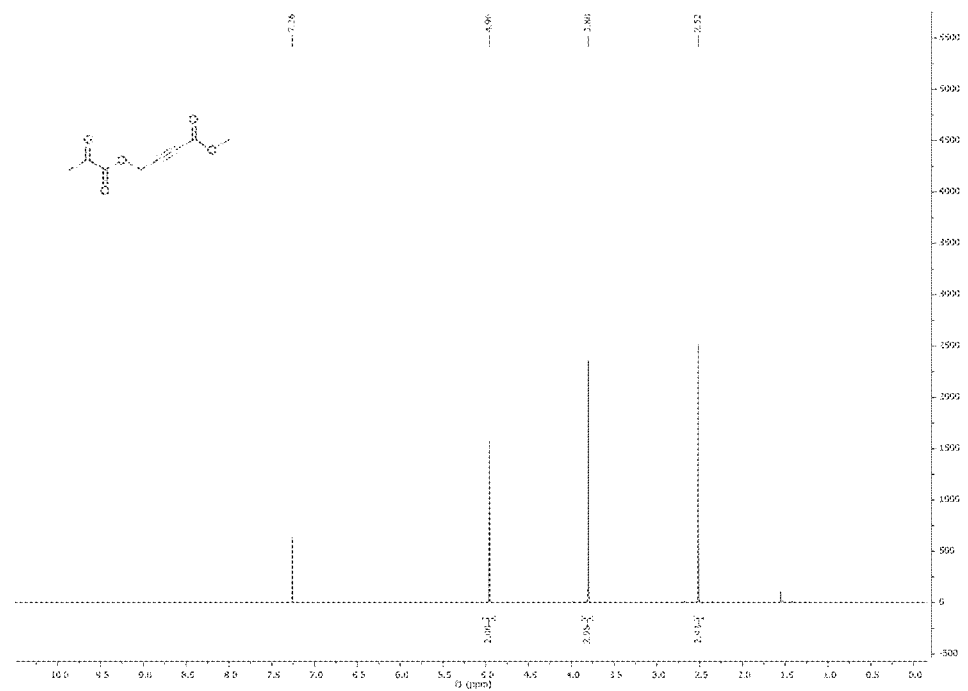
FIG. 3A shows an exemplary proton (H) nuclear magnetic resonance (NMR) spectrum corresponding to methyl 4-((2-oxopropanoyl)oxy)but-2-ynoate, in accordance with various embodiments.

FIG. 3A shows an exemplary $^1$H NMR (400 MHz, CDCl$_3$) spectrum corresponding to structure 2a. The spectrum displayed peaks at d=2.52 (singlet (s), integrated signal: 3H, corresponding to CH$_3$), 3.80 (s, 3H, OCH$_3$), and 4.96 (s, 2H, OCH$_2$).

Figure 3B:
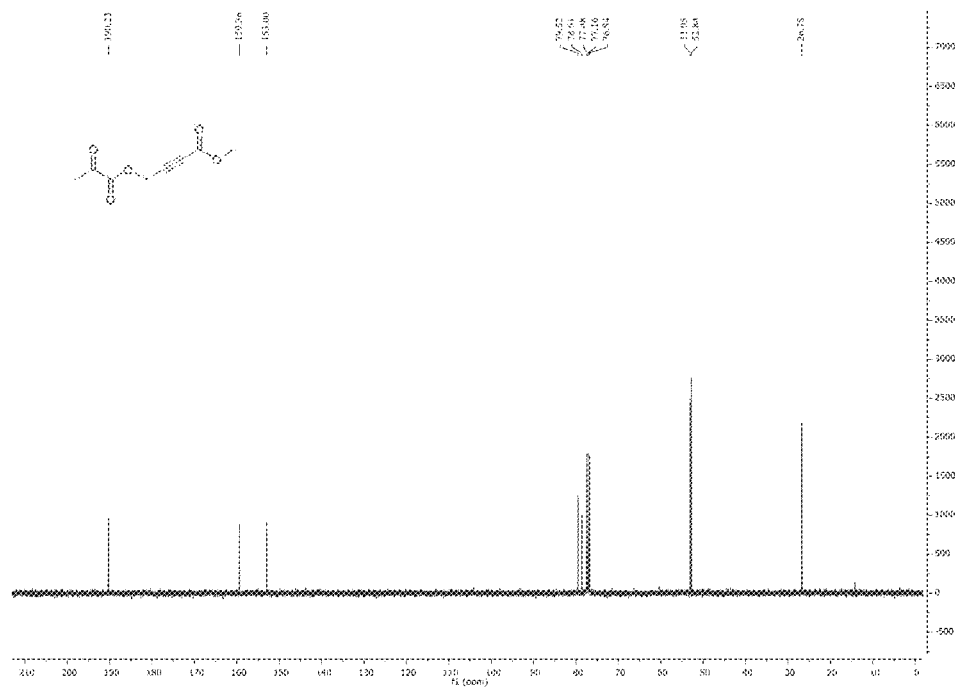
FIG. 3B shows an exemplary $^{13}$C NMR corresponding to methyl 4-((2-oxopropanoyl)oxy)but-2-ynoate, in accordance with various embodiments.

FIG. 3B shows an exemplary $^{13}$C NMR (101 MHz, CDCl$_3$) spectrum corresponding to structure 2a. The spectrum displayed peaks at d=26.78 (CH$_3$), 52.84 (OCH$_3$), 53.05 (OCH$_2$), 78.61 (C≡C), 79.52 (C≡C), 153.00 (COOCH$_3$), 159.36 (COO), and 190.23 (C=O).

Example 4—Isopropyl 4-((2-oxopropanoyl)oxy)but-2-ynoate (2b)

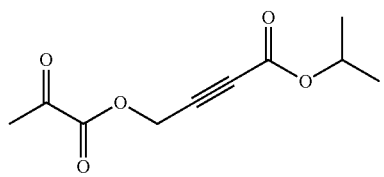

Structure 2b was prepared from alcohol 1b (6.36 g, 40.7 mmol), pyruvic acid (7.16 g, 81.4 mmol, 2.0 eq.), pyridine (16.4 mL, 203 mmol, 5.0 eq.) and p-toluenesulfonyl chloride (15.5 g, 81.4 mmol, 2.0 eq.) in THF (200 mL) for 2 h at 0° C. and 15 h at ambient temperature according to general procedure A. Purification was via flash chromatography yielding 2b as a yellowish, slightly viscous liquid (5.7 g, 25 mmol, 62% yield).

Figure 4A:
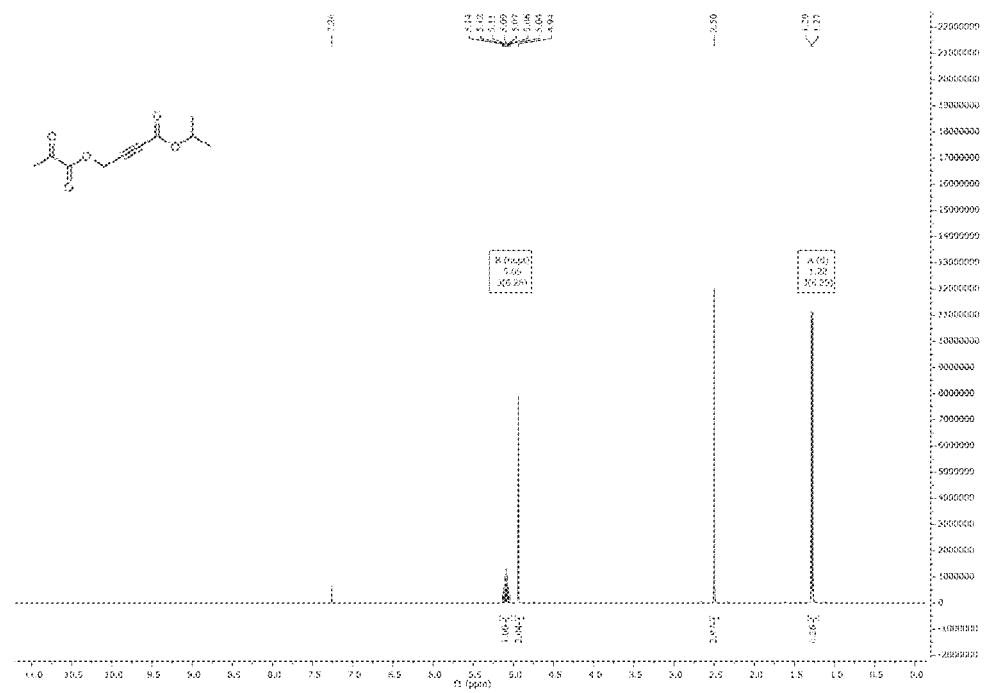
FIG. 4A shows an exemplary $^1$H NMR spectrum corresponding to isopropyl 4-((2-oxopropanoyl)oxy)but-2-ynoate, in accordance with various embodiments.

FIG. 4A shows an exemplary $^1$H NMR (400 MHz, CDCl$_3$) spectrum corresponding to structure 2b. The NMR spectrum displayed peaks at d=1.28 (doublet (d), $^3J_{H,H}$=6.29 Hz, 6H, 2×CH$_3$), 2.50 (s, 3H, CH$_3$), 4.94 (s, 2H, OCH$_2$), and 5.09 (heptet (hept), $^3J_{H,H}$=6.26 Hz, 1H, OCH).

Figure 4B:
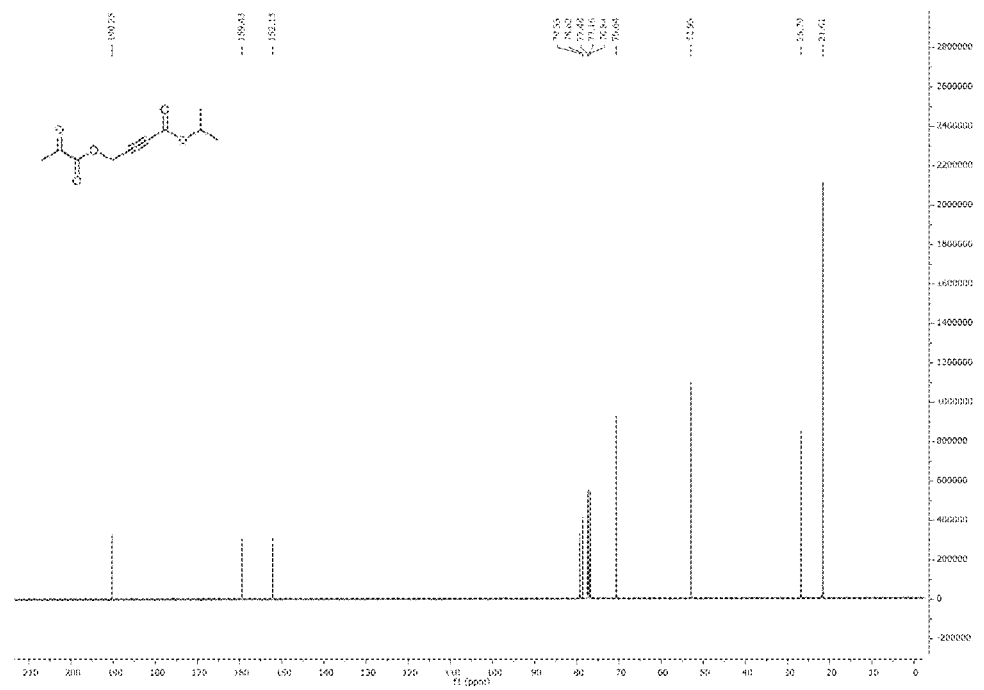
FIG. 4B shows an exemplary $^{13}$C NMR corresponding to Isopropyl 4-((2-oxopropanoyl)oxy)but-2-ynoate, in accordance with various embodiments.

FIG. 4B shows an exemplary $^{13}$C NMR (101 MHz, CDCl$_3$) spectrum corresponding to structure 2b. The NMR spectrum displayed peaks at d=21.61 (2×CH$_3$), 26.79 (CH$_3$), 52.93 (OCH$_2$), 70.64 (OCH), 78.62 (C≡C), 79.33 (C≡C), 152.15 (COO$^i$Bu), 159.43 (COO), and 190.25 (C=O).

Example 5—Tert-butyl 4-((2-oxopropanoyl)oxy)but-2-ynoate (2c)

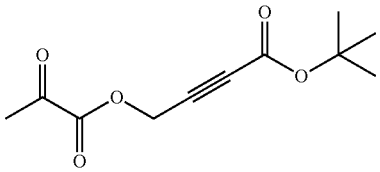 [SMILES: CC(=O)C(=O)OCC#CC(=O)OC(C)(C)C]

Structure 2c was prepared from alcohol 1c (30.0 g, 192 mmol), pyruvic acid (33.8 g, 384 mmol, 2.0 eq.), pyridine (77.0 mL, 954 mmol, 5.0 eq.) and methanesulfonyl chloride (30.0 mL, 388 mmol, 2.0 eq.) in THF (500 mL) for 3 h at 0° C. according to general procedure A. Purification was via flash chromatography yielding 2c as a yellowish, slightly viscous liquid (33 g, 146 mmol, 76% yield).

Figure 5A:
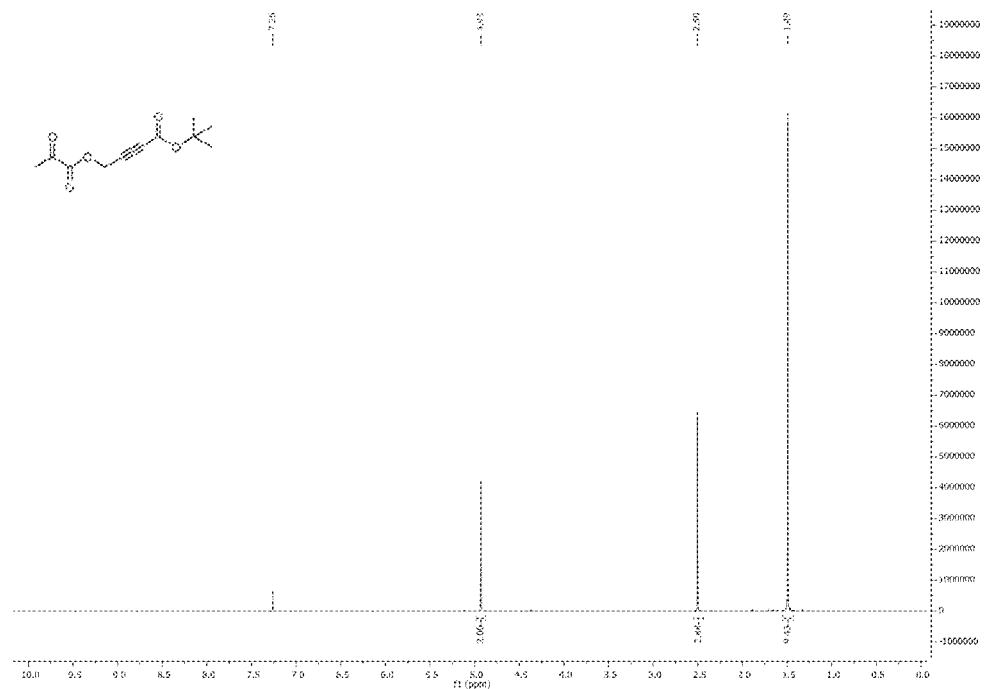
FIG. 5A shows an exemplary $^1$H NMR spectrum corresponding to tert-butyl 4-((2-oxopropanoyl)oxy)but-2-ynoate, in accordance with various embodiments.

FIG. 5A shows an exemplary $^1$H NMR (400 MHz, CDCl$_3$) spectrum corresponding to structure 2c. The NMR spectrum displayed peaks at d=1.49 (s, 9H, $^t$Bu), 2.50 (s, 3H, CH$_3$), and 4.93 (s, 2H, OCH$_2$).

Figure 5B:
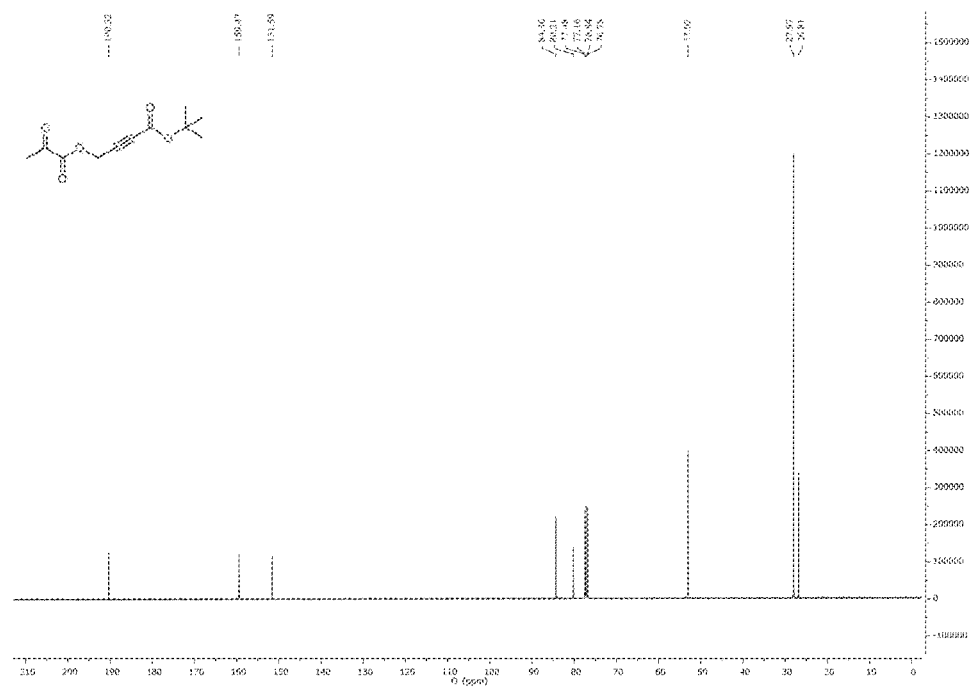
FIG. 5B shows an exemplary $^{13}$C NMR corresponding to tert-butyl 4-((2-oxopropanoyl)oxy)but-2-ynoate, in accordance with various embodiments.

FIG. 5B shows an exemplary $^{13}$C NMR (101 MHz, CDCl$_3$) spectrum corresponding to structure 2c. The NMR spectrum displayed peaks at d=26.81 (CH$_3$), 27.97 (3×CH$_3$), 53.02 (OCH$_2$), 76.78 (C≡C), 80.21 (C≡C), 84.36 (OC-$^t$Bu), 151.59 (COO$^t$Bu), 159.47 (COO), and 190.32 (C=O).

Example 6—Tert-butyl 4-((2-oxopropanoyl-1-$^{13}$C)oxy)but-2-ynoate (2c-$^{13}$C)

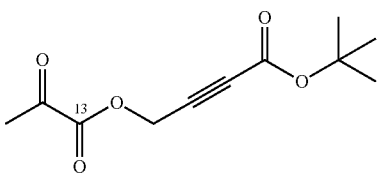 [SMILES: CC(=O)C(=O)OCC#CC(=O)OC(C)(C)C]

Structure 2c-$^{13}$C ($^{13}$C-labeled 2c) was prepared from alcohol 1c (4.40 g, 28.1 mmol), pyruvic acid-1-$^{13}$C (5.00 g, 56.1 mmol, 2.0 eq.), pyridine (11.3 mL, 140 mmol, 5.0 eq.) and methanesulfonyl chloride (4.34 mL, 56.1 mmol, 2.0 eq.) in THF (80 mL) for 4 h at 0° C. according to general procedure A. Purification was via flash chromatography yielding 2c-$^{13}$C as a colorless, slightly viscous liquid (4.50 g, 19.8 mmol, 70% yield).

Figure 6A:
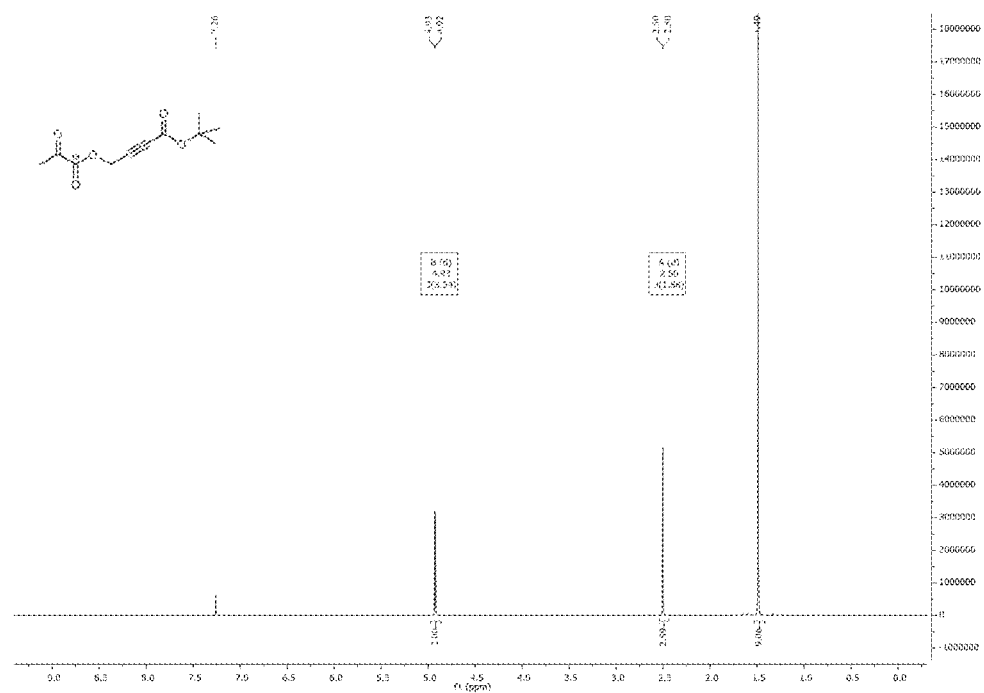
FIG. 6A shows an exemplary $^1$H NMR spectrum corresponding to tert-butyl 4-((2-oxopropanoyl-1-$^{13}$C)oxy)but-2-ynoate, in accordance with various embodiments.

FIG. 6A shows an exemplary $^1$H NMR (400 MHz, CDCl$_3$) spectrum corresponding to structure 2c-$^{13}$C. The NMR spectrum displayed peaks at d=1.49 (s, 9H, $^t$Bu), 2.50 (d, $^3J_{C,H}$=1.58 Hz, CH$_3$), and 4.93 (d, $^3J_{C,H}$=3.54 Hz, 2H, OCH$_2$).

Figure 6B:
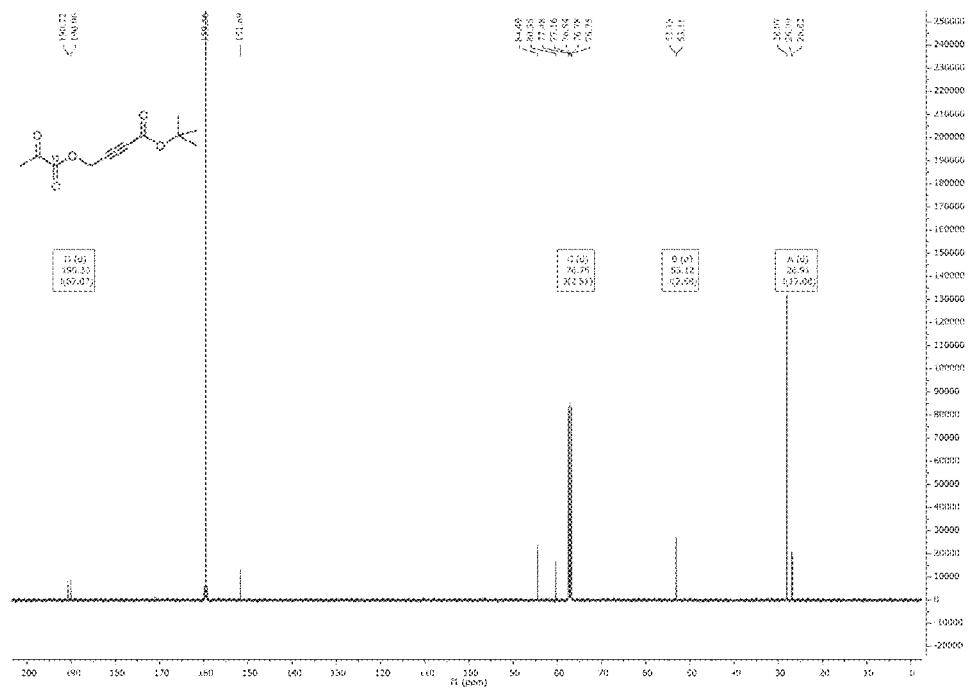
FIG. 6B shows an exemplary $^{13}$C NMR corresponding to tert-butyl 4-((2-oxopropanoyl-1-$^{13}$C)oxy)but-2-ynoate, in accordance with various embodiments.

FIG. 6B shows an exemplary $^{13}$C NMR (101 MHz, CDCl$_3$) spectrum corresponding to structure 2c-$^{13}$C. The NMR spectrum displayed peaks at d=26.91 (d, $^2J_{C,C}$=17.08 Hz, CH$_3$), 28.07 (3×CH$_3$), 53.12 (d, $^2J_{C,C}$=2.58 Hz, OCH$_2$), 76.76 (d, $^3J_{C,C}$=2.51 Hz, C≡C), 80.35 (C≡C), 84.49 (OC-$^t$Bu), 151.69 (COO$^t$Bu), 159.56 (COO), and 190.39 (d, $^1J_{C,C}$=67.07, C=O).

Example 7—2-(Methyl-$d_3$)propan-2-yl-1,1,1,3,3,3-$d_6$ 4-((2-oxopropanoyl-1-$^{13}$C)oxy)but-2-ynoate (2c-$d_9$-$^{13}$C)

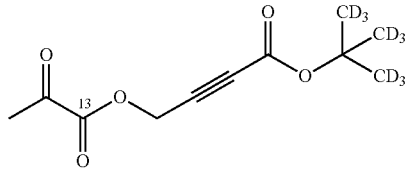 [SMILES: [2H]C([2H])([2H])C(OC(=O)C#CCOC(=O)C(C)=O)(C([2H])([2H])[2H])C([2H])([2H])[2H]]

Structure 2c-$d_9$-$^{13}$C (9× deuterated and $^{13}$C-labeled structure 2c) was prepared from alcohol 1c-$d_9$ (5.50 g, 33.2 mmol), pyruvic acid-1-$^{13}$C (5.00 g, 56.1 mmol, 1.7 eq.), pyridine (11.3 mL, 140 mmol, 4.2 eq.) and methanesulfonyl chloride (4.3 mL, 56.1 mmol, 1.7 eq.) in THF (130 mL) for 5 h at 0° C. according to general procedure A. Purification was via flash chromatography yielding 2c-$d_9$-$^{13}$C as a colorless, slightly viscous liquid (5.08 g, 21.6 mmol, 65% yield).

Figure 7A:
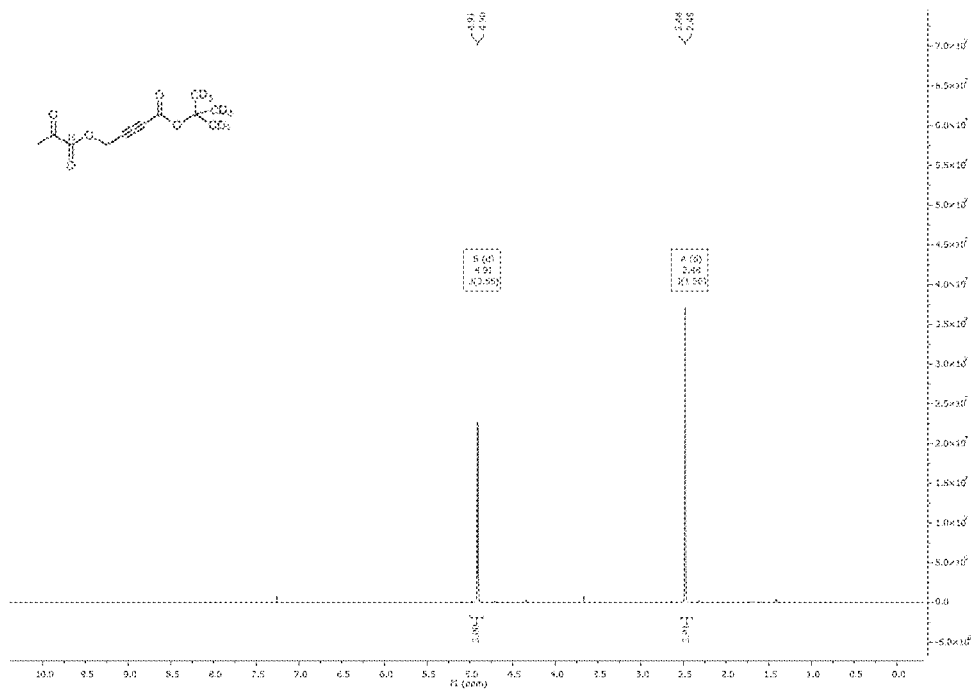
FIG. 7A shows an exemplary $^1$H NMR spectrum corresponding to 2-(methyl-d$_3$)propan-2-yl-1,1,1,3,3,3-d$_6$ 4-((2-oxopropanoyl-1-$^{13}$C)oxy)but-2-ynoate, in accordance with various embodiments.

FIG. 7A shows an exemplary $^1$H NMR (400 MHz, CDCl$_3$) spectrum corresponding to structure 2c-$d_9$-$^{13}$C. The NMR spectrum displayed peaks at d=2.48 (d, $^3J_{C,H}$=1.56 Hz, CH$_3$), and 4.91 (d, $^3J_{C,H}$=3.55 Hz, 2H, OCH$_2$).

Figure 7B:
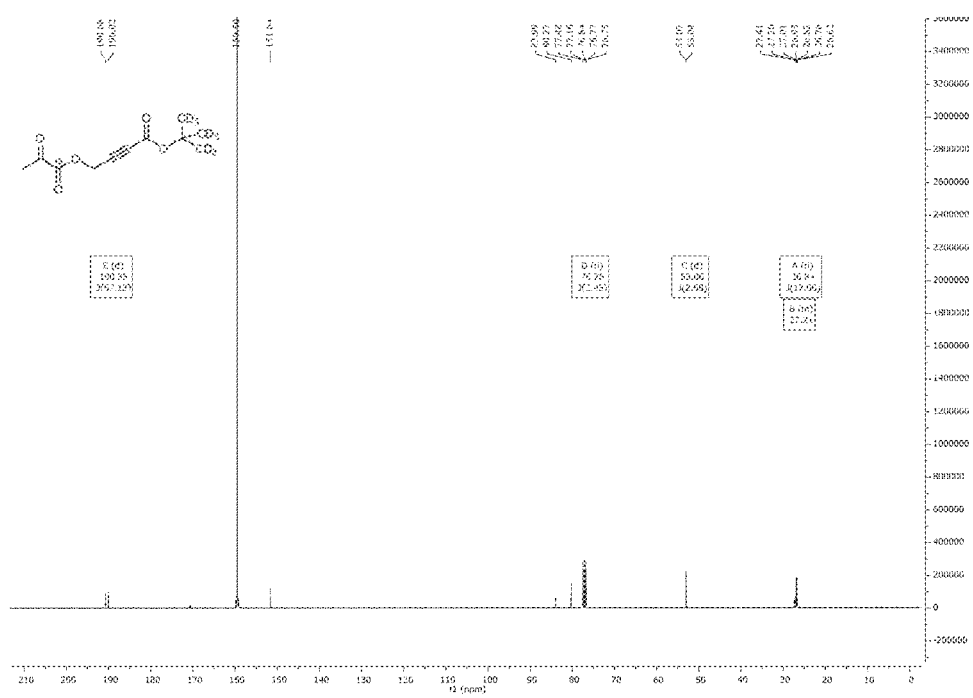
FIG. 7B shows an exemplary $^{13}$C NMR corresponding to 2-(methyl-d$_3$)propan-2-yl-1,1,1,3,3,3-d$_6$ 4-((2-oxopropanoyl-1-$^{13}$C)oxy)but-2-ynoate, in accordance with various embodiments.

FIG. 7B shows an exemplary $^{13}$C NMR (101 MHz, CDCl$_3$) spectrum corresponding to 2c-$d_9$-$^{13}$C. The NMR spectrum displayed peaks at d=26.62-27.41 (multiplet (m), 3×CD$_3$), 26.84 (d, $^2J_{C,C}$=17.06 Hz, CH$_3$), 53.06 (d, $^2J_{C,C}$=2.68 Hz, OCH$_2$), 76.76 (d, $^3J_{C,C}$=2.45 Hz, C≡C), 80.27 (C≡C), 83.99 (OC-$^t$Bu), 151.64 (COO$^t$Bu), 159.50 (COO), and 190.35 (d, $^1J_{C,C}$=67.13, C=O).

Example 8—Tert-butyl 4-((2-oxopropanoyl)oxy)but-2-ynoate-4-d (2c-$d_1$)

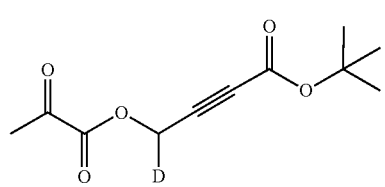 [SMILES: [2H]C(C#CC(=O)OC(C)(C)C)OC(=O)C(C)=O]

Structure 2c-$d_1$ (1× deuterated structure 2c) was prepared from alcohol 1c-$d_1$ (14.0 g, 89.0 mmol), pyruvic acid (15.8 g, 178 mmol, 2.0 eq.), pyridine (36.0 mL, 445 mmol, 5.0 eq.) and methanesulfonyl chloride (13.8 mL, 178 mmol, 2.0 eq.) in THF (400 mL) for 1 h at 0° C. and 3 h at ambient temperature according to general procedure A. Purification was via flash chromatography yielding 2c-$d_1$ as a yellowish, slightly viscous liquid (13.2 g, 58.1 mmol, 65% yield).

Figure 8A:
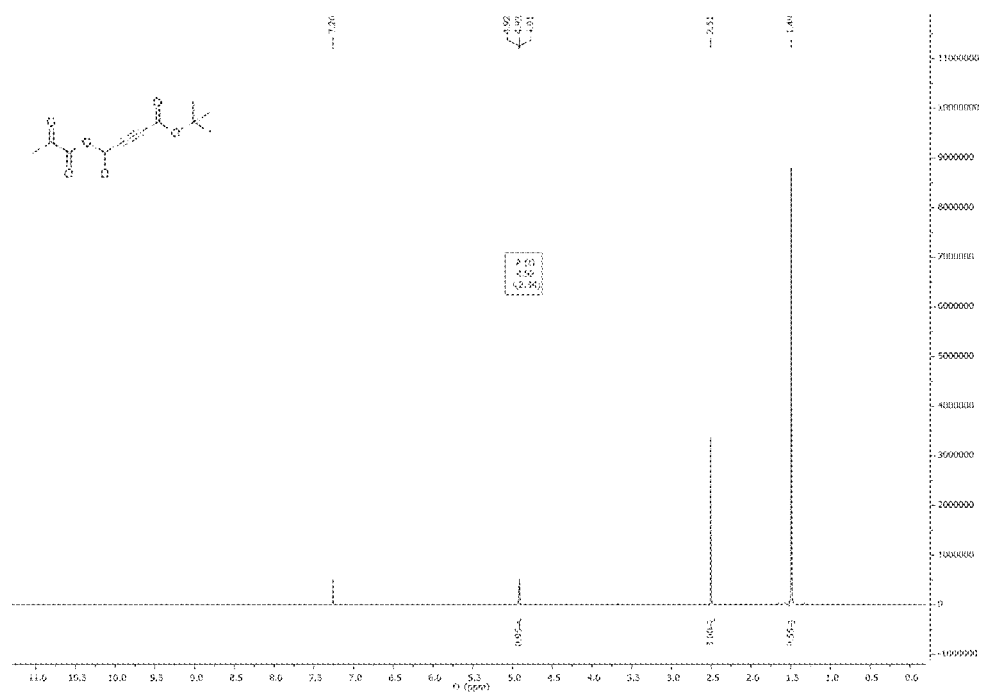
FIG. 8A shows an exemplary $^1$H NMR spectrum corresponding to tert-butyl 4-((2-oxopropanoyl)oxy)but-2-ynoate-4-d, in accordance with various embodiments.

FIG. 8A shows an exemplary $^1$H NMR (400 MHz, CDCl$_3$) spectrum corresponding to structure 2c-$d_1$. The NMR spectrum displayed peaks at d=1.49 (s, 9H, $^t$Bu), 2.51 (s, 3H, CH$_3$), and 4.92 (triplet (t), $^2J_{H,D}$=2.34 Hz, 2H, OCH$_2$).

Figure 8B:
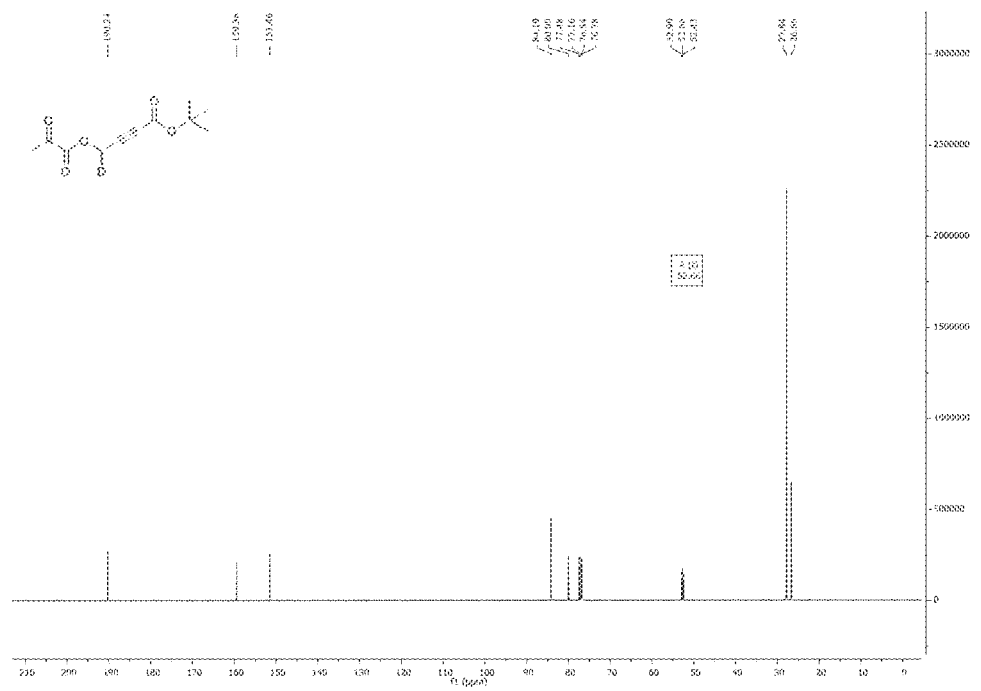
FIG. 8B shows an exemplary $^{13}$C NMR corresponding to tert-butyl 4-((2-oxopropanoyl)oxy)but-2-ynoate-4-d, in accordance with various embodiments.

FIG. 8B shows an exemplary $^{13}$C NMR (101 MHz, CDCl$_3$) spectrum corresponding to structure 2c-$d_1$. The NMR spectrum displayed peaks at d=26.66 (CH$_3$), 27.84 (3×CH$_3$), 52.66 (t, $^1J_{C,D}$=23.56 Hz, OCHD), 76.78 (C≡C), 80.00 (C≡C), 84.19 (OC-$^t$Bu), 151.46 (COO$^t$Bu), 159.36 (COO), and 190.24 (C=O).

Example 9—Tert-butyl 4-((2-oxopropanoyl)oxy)pent-2-ynoate (2d)

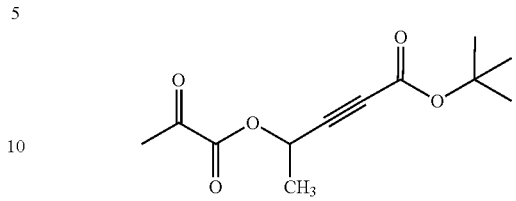

Structure 2d was prepared from alcohol 1d (4.83 g, 28.4 mmol), pyruvic acid (5.00 g, 56.8 mmol, 2.0 eq.), pyridine (11.5 mL, 142 mmol, 5.0 eq.) and methanesulfonyl chloride (4.40 mL, 56.8 mmol, 2.0 eq.) in THF (80 mL) for 3 h at 0° C. and 1 h at ambient temperature according to general procedure A. Purification was via flash chromatography yielding 2d as a yellowish, slightly viscous liquid (4.85 g, 20.2 mmol, 71% yield).

Figure 9A:
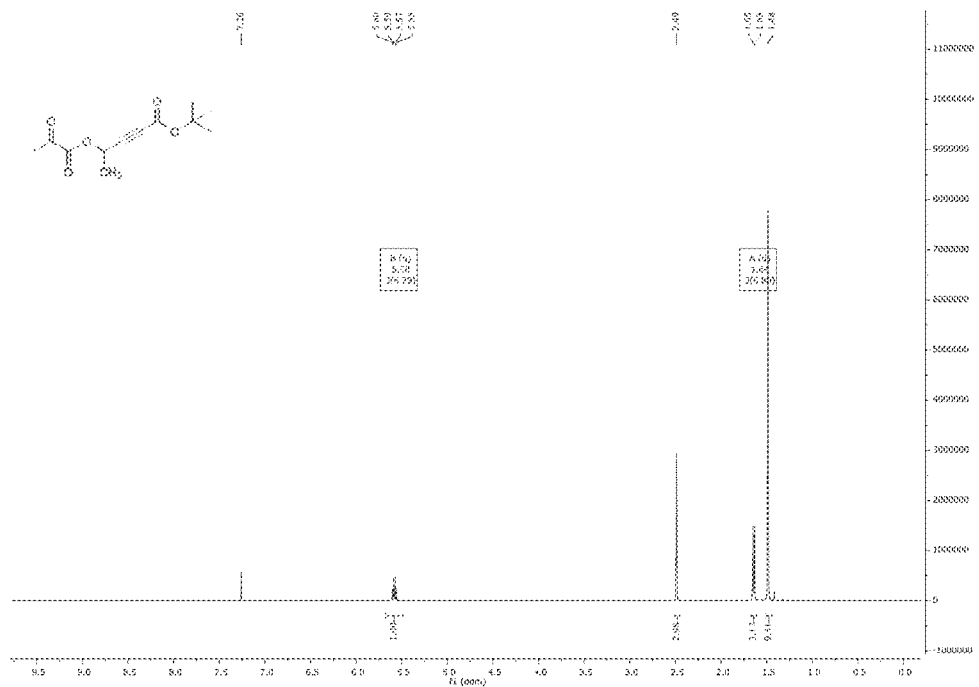
FIG. 9A shows an exemplary $^1$H NMR spectrum corresponding to tert-butyl 4-((2-oxopropanoyl)oxy)pent-2-ynoate, in accordance with various embodiments.

FIG. 9A shows an exemplary $^1$H NMR (400 MHz, CDCl$_3$) spectrum corresponding to structure 2d. The NMR spectrum displayed peaks at d=1.48 (s, 9H, $^t$Bu), 1.64 (d, $^3J_{H,H}$=6.80 Hz, OCHCH$_3$), 2.49 (s, 3H, CH$_3$), and 5.58 (quartet (q), $^3J_{H,H}$=6.79 Hz, 1H, OCHCH$_3$).

Figure 9B:
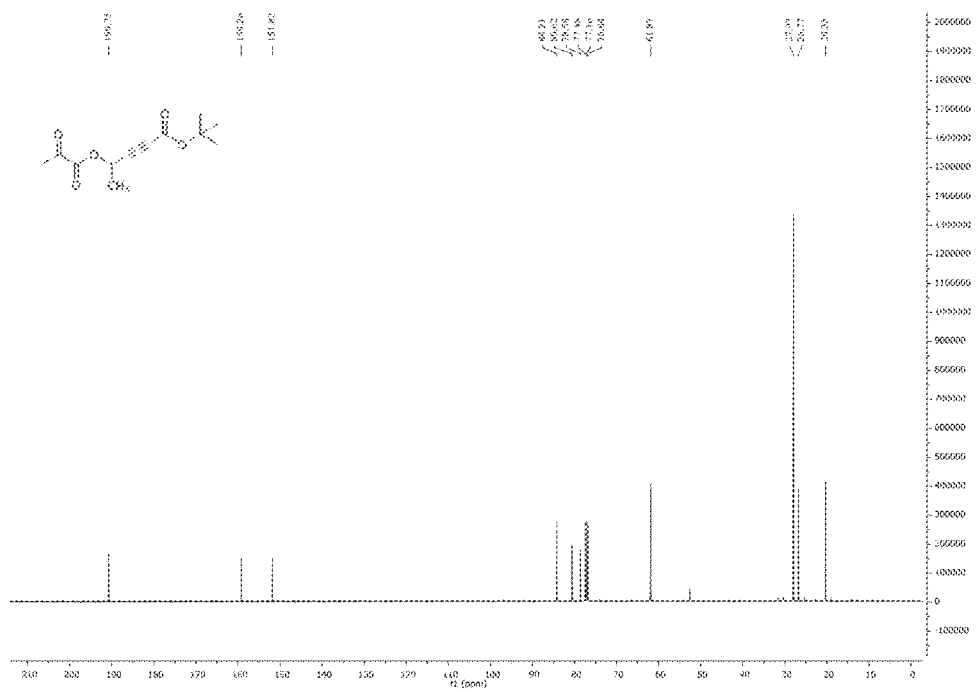
FIG. 9B shows an exemplary $^{13}$C NMR corresponding to tert-butyl 4-((2-oxopropanoyl)oxy)pent-2-ynoate, in accordance with various embodiments.

FIG. 9B shows an exemplary $^{13}$C NMR (101 MHz, CDCl$_3$) spectrum corresponding to structure 2d. The NMR spectrum displayed peaks at d=20.35 (OCHCH$_3$), 26.77 (CH$_3$), 27.97 (3×CH$_3$), 61.87 (OCHCH$_3$), 78.58 (C≡C), 80.62 (C≡C), 84.21 (OC-$^t$Bu), 151.82 (COO$^t$Bu), 159.26 (COO), and 190.75 (C=O).

Example 9—Tert-butyl 4-((2-oxopropanoyl)oxy)-4-phenylbut-2-ynoate (2e)

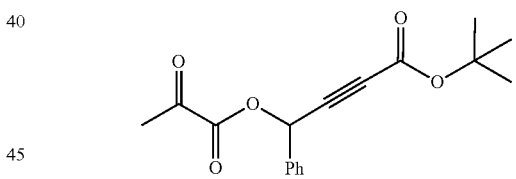

Structure 2e was prepared from alcohol 1e (5.81 g, 25.0 mmol), pyruvic acid (4.40 g, 50.0 mmol, 2.0 eq.), pyridine (10.7 mL, 125 mmol, 5.0 eq.) and methanesulfonyl chloride (3.87 mL, 50.0 mmol, 2.0 eq.) in THF (100 mL) for 1.5 h at 0° C. and 2.5 h at ambient temperature according to general procedure A. Purification was via flash chromatography yielding 2e as a yellowish, viscous liquid (5.00 g, 16.5 mmol, 66% yield).

Figure 10A:
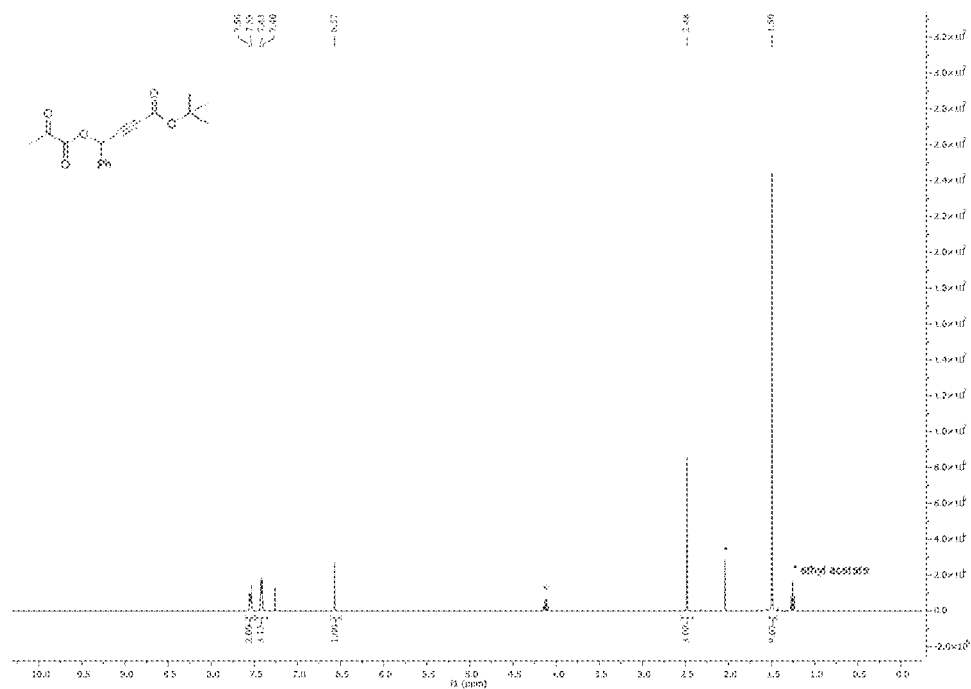
FIG. 10A shows an exemplary $^1$H NMR spectrum corresponding to tert-butyl 4-((2-oxopropanoyl)oxy)-4-phenylbut-2-ynoate, in accordance with various embodiments.

FIG. 10A shows an exemplary $^1$H NMR (400 MHz, CDCl$_3$) spectrum corresponding to structure 2e. The NMR spectrum displayed peaks at d=1.50 (s, 9H, $^t$Bu), 2.48 (s, 3H, CH$_3$), 6.57 (s, 1H, OCHPh), 7.40-7.43 (m, 3H, H$_{Ph}$), and 7.53-7.56 (m, 2H, H$_{Ph}$).

Figure 10B:
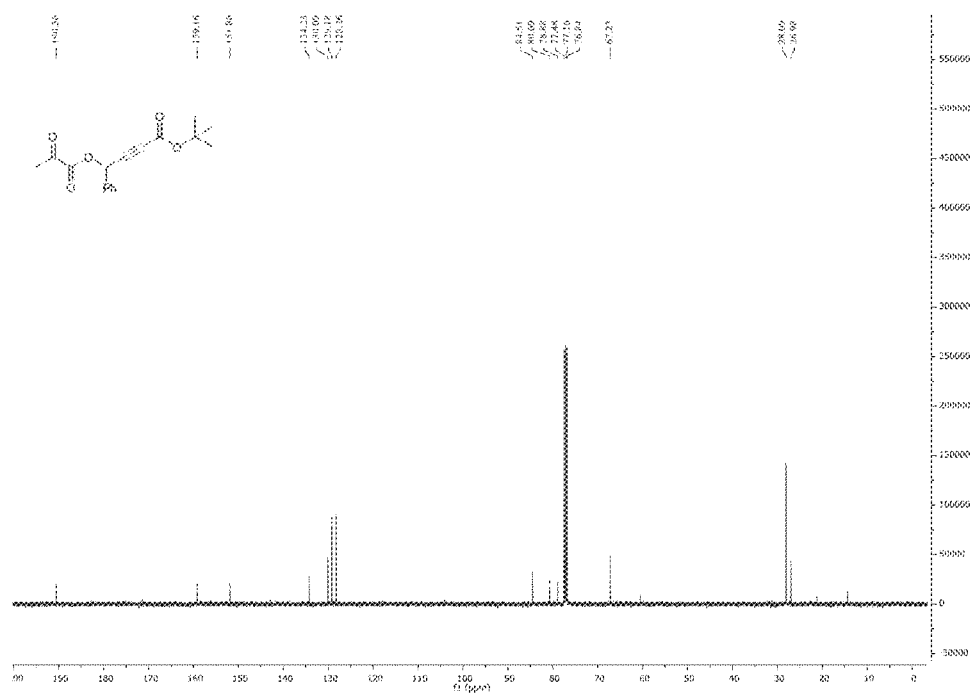
FIG. 10B shows an exemplary $^{13}$C NMR corresponding to tert-butyl 4-((2-oxopropanoyl)oxy)-4-phenylbut-2-ynoate, in accordance with various embodiments.

FIG. 10B shows an exemplary $^{13}$C NMR (101 MHz, CDCl$_3$) spectrum corresponding to structure 2e. The NMR spectrum displayed peaks at d=26.98 (CH$_3$), 28.09 (3×CH$_3$), 67.23 (OCHPh), 78.88 (C≡C), 80.69 (C≡C), 84.51 (OC-$^t$Bu), 128.26 (C$_{Ph}$), 129.18 (C$_{Ph}$), 130.09 (C$_{Ph}$), 134.23 (C$_{Ph}$), 151.86 (COO$^t$Bu), 159.16 (COO), and 190.56 (C=O).

Example 10—Benzhydryl 4-((2-oxopropanoyl)oxy)but-2-ynoate (2f)

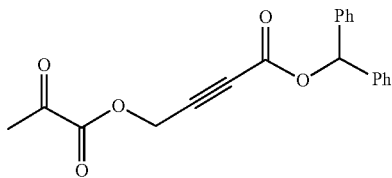 [SMILES: CC(=O)C(=O)OCC#CC(=O)OC(c1ccccc1)c1ccccc1]

Structure 2f was prepared from 1f (1.60 g, 6.00 mmol) according to general procedure B yielding 2f as a colorless, viscous oil (1.92 g, 5.70 mmol, 95% yield).

Figure 11:
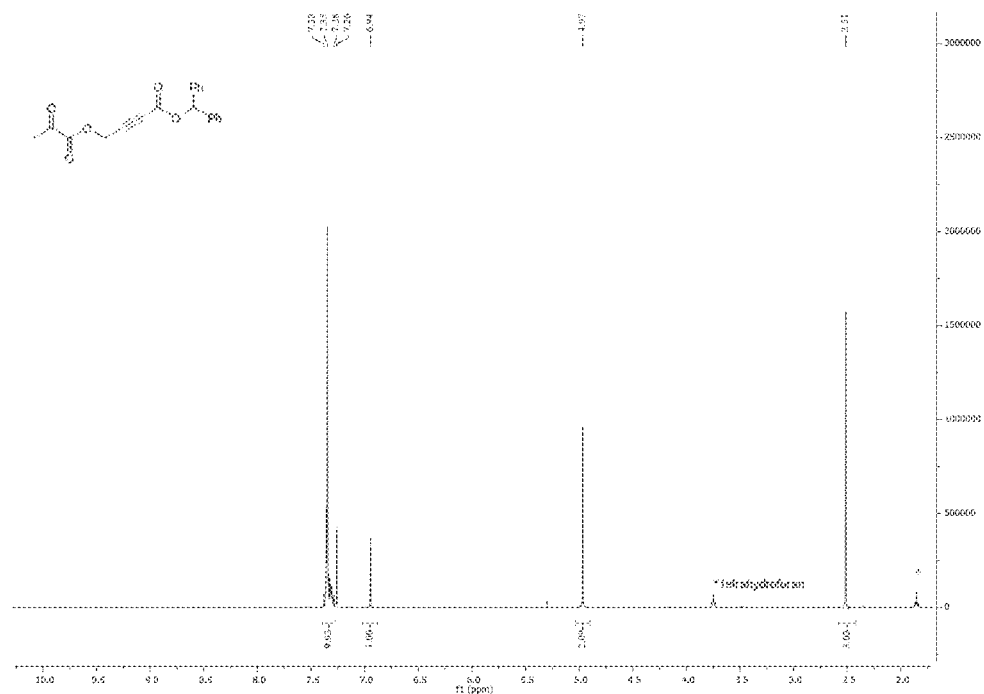
FIG. 11 shows an exemplary $^1$H NMR spectrum corresponding to benzhydryl 4-((2-oxopropanoyl)oxy)but-2-ynoate, in accordance with various embodiments.

FIG. 11 shows an exemplary $^1$H NMR (400 MHz, CDCl$_3$) spectrum corresponding to structure 2f. The NMR spectrum displayed peaks at d=2.51 (s, 3H, CH$_3$), 4.97 (s, 2H, OCH$_2$), 6.94 (s, 1H, OCH), and 7.28-7.38 (m, 10H, H$_{Ph}$).

Example 11—4-Oxo-4-phenylbut-2-yn-1-yl 2-oxopropanoate (2g)

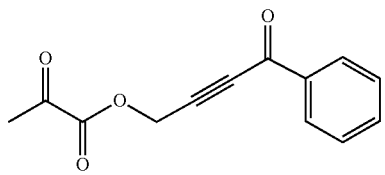 [SMILES: CC(=O)C(=O)OCC#CC(=O)c1ccccc1]

Structure 2g was prepared from 1g (2.49 g, 15.5 mmol) according to general procedure B purified with flash chromatography yielding 2g-d$_5$ as a slightly orange solid (1.86 g, 8.06 mmol, 52% yield).

Figure 12A:
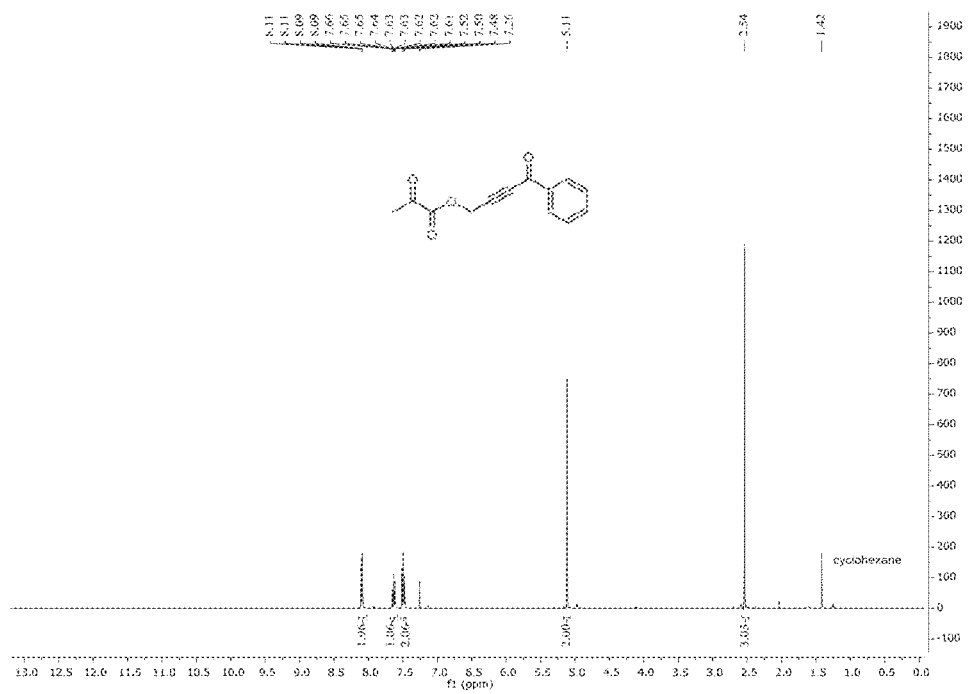
FIG. 12A shows an exemplary $^1$H NMR spectrum corresponding to 4-oxo-4-phenylbut-2-yn-1-yl 2-oxopropanoate, in accordance with various embodiments.

FIG. 12A shows an exemplary $^1$H NMR (400 MHz, CDCl$_3$) spectrum corresponding to structure 2g. The NMR spectrum displayed peaks at d=2.54 (s, 3H, CH$_3$), 5.11 (s, 2H, OCH$_2$), 7.48-7.52 (m, 2H, H$_{Ph}$), 7.61-7.66 (m, 1H, H$_{Ph}$), and 8.09-8.11 (m, 2H, H$_{Ph}$).

Figure 12B:
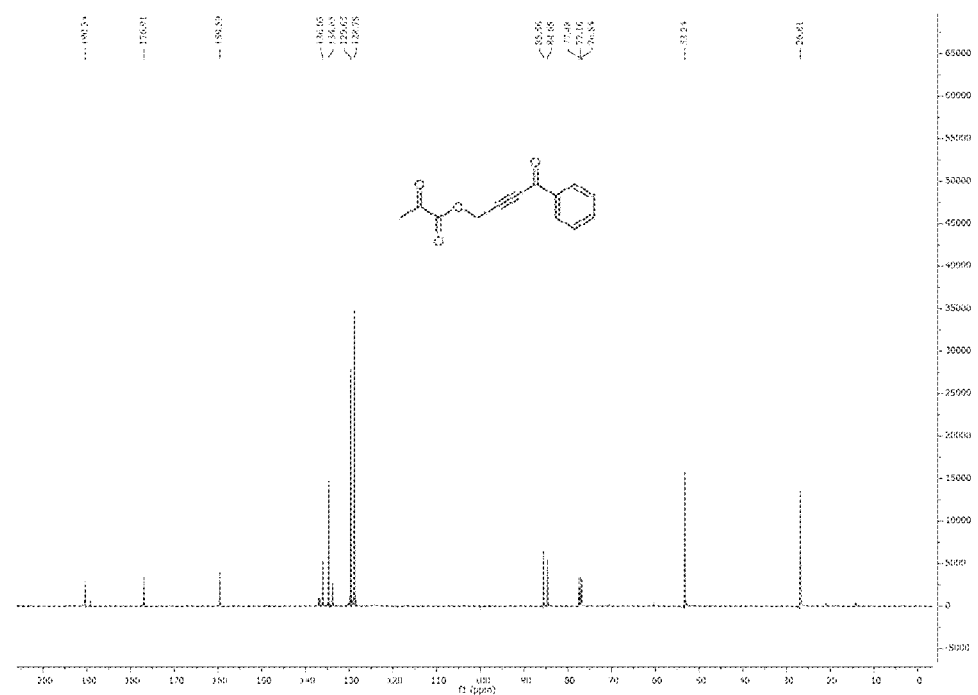
FIG. 12B shows an exemplary $^{13}$C NMR corresponding to 4-oxo-4-phenylbut-2-yn-1-yl 2-oxopropanoate, in accordance with various embodiments.

FIG. 12B shows an exemplary $^{13}$C NMR (101 MHz, CDCl$_3$) spectrum corresponding to structure 2g. The NMR spectrum displayed peaks at d=26.81 (CH$_3$), 53.24 (OCH$_2$), 84.65 (C≡C), 85.56 (C≡C), 128.78 (C$_{Ph}$), 129.65 (C$_{Ph}$), 134.65 (C$_{Ph}$), 136.03 (C$_{Ph}$), 159.59 (COO), 176.91 (C(O)Ph), and 190.34 (C=O).

Example 12-4-Oxo-4-(phenyl-d$_5$)but-2-yn-1-yl 2-oxopropanoate (22-d$_5$)

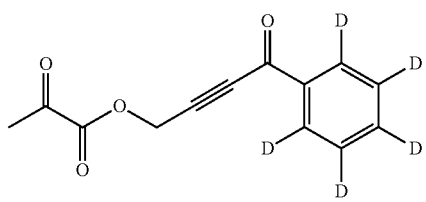 [SMILES: [2H]c1c([2H])c([2H])c(C(=O)C#CCOC(=O)C(C)=O)c([2H])c1[2H]]

Structure 2g-d$_5$ was prepared from 1g-d$_5$ (4.66 g, 28.2 mmol) according to general procedure B yielding 2g-d$_5$ as a brownish solid (6.1 g, 25.9 mmol, 92%).

Figure 13A:
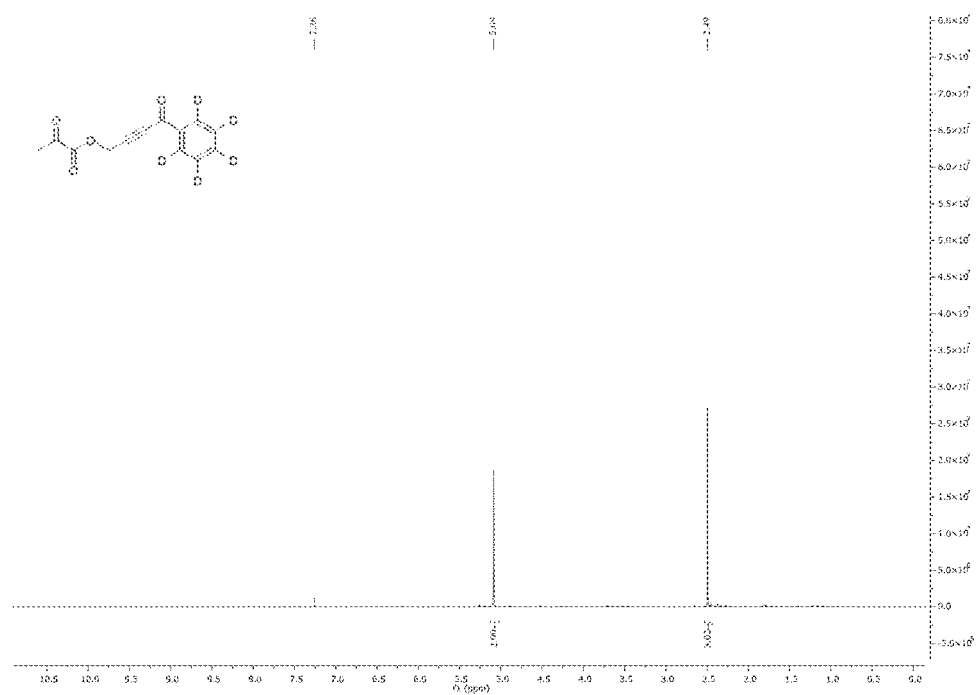
FIG. 13A shows an exemplary $^1$H NMR spectrum corresponding to 4-oxo-4-(phenyl-d$_5$)but-2-yn-1-yl 2-oxopropanoate, in accordance with various embodiments.

FIG. 13A shows an exemplary $^1$H NMR (400 MHz, CDCl$_3$) spectrum corresponding to structure 2g-d$_5$. The NMR spectrum displayed peaks at d=2.49 (s, 3H, CH$_3$) and 5.09 (s, 2H, OCH$_2$).

Figure 13B:
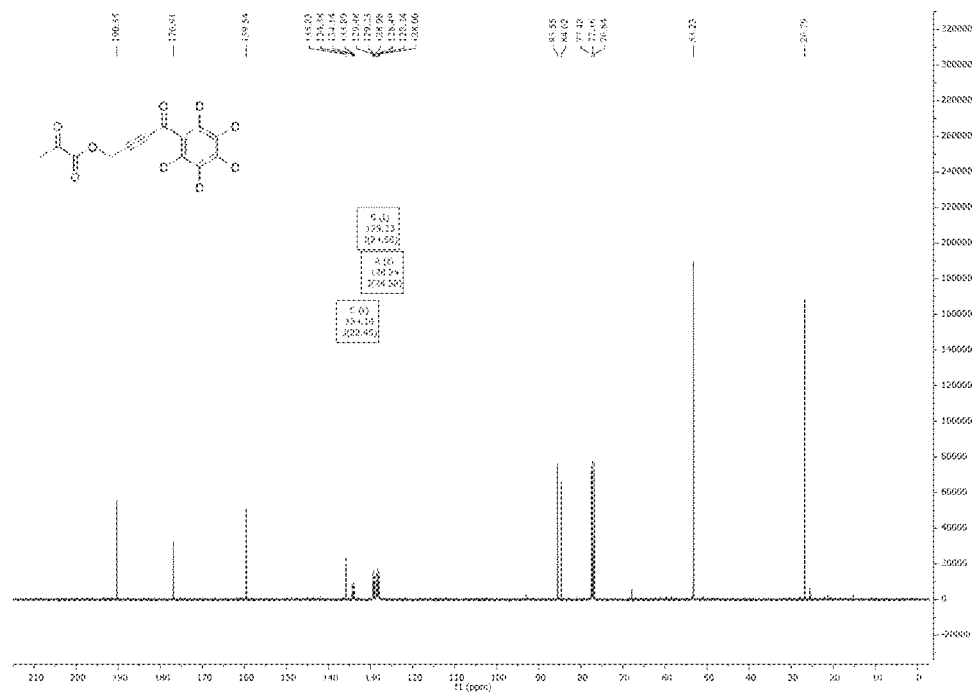
FIG. 13B shows an exemplary carbon-13 ($^{13}$C) NMR corresponding to 4-oxo-4-(phenyl-d$_5$)but-2-yn-1-yl 2-oxopropanoate, in accordance with various embodiments.

FIG. 13B shows an exemplary $^{13}$C NMR (101 MHz, CDCl$_3$) spectrum corresponding to structure 2g-d$_5$. The NMR spectrum displayed peaks at d=26.79 (CH$_3$), 53.23 (OCH$_2$), 84.62 (C≡C), 85.55 (C≡C), 128.24 (t, $^1J_{C,D}$=24.58 Hz, C$_{Ph}$), 129.23 (t, $^1J_{C,D}$=24.58 Hz, C$_{Ph}$), 134.14 (t, $^1J_{C,D}$=22.45 Hz, C$_{Ph}$), 135.83 (C$_{Ph}$), 159.54 (COO), 176.91 (C(O)Ph), and 190.35 (C=O).

Example 13—1-(4-(Tert-butoxy)-4-oxobut-2-yn-1-yl) 5-ethyl 2-oxopentanedioate (3c)

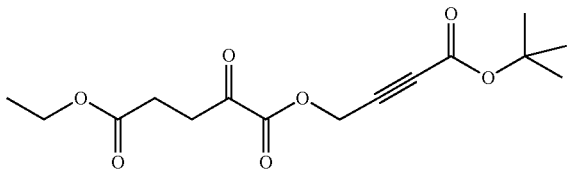 [SMILES: CCOC(=O)CCC(=O)C(=O)OCC#CC(=O)OC(C)(C)C]

Structure 3c was prepared from alcohol 1c (0.92 g, 5.9 mmol), mono-ethyl α-ketoglutarate (1.02 g, 5.85 mmol, 1.0 eq.), pyridine (1.88 mL, 23.3 mmol, 4.0 eq.) and methanesulfonyl chloride (543 μL, 7.02 mmol, 1.2 eq.) in THF (40 mL) for 5 h at 0° C. and 40 h at 7° C. according to general procedure A. Purification was via flash chromatography yielding 3c as a colorless, viscous liquid (1.40 g, 4.48 mmol, 77% yield) containing 20% of 1c because the esterification was not quantitative and 3c and 1c have similar retention times.

Figure 14A:
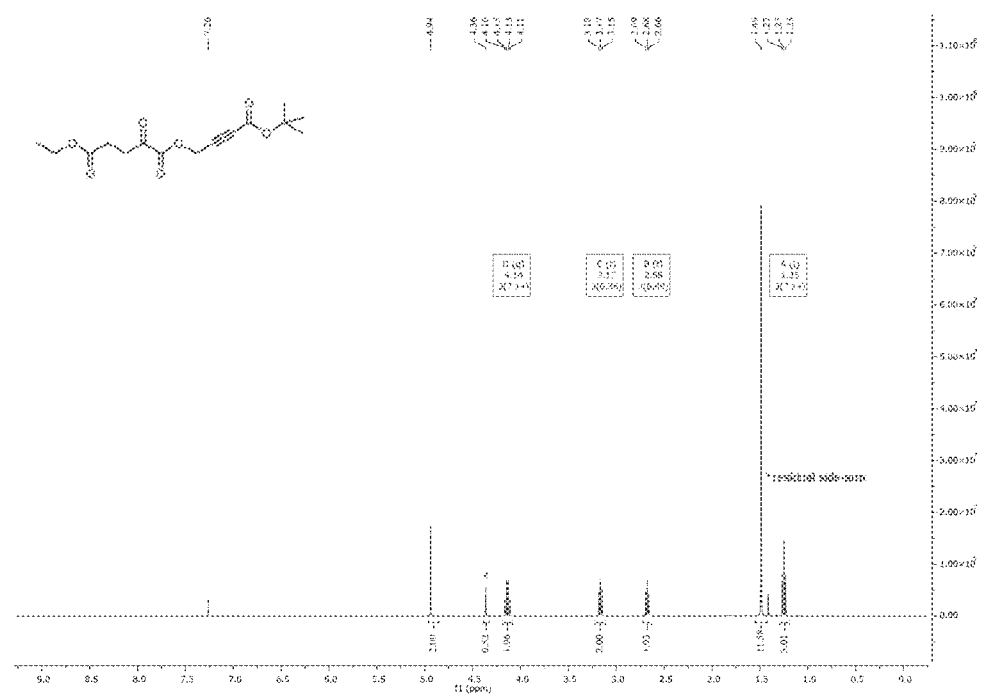
FIG. 14A shows an exemplary $^1$H NMR spectrum corresponding to 1-(4-(tert-butoxy)-4-oxobut-2-yn-1-yl) 5-ethyl 2-oxopentanedioate, in accordance with various embodiments.

FIG. 14A shows an exemplary $^1$H NMR (400 MHz, CDCl$_3$) spectrum corresponding to structure 3c. The NMR spectrum displayed peaks at d=1.25 (t, $^3J_{H,H}$=7.14 Hz, 3H, OCH$_2$CH$_3$), 1.49 (s, 9H, $^t$Bu), 2.68 (t, $^3J_{H,H}$=6.49 Hz, 2H, CH$_2$CH$_2$), 3.17 (t, $^3J_{H,H}$=6.36 Hz, 2H, CH$_2$CH$_2$), 4.14 (q, $^3J_{H,H}$=7.14 Hz, 2H, OCH$_2$CH$_3$), and 4.94 (s, 2H, OCH$_2$).

Figure 14B:
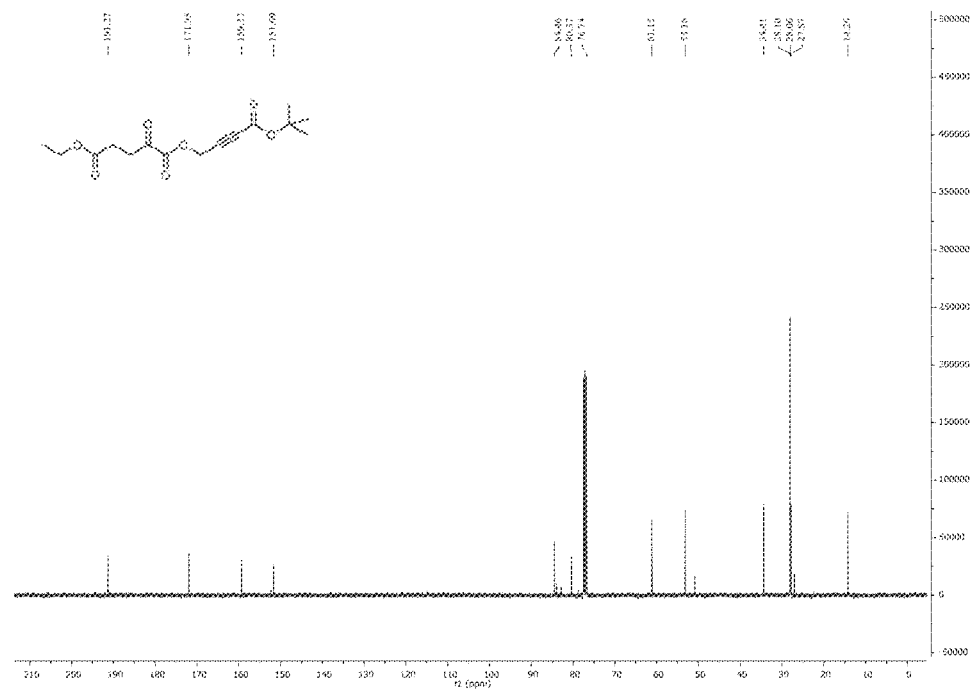
FIG. 14B shows an exemplary $^{13}$C NMR corresponding to 1-(4-(tert-butoxy)-4-oxobut-2-yn-1-yl) 5-ethyl 2-oxopentanedioate, in accordance with various embodiments.

FIG. 14B shows an exemplary $^{13}$C NMR (101 MHz, CDCl$_3$) spectrum corresponding to structure 3c. The NMR spectrum displayed peaks at d=14.26 (OCH$_2$CH$_3$), 27.87 (CH$_2$CH$_2$), 28.06 (3×CH$_3$), 28.10 (CH$_2$CH$_2$), 53.16 (OCH$_2$), 61.15 (OCH$_2$CH$_3$), 76.74 (C≡C), 80.37 (C≡C), 84.46 (OC-$^t$Bu), 151.69 (COO$^t$Bu), 159.33 (COO), 171.95 (COOEt), and 191.27 (C=O).

Example 14—Methyl 4-(2,2-dichloroacetoxy)but-2-ynoate (4a)

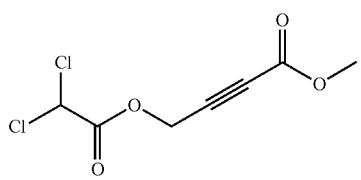

Structure 4a was prepared from 1a (4.00 g, 35.0 mmol) according to general procedure B yielding 4a as a colorless liquid (7.72 g, 34.3 mmol, 98% yield).

Figure 15A:
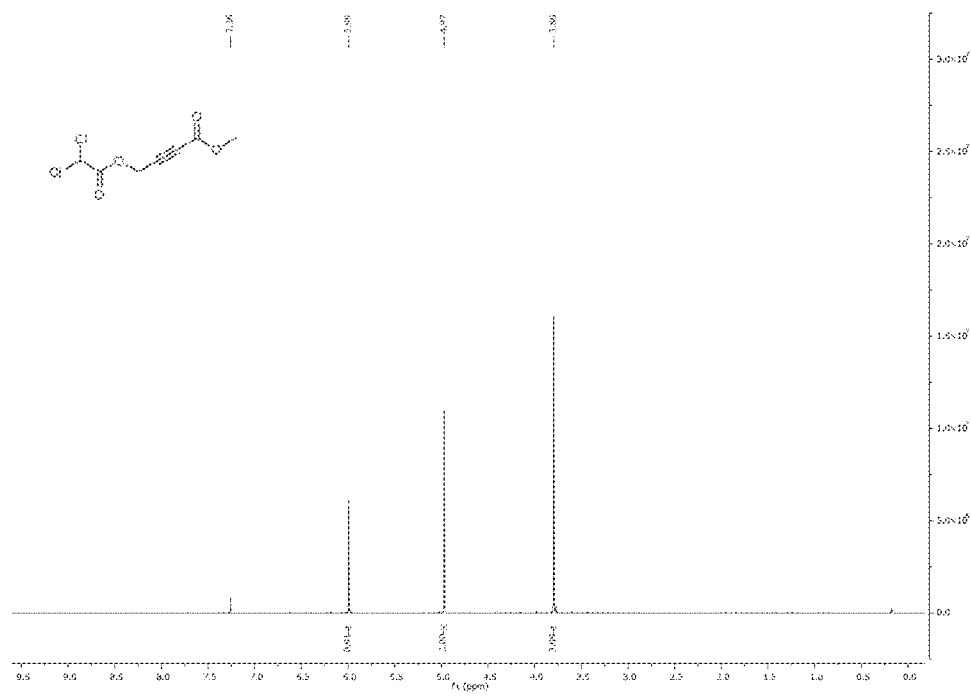
FIG. 15A shows an exemplary $^1$H NMR spectrum corresponding to methyl 4-(2,2-dichloroacetoxy)but-2-ynoate, in accordance with various embodiments.

FIG. 15A shows an exemplary $^1$H NMR (400 MHz, CDCl$_3$) spectrum corresponding to structure 4a. The NMR spectrum displayed peaks at d=3.80 (s, 3H, OCH₃), 4.97 (s, 2H, OCH₂), and 5.99 (s, 1H, CHCl₂).

Figure 15B:
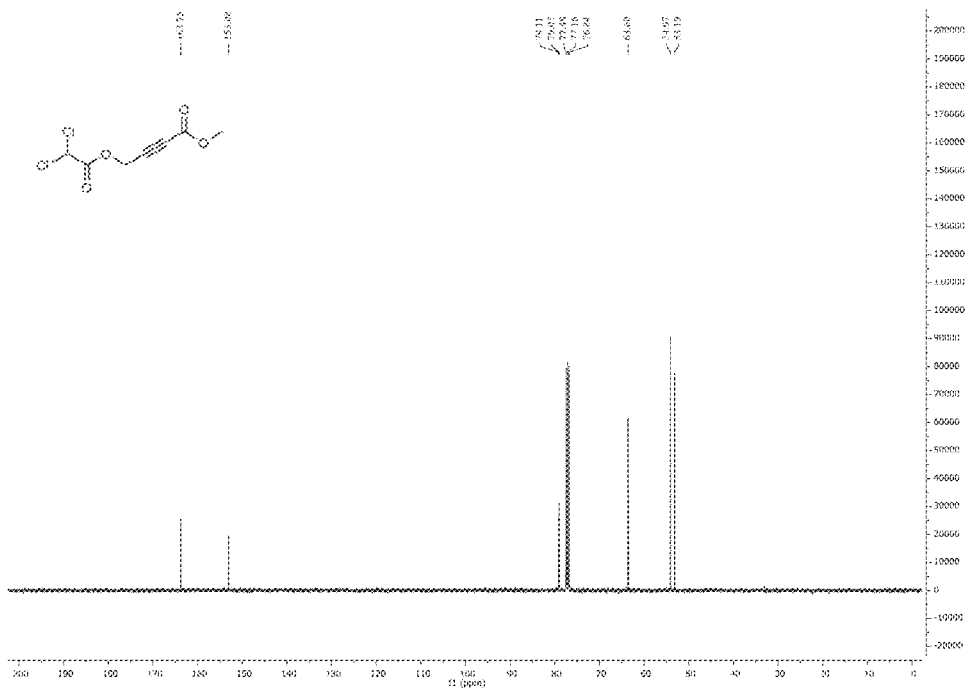
FIG. 15B shows an exemplary $^{13}$C NMR corresponding to methyl 4-(2,2-dichloroacetoxy)but-2-ynoate, in accordance with various embodiments.

FIG. 15B shows an exemplary ¹³C NMR (101 MHz, CDCl₃) spectrum corresponding to structure 4a. The NMR spectrum displayed peaks at d=53.19 (OCH₂), 54.07 (OCH₃), 63.60 (CHCl₂), 79.05 (C≡C), 79.11 (C≡C), 153.08 (COOCH₃), and 163.75 (COO).

Example 15—Tert-butyl 4-((acetoxy)but-2-ynoate (5c)

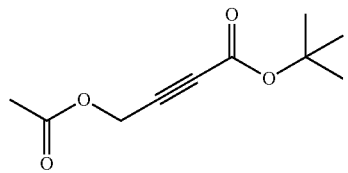

Structure 5c was prepared from 1c (5.50 g, 35.2 mmol) according to general procedure B and purified via flash chromatography, yielding 5c as a colorless liquid (5.72 g, 28.8 mmol, 82% yield).

Figure 16A:
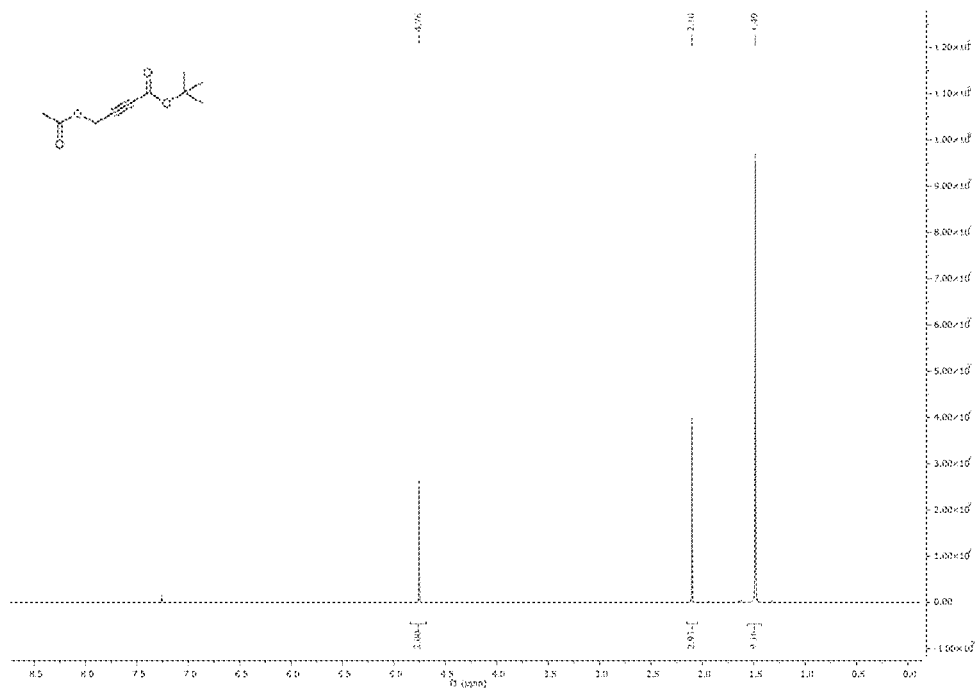
FIG. 16A shows an exemplary $^1$H NMR spectrum corresponding to tert-butyl 4-acetoxybut-2-ynoate, in accordance with various embodiments.

FIG. 16A shows an exemplary 1H NMR (400 MHz, CDCl₃) spectrum corresponding to structure 5c. The NMR spectrum displayed peaks at D=1.49 (s, 9H, ᵗBu), 2.10 (s, 3H, CH₃), and 4.76 (s, 2H, OCH₂).

Figure 16B:
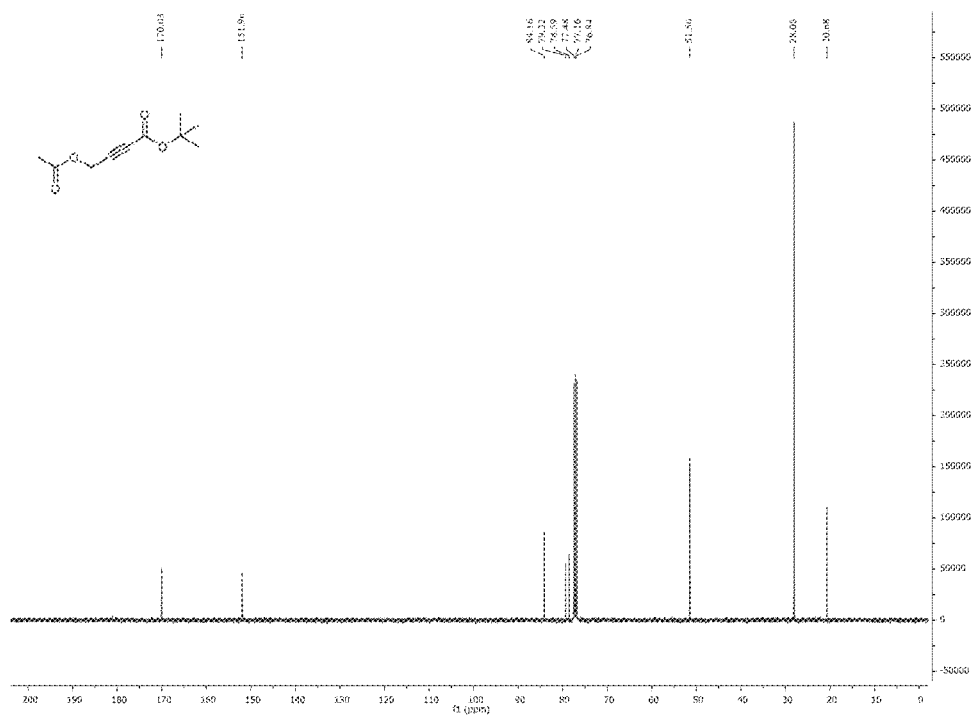
FIG. 16B shows an exemplary $^{13}$C NMR corresponding to tert-butyl 4-acetoxybut-2-ynoate, in accordance with various embodiments.

FIG. 16B shows an exemplary 13C NMR (101 MHz, CDCl₃) spectrum correspond to structure 5c. The NMR spectrum displayed peaks at D=20.68 (CH₃), 28.08 (3×CH₃), 51.50 (OCH₂), 78.59 (C≡C), 79.32 (C≡C), 84.16 (OC-ᵗBu), 151.96 (COOᵗBu), and 170.03 (COO).

Example 16—Improved Hydrogenation Efficiency

Figure 17A:
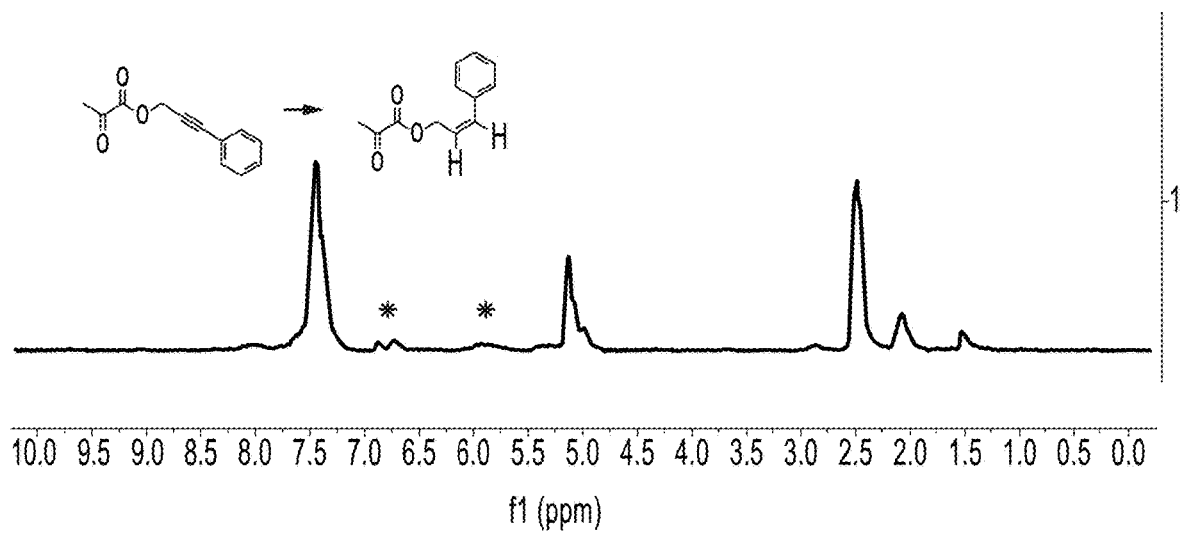
FIG. 17A shows an exemplary $^1$H NMR spectrum corresponding to parahydrogenated 3-phenylprop-2-yn-1-yl 2-oxopropanoate (i.e., 3-phenylallyl 2-oxopropanoate with two protons H* having a spin order derived from parahydrogen), in accordance with various embodiments.

FIG. 17A shows an exemplary ¹H NMR (400 MHz, CDCl₃) spectrum corresponding to parahydrogenated 3-phenylprop-2-yn-1-yl 2-oxopropanoate (i.e., 3-phenylallyl 2-oxopropanoate with two H*). A parahydrogenation reaction between 3-phenylprop-2-yn-1-yl 2-oxopropanoate and parahydrogen was conducted in the presence of 1 mol % [Rh(dppb)(COD)]BF₄ at 60° C. with a parahydrogen pressure of 10 bars for 10 seconds. The reaction formed the previously known 3-phenylallyl 2-oxopropanoate with two H*, where the * symbol indicates a molecule containing protons derived from parahydrogen. In the example shown, the NMR signals marked with a * symbol correspond to the parahydrogen molecules added across the carbon-carbon triple bond of 3-phenylprop-2-yn-1-yl 2-oxopropanoate. Based on the ¹H NMR spectrum, the yield of the parahydrogenation reaction was determined to be approximately 29%.

Figure 17B:
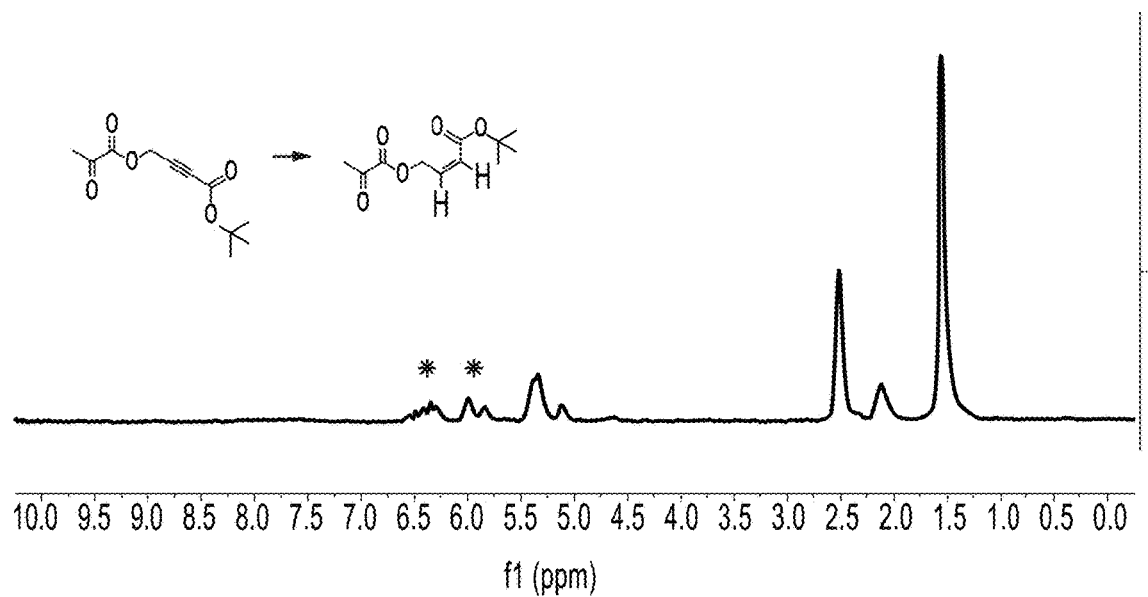
FIG. 17B shows an exemplary $^1$H NMR spectrum corresponding to parahydrogenated tert-butyl 4-((2-oxopropanoyl)oxy)but-2-ynoate (i.e., tert-butyl 4-((2-oxopropanoyl)oxy)but-2-enoate with two H*), in accordance with various embodiments.

FIG. 17B shows an exemplary ¹H NMR (400 MHz, CDCl₃) spectrum corresponding to parahydrogenated tert-butyl 4-((2-oxopropanoyl)oxy)but-2-ynoate (i.e., tert-butyl 4-((2-oxopropanoyl)oxy)but-2-enoate with two H*). A parahydrogenation reaction between this novel molecule and parahydrogen was conducted in the presence of 1 mol % [Rh(dppb)(COD)]BF₄ at 60° C. with a parahydrogen pressure of 10 bars for 10 seconds. The reaction formed tert-butyl 4-((2-oxopropanoyl)oxy)but-2-enoate with two H*, where the * symbol indicates a molecule containing protons derived from parahydrogen. In the example shown, the NMR signals marked with a * symbol correspond to the parahydrogen molecules added across the carbon-carbon triple bond of tert-butyl 4-((2-oxopropanoyl)oxy)but-2-ynoate. Based on the ¹H NMR spectrum, the yield of the parahydrogenation reaction was determined to be approximately 85%.

As shown in FIGS. 17A and 17B, the parahydrogenation reaction between tert-butyl 4-((2-oxopropanoyl)oxy)but-2-ynoate and parahydrogen resulted in a significantly higher yield than the parahydrogenation reaction between 3-phenylprop-2-yn-1-yl 2-oxopropanoate and parahydrogen.

Figure 18A:
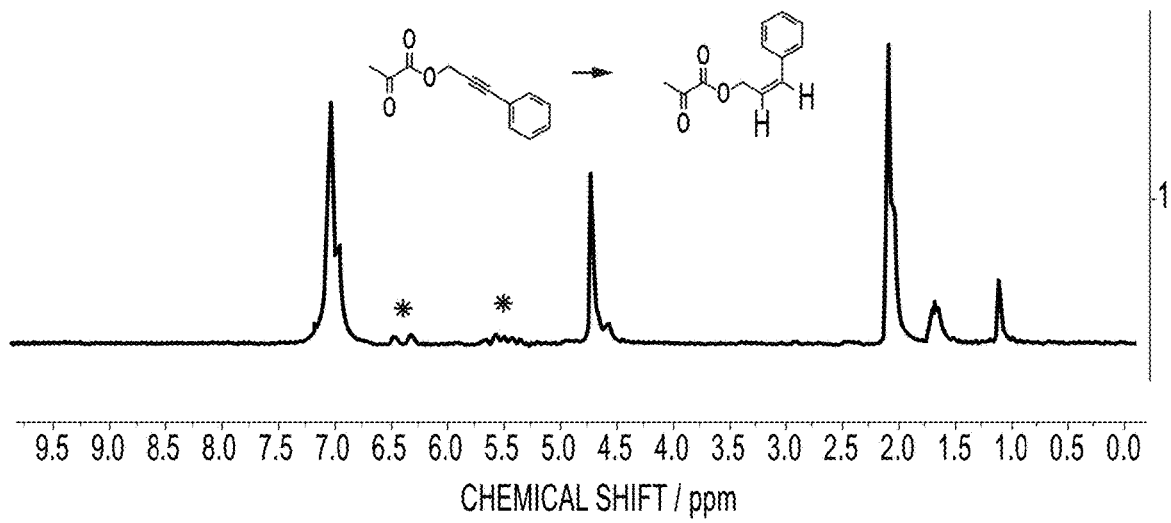
FIG. 18A shows an exemplary $^1$H NMR spectrum corresponding to parahydrogenated 3-phenylprop-2-yn-1-yl 2-oxopropanoate (i.e., 3-phenylallyl 2-oxopropanoate with two H*), in accordance with various embodiments.

FIG. 18A shows an exemplary ¹H NMR (400 MHz, CDCl₃) spectrum corresponding to parahydrogenated 3-phenylprop-2-yn-1-yl 2-oxopropanoate (i.e., 3-phenylallyl 2-oxopropanoate with two H*). A parahydrogenation reaction between 3-phenylprop-2-yn-1-yl 2-oxopropanoate and parahydrogen was conducted in the presence of 1 mol % [Rh(dppb)(COD)]BF₄ at 45° C. with a parahydrogen pressure of 10 bars for 5 seconds. The reaction formed the previously known 3-phenylallyl 2-oxopropanoate with two H*, where the * symbol indicates a molecule containing protons derived from parahydrogen. In the example shown, the NMR signals marked with a * symbol correspond to the parahydrogen molecules added across the carbon-carbon triple bond of 3-phenylpropargyl pyruvate. Based on the ¹H NMR spectrum, the yield of the parahydrogenation reaction was determined to be approximately 21%.

Figure 18B:
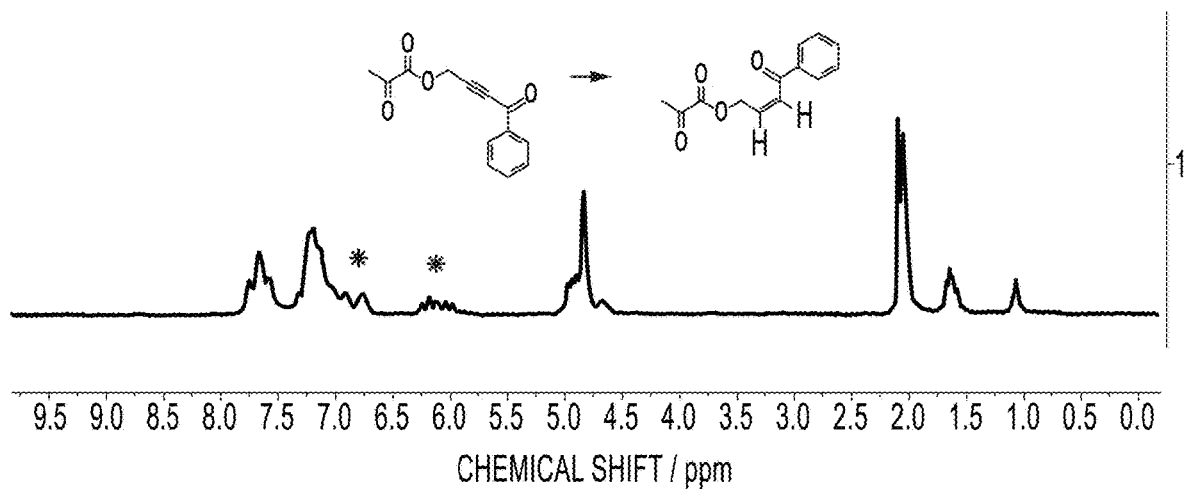
FIG. 18B shows an exemplary $^1$H NMR spectrum corresponding to parahydrogenated 4-oxo-4-phenylbut-2-yn-1-yl 2-oxopropanoate (i.e., 4-oxo-4-phenylbut-2-en-1-yl 2-oxopropanoate with two H*) in accordance with various embodiments.

FIG. 18B shows an exemplary ¹H NMR (400 MHz, CDCl₃) spectrum corresponding to parahydrogenated 4-oxo-4-phenylbut-2-yn-1-yl 2-oxopropanoate (i.e., 4-oxo-4-phenylbut-2-en-1-yl 2-oxopropanoate with two H*). A parahydrogenation reaction between 4-oxo-4-phenylbut-2-yn-1-yl 2-oxopropanoate and parahydrogen was conducted in the presence of 1 mol % [Rh(dppb)(COD)]BF₄ at 45° C. with a parahydrogen pressure of 10 bars for 5 seconds. The reaction formed 4-oxo-4-phenylbut-2-en-1-yl 2-oxopropanoate with two H*, where the * symbol indicates a molecule containing protons derived from parahydrogen. In the example shown, the NMR signals marked with a * symbol correspond to the parahydrogen molecules added across the carbon-carbon triple bond of 4-oxo-4-phenylbut-2-yn-1-yl 2-oxopropanoate. Based on the ¹H NMR spectrum, the yield of the parahydrogenation reaction was determined to be approximately 44%.

As shown in FIGS. 18A and 18B, the parahydrogenation reaction between 4-oxo-4-phenylbut-2-yn-1-yl 2-oxopropanoate and parahydrogen resulted in a significantly higher yield than the parahydrogenation reaction between the known pyruvate derivative, -phenylallyl 2-oxopropanoate, and parahydrogen.

Example 17—Improved ¹³C Polarization

Figure 19A:
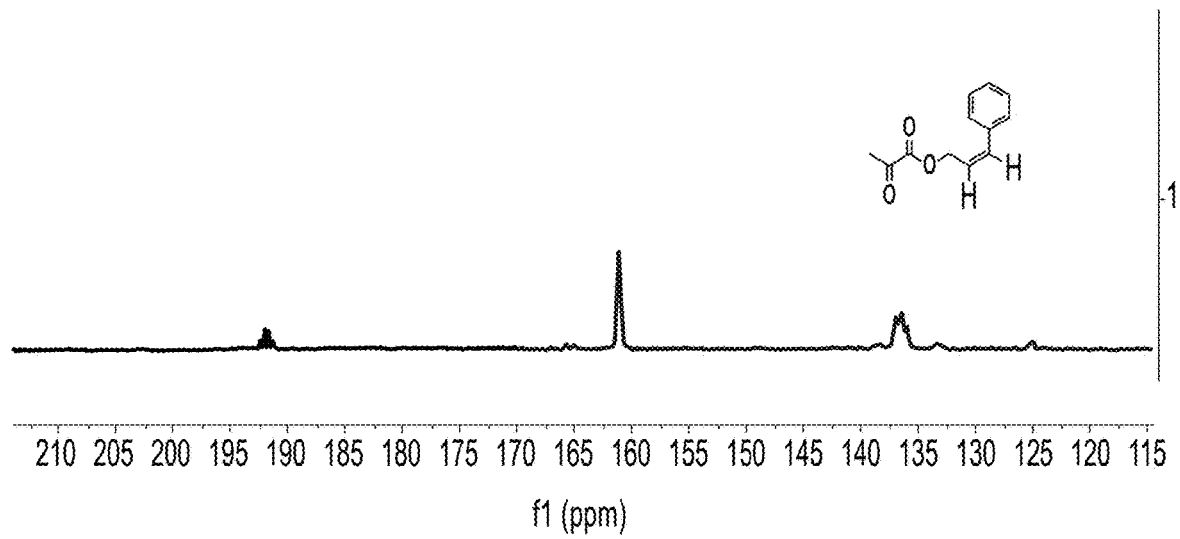
FIG. 19A shows an exemplary $^{13}$C NMR spectrum corresponding to 200 mM parahydrogenated 3-phenylprop-2-yn-1-yl 2-oxopropanoate (i.e., 3-phenylallyl 2-oxopropanoate with two H*), in accordance with various embodiments.

FIG. 19A shows an exemplary ¹³C NMR (101 MHz, CDCl₃) spectrum corresponding to 200 mM parahydrogenated 3-phenylprop-2-yn-1-yl 2-oxopropanoate (i.e., 3-phenylallyl 2-oxopropanoate with two H*) in acetone-d₆. The parahydrogenated 3-phenylprop-2-yn-1-yl 2-oxopropanoate was formed using the procedure described herein with respect to FIG. 17A. In the example shown, the parahydrogenated 3-phenylprop-2-yn-1-yl 2-oxopropanoate was determined to have a ¹³C polarization of about 9.8%.

Figure 19B:
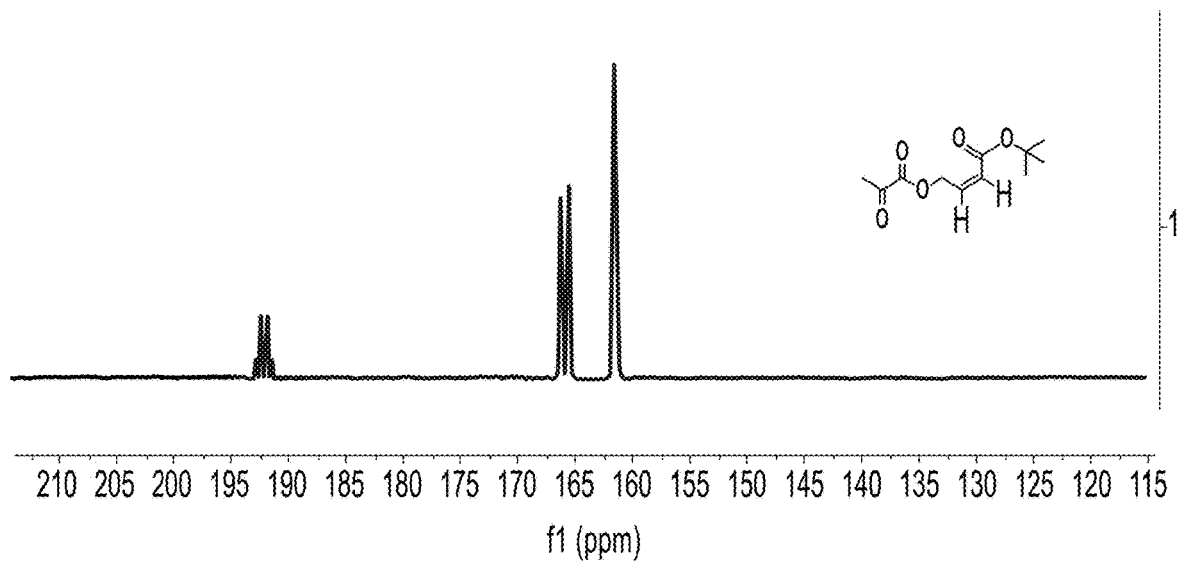
FIG. 19B shows an exemplary $^{13}$C NMR spectrum corresponding to 200 mM parahydrogenated tert-butyl 4-((2-oxopropanoyl)oxy)but-2-ynoate (i.e tert-butyl 4-((2-oxopropanoyl)oxy)but-2-enoate with two H*), in accordance with various embodiments.

FIG. 19B shows an exemplary ¹³C NMR (101 MHz, CDCl₃) spectrum corresponding to 200 mM parahydrogenated tert-butyl 4-((2-oxopropanoyl)oxy)but-2-ynoate (i.e tert-butyl 4-((2-oxopropanoyl)oxy)but-2-enoate with two H*) in acetone-d₆. The parahydrogenated tert-butyl 4-((2-oxopropanoyl)oxy)but-2-ynoate was formed using the procedure described herein with respect to FIG. 17B. In the example shown, the parahydrogenated tert-butyl 4-((2-oxopropanoyl)oxy)but-2-ynoate was determined to have a $^{13}$C polarization of about 17.5%.

As shown in FIGS. 19A and 19B, the parahydrogenated tert-butyl 4-((2-oxopropanoyl)oxy)but-2-ynoate yielded a significantly higher polarization than the parahydrogenated 3-phenylprop-2-yn-1-yl 2-oxopropanoate. It should be noted that parahydrogenated 3-phenylpropargyl pyruvate represents one of the current gold standard precursors for producing hyperpolarized pyruvate via PHIP-SAH. Thus, the compositions described herein may allow the production of pyruvate and other biorelevant imaging agents with significantly enhanced polarizations compared to known precursors.

Figure 20A:
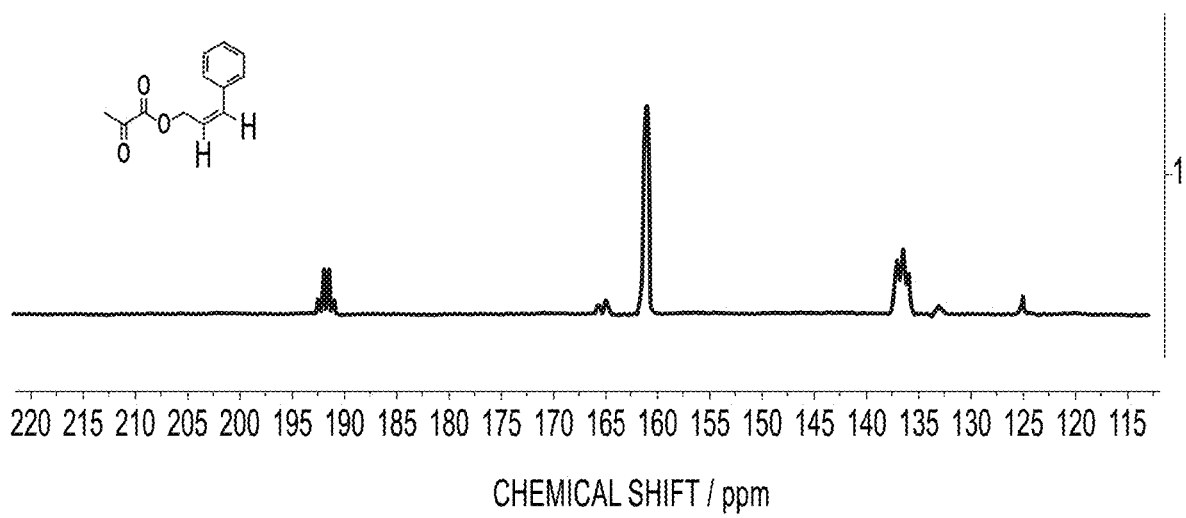
FIG. 20A shows an exemplary $^{13}$C NMR spectrum corresponding to 200 mM parahydrogenated 3-phenylprop-2-yn-1-yl 2-oxopropanoate (i.e., 3-phenylallyl 2-oxopropanoate with two H*), in accordance with various embodiments.

FIG. 20A shows an exemplary $^{13}$C NMR (101 MHz, CDCl$_3$) spectrum corresponding to 200 mM parahydrogenated 3-phenylprop-2-yn-1-yl 2-oxopropanoate (i.e., 3-phenylallyl 2-oxopropanoate with two H*) in acetone-d$_6$. The parahydrogenated 3-phenylprop-2-yn-1-yl 2-oxopropanoate was formed using the procedure described herein with respect to FIG. 18A. In the example shown, the parahydrogenated 3-phenylprop-2-yn-1-yl 2-oxopropanoate was determined to have a $^{13}$C polarization of about 13.9%.

Figure 20B:
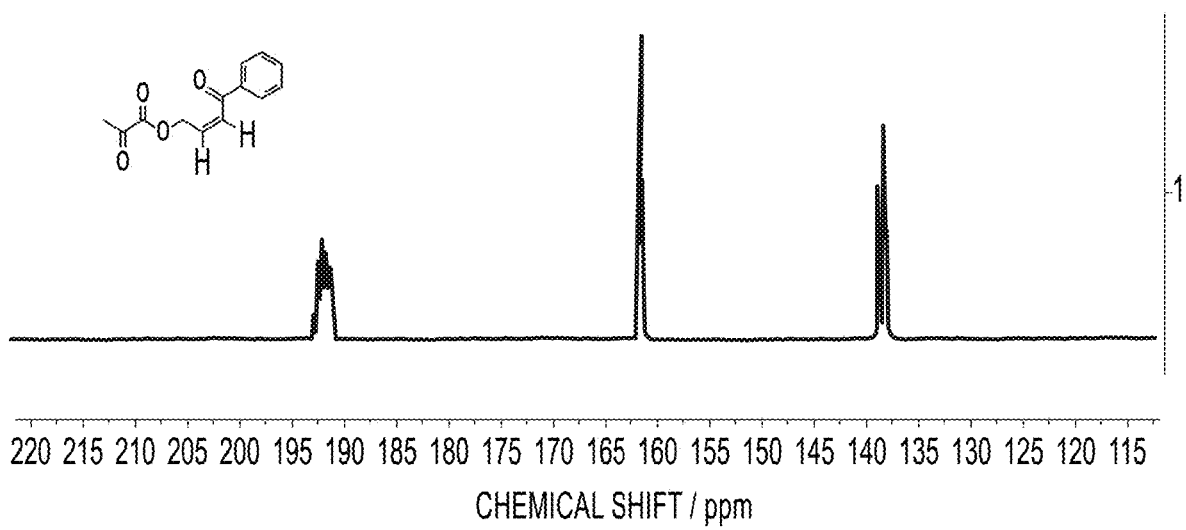
FIG. 20B shows an exemplary $^{13}$C NMR spectrum corresponding to 200 mM parahydrogenated 4-oxo-4-phenylbut-2-yn-1-yl 2-oxopropanoate (i.e., 4-oxo-4-phenylbut-2-en-1-yl 2-oxopropanoate with two H*), in accordance with various embodiments.

FIG. 20B shows an exemplary $^{13}$C NMR (101 MHz, CDCl$_3$) spectrum corresponding to 200 mM parahydrogenated 4-oxo-4-phenylbut-2-yn-1-yl 2-oxopropanoate (i.e., 4-oxo-4-phenylbut-2-en-1-yl 2-oxopropanoate with two H*). The parahydrogenated 4-oxo-4-phenylbut-2-yn-1-yl 2-oxopropanoate was formed using the procedure described herein with respect to FIG. 18B. In the example shown, the parahydrogenated 4-oxo-4-phenylbut-2-yn-1-yl 2-oxopropanoate was determined to have a $^{13}$C polarization of about 10.3%.

Figure 21:
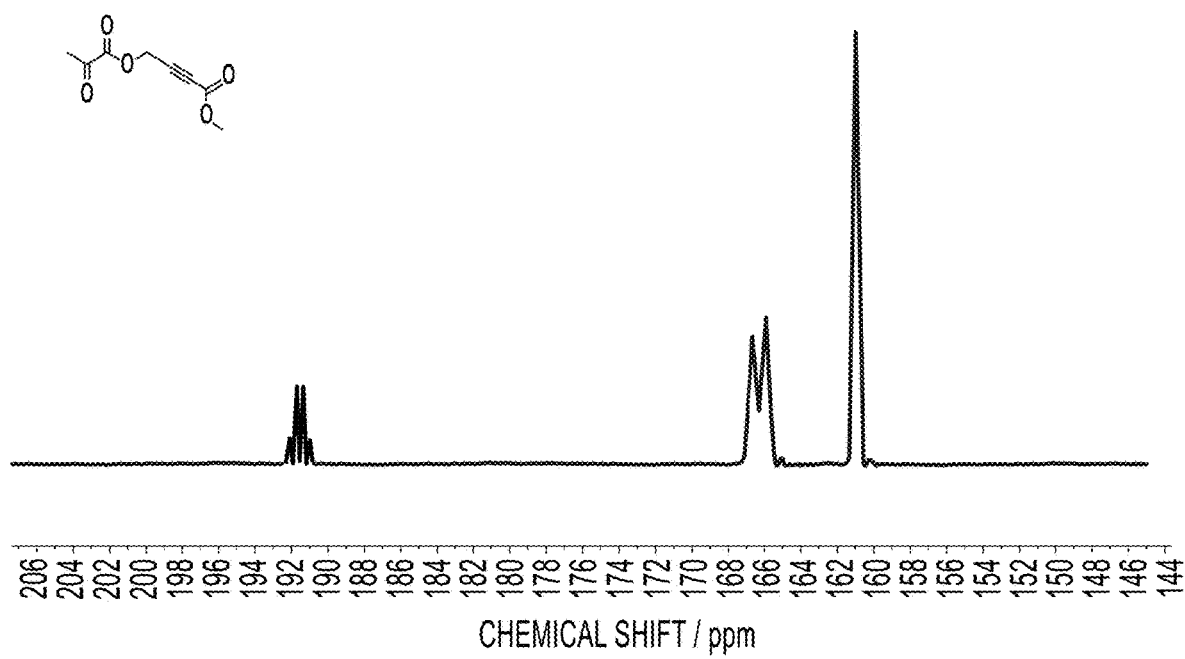
FIG. 21 shows an exemplary $^{13}$C NMR spectrum corresponding to 133 mM parahydrogenated methyl 4-((2-oxopropanoyl)oxy)but-2-ynoate (i.e., methyl 4-((2-oxopropanoyl)oxy)but-2-enoate with two H*), in accordance with various embodiments.

FIG. 21 shows an exemplary $^{13}$C NMR (101 MHz, CDCl$_3$) spectrum corresponding to 133 mM parahydrogenated methyl 4-((2-oxopropanoyl)oxy)but-2-ynoate (i.e., methyl 4-((2-oxopropanoyl)oxy)but-2-enoate with two H*). A parahydrogenation reaction between this novel molecule and parahydrogen was conducted in the presence of 1 mol % [Rh(dppb)(COD)]BF$_4$ at 60° C. with a parahydrogen pressure of 10 bars for 10 seconds. The reaction formed methyl 4-((2-oxopropanoyl)oxy)but-2-enoate with two H*, where the * symbol indicates a molecule containing protons derived from parahydrogen. In the example shown, the parahydrogenated methyl 4-((2-oxopropanoyl)oxy)but-2-ynoate was determined to have a $^{13}$C polarization of about 17.2%.

Example 18—Hyperpolarized Alpha-Ketoglutarate

Figure 22A:
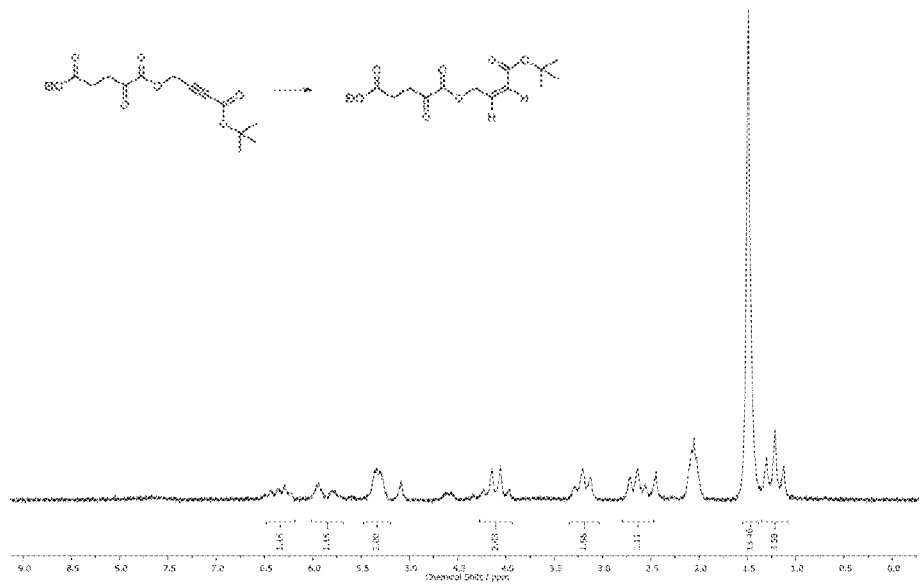
FIG. 22A shows an exemplary $^1$H NMR spectrum corresponding to parahydrogenated 1-(4-(tert-butoxy)-4-oxobut-2-yn-1-yl) 5-ethyl 2-oxopentanedioate (i.e., 1-(4-(tert-butoxy)-4-oxobut-2-en-1-yl) 5-ethyl 2-oxopentanedioate with two H*), in accordance with various embodiments.

FIG. 22A shows an exemplary $^1$H NMR (400 MHz, CDCl$_3$) spectrum corresponding to parahydrogenated 1-(4-(tert-butoxy)-4-oxobut-2-yn-1-yl) 5-ethyl 2-oxopentanedioate (i.e., 1-(4-(tert-butoxy)-4-oxobut-2-en-1-yl) 5-ethyl 2-oxopentanedioate with two H*). A parahydrogenation reaction between 1-(4-(tert-butoxy)-4-oxobut-2-yn-1-yl) 5-ethyl 2-oxopentanedioate and parahydrogen was conducted in the presence of 1 mol % [Rh(dppb)(COD)]BF$_4$ at 60° C. with a parahydrogen pressure of 10 bars for 10 seconds. The reaction formed 1-(4-(tert-butoxy)-4-oxobut-2-en-1-yl) 5-ethyl 2-oxopentanedioate with two H*, where the * symbol indicates a molecule containing protons derived from parahydrogen. In the example shown, the NMR signals marked with a * symbol correspond to the parahydrogen molecules added across the carbon-carbon triple bond of 1-(4-(tert-butoxy)-4-oxobut-2-yn-1-yl) 5-ethyl 2-oxopentanedioate.

Figure 22B:
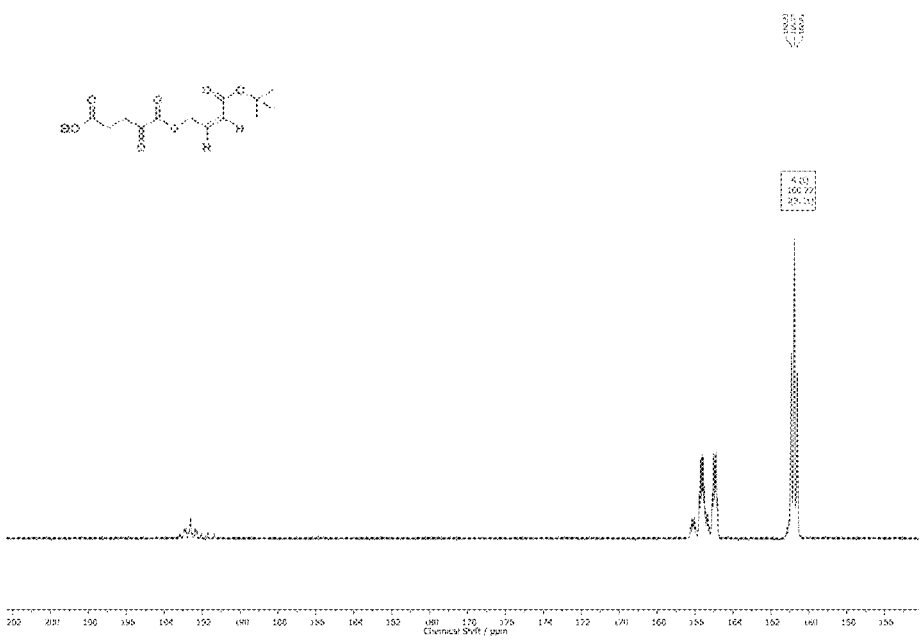
FIG. 22B shows an exemplary $^{13}$C NMR spectrum corresponding to 70 mM parahydrogenated 1-(4-(tert-butoxy)-4-oxobut-2-yn-1-yl) 5-ethyl 2-oxopentanedioate (i.e., 1-(4-(tert-butoxy)-4-oxobut-2-en-1-yl) 5-ethyl 2-oxopentanedioate with two H*), in accordance with various embodiments.

FIG. 22B shows an exemplary $^{13}$C NMR (101 MHz, CDCl$_3$) spectrum corresponding to 70 mM parahydrogenated 1-(4-(tert-butoxy)-4-oxobut-2-yn-1-yl) 5-ethyl 2-oxopentanedioate (i.e., 1-(4-(tert-butoxy)-4-oxobut-2-en-1-yl) 5-ethyl 2-oxopentanedioate with two H*) in acetone-d6. The parahydrogenated 1-(4-(tert-butoxy)-4-oxobut-2-yn-1-yl) 5-ethyl 2-oxopentanedioate was formed using the procedure described herein with respect to FIG. 22A. In the example shown, the parahydrogenated 1-(4-(tert-butoxy)-4-oxobut-2-yn-1-yl) 5-ethyl 2-oxopentanedioate was determined to have a $^{13}$C polarization of about 12.8%.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

The embodiments may further be described using the following clauses:

Other embodiments will be apparent from consideration of the specification and practice of the embodiments disclosed herein. It is intended that the specification and examples be considered as an example only, with a true scope and spirit of the disclosed embodiments being indicated by the following claims.

What is claimed is:

1. A composition comprising a compound of Formula (I):

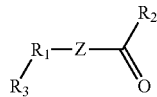

(I)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—);

$R_1$ comprises a parahydrogen induced polarization (PHIP) transfer moiety;

$R_2$ comprises an optionally substituted hydrocarbon, alkoxy group, primary amine, secondary amine, or tertiary amine; and $R_3$ comprises a biorelevant imaging agent comprising a non-hydrogen nuclear spin and is at least partially isotopically labeled with the non-hydrogen nuclear spin;

wherein the PHIP transfer moiety comprises *$CH_2$, *$CH_2$—*$CH_2$, *CHY, *C=Y, *$CR_4R_5$, *$CR_4Y$, *C=Y, *$CR_6R_7$—* $CR_8R_9$, or any deuterated version thereof, wherein:

*C is a $^{12}$C or $^{13}$C carbon isotope;

$R_4$ and $R_5$ are each independently selected from: hydrogen, $^1$H, $^2$H, $^3$H, a linear, branched, or cyclic C1-C10 alkyl hydrocarbon, a C6 aryl, a benzyl, a phenyl, a heteroaryl, and a haloalkyl group;

Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom selected from the group consisting of N, O, S, optionally substituted with a linear, branched, or cyclic C1-C10 alkyl hydrocarbon, a C6 aryl, benzyl, phenyl, heteroaryl, halogen or haloalkyl group; and $R_6$, $R_7$, $R_8$, and $R_9$ are each independently selected from: $^1$H, $^2$H, $^3$H, a linear, branched, or cyclic C1-C10 alkyl hydrocarbon, a C6 aryl, a benzyl, a phenyl, a heteroaryl, and a haloalkyl group.

2. A composition comprising a compound of Formula (I):

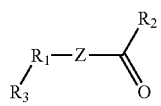

(I)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—);

$R_1$ comprises a parahydrogen induced polarization (PHIP) transfer moiety;

$R_2$ comprises an optionally substituted hydrocarbon, alkoxy group, primary amine, secondary amine, or tertiary amine; and $R_3$ comprises a biorelevant imaging agent comprising a non-hydrogen nuclear spin and is at least partially isotopically labeled with the non-hydrogen nuclear spin;

wherein: the PHIP transfer moiety includes at least one atom having a J-coupling with the non-hydrogen nuclear spin of at least 0.1 Hertz (Hz), or Z includes at least one atom having a J-coupling with the non-hydrogen nuclear spin of at least 0.1 Hertz (Hz).

3. A composition comprising a compound of Formula (I):

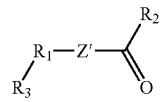

(II)

wherein Z comprises: (i) a carbon-carbon double bond (—C=C—) which is substituted to include $^1$H (proton), $^2$H (deuterium), or a combination thereof, or (ii) a carbon-carbon triple bond (—C≡C—);

$R_1$ comprises a parahydrogen induced polarization (PHIP) transfer moiety;

$R_2$ comprises an optionally substituted hydrocarbon, alkoxy group, primary amine, secondary amine, or tertiary amine; and $R_3$ comprises a biorelevant imaging agent comprising a non-hydrogen nuclear spin and is at least partially isotopically labeled with the non-hydrogen nuclear spin;

wherein the biorelevant imaging agent comprises a compound of the formula $R_4C(=O)X—$; wherein $R_4$ is chosen from a linear, branched, or cyclic C1-C10 alkyl group, in which one or more C atoms are optionally replaced with C=C, CO, COH, $CNH_2$, COOH, $CH_2COOH$, $CONH_2$, OC(=O); and X is chosen from $NR_5$, S and O; wherein $R_5$ is selected from hydrogen and an amino protecting group, optionally selected from trifluoroacetyl, acetyl, benzoyl, carbobenzoxy, tert-butyl carbonate and benzyl.

4. The composition of claim 1, wherein the PHIP transfer moiety includes at least one atom having a J-coupling with the non-hydrogen nuclear spin of at least 0.1 Hertz (Hz), or Z includes at least one atom having a J-coupling with the non-hydrogen nuclear spin of at least 0.1 Hertz (Hz).

5. The composition of claim 1, wherein $R_2$ is selected from: a methyl group, an ethyl group, a propyl group, an isopropyl group, an n-butyl group, an s-butyl group, a t-butyl group, an isobutyl group, a hydroxy group, a methyl alcohol group, an ethyl alcohol group, an n-propanol group, an isopropyl alcohol group, a propionic alcohol group, an n-butyl alcohol group, an s-butyl alcohol group, a t-butyl alcohol group, an isobutyl alcohol group, a methoxy group, an ethoxy group, a propoxy group, an isopropxy group, a propionic group, a butoxy group, a t-butoxy group, a s-butoxy group, an ester group, a phenyl group, a substituted phenyl group, a primary amine group, a secondary amine group, a tertiary amine group, a primary amide group, a secondary amide group, and a tertiary amide group.

6. The composition of claim 1, wherein the biorelevant imaging agent comprises a compound of the formula $R_{10}C(=O)X—$; wherein $R_{10}$ is chosen from a linear, branched, or cyclic C1-C10 alkyl group, in which one or more C atoms are optionally replaced with C=C, CO, COH, $CNH_2$, COOH, $CH_2COOH$, $CONH_2$, OC(=O); and X is chosen from $NR_{11}$, S and O; wherein $R_{11}$ is selected from hydrogen and an amino protecting group, optionally selected from trifluoroacetyl, acetyl, benzoyl, carbobenzoxy, tert-butyl carbonate and benzyl.

7. The composition of claim 1, wherein the biorelevant imaging agent is selected from: pyruvate, glutamate, glutamine, lactate, acetate, acetoacetate, zymonate, alanine, fructose, fumarate, bicarbonate, urea, dehydroascorbate, alpha-ketoglutarate, dihydroxyacetone, glucose, ascorbate, and conjugate acids thereof.

8. The composition of claim 1, wherein the composition has a solubility in water of less than 50 millimolar (mM).

9. The composition of claim 1, wherein the composition has a solubility in an organic solvent of less than 50 millimolar (mM); and wherein the organic solvent is acetone, ethanol, chloroform, or toluene.

10. The composition of claim 1, wherein reacting the composition with parahydrogen results in a chemical yield of parahydrogenated product of at least 30%.

11. The composition of claim 2, wherein the PHIP transfer moiety comprises an optionally substituted C1 hydrocarbon or an optionally substituted C2 hydrocarbon.

12. The composition of claim 2, wherein the PHIP transfer moiety comprises *$CH_2$, *$CH_2$—* $CH_2$, *CHY, *C=Y, *$CR_4R_5$, *$CR_4Y$, *C=Y, *$CR_6R_7$—* $CR_8R_9$, or any deuterated version thereof, wherein:
- *C is a $^{12}C$ or $^{13}C$ carbon isotope;
- $R_4$ and $R_5$ are each independently selected from: hydrogen, $^1H$, $^2H$, $^3H$, a linear, branched, or cyclic C1-C10 alkyl hydrocarbon, a C6 aryl, a benzyl, a phenyl, a heteroaryl, and a haloalkyl group;
- Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom selected from the group consisting of N, O, S, optionally substituted with a linear, branched, or cyclic C1-C10 alkyl hydrocarbon, a C6 aryl, benzyl, phenyl, heteroaryl, halogen or haloalkyl group; and
- $R_6$, $R_7$, $R_8$, and $R_9$ are each independently selected from: $^1H$, $^2H$, $^3H$, a linear, branched, or cyclic C1-C10 alkyl hydrocarbon, a C6 aryl, a benzyl, a phenyl, a heteroaryl, and a haloalkyl group.

13. The composition of claim 2, wherein $R_2$ is selected from: a methyl group, an ethyl group, a propyl group, an isopropyl group, an n-butyl group, an s-butyl group, a t-butyl group, an isobutyl group, a hydroxy group, a methyl alcohol group, an ethyl alcohol group, an n-propanol group, an isopropyl alcohol group, a propionic alcohol group, an n-butyl alcohol group, an s-butyl alcohol group, a t-butyl alcohol group, an isobutyl alcohol group, a methoxy group, an ethoxy group, a propoxy group, an isopropxy group, a propionic group, a butoxy group, a t-butoxy group, a s-butoxy group, an ester group, a phenyl group, a substituted phenyl group, a primary amine group, a secondary amine group, a tertiary amine group, a primary amide group, a secondary amide group, and a tertiary amide group.

14. The composition of claim 2, wherein the biorelevant imaging agent comprises a compound of the formula $R_{10}C(=O)X$—; wherein $R_{10}$ is chosen from a linear, branched, or cyclic C1-C10 alkyl group, in which one or more C atoms are optionally replaced with C=C, CO, COH, $CNH_2$, COOH, $CH_2COOH$, $CONH_2$, OC(=O); and X is chosen from $NR_{11}$, S and O; wherein $R_{11}$ is selected from hydrogen and an amino protecting group, optionally selected from trifluoroacetyl, acetyl, benzoyl, carbobenzoxy, tert-butyl carbonate and benzyl.

15. The composition of claim 2, wherein the biorelevant imaging agent is selected from: pyruvate, glutamate, glutamine, lactate, acetate, acetoacetate, zymonate, alanine, fructose, fumarate, bicarbonate, urea, dehydroascorbate, alpha-ketoglutarate, dihydroxyacetone, glucose, ascorbate, and conjugate acids thereof.

16. The composition of claim 2, wherein the composition has a solubility in water of less than 50 millimolar (mM).

17. The composition of claim 2, wherein the composition has a solubility in an organic solvent of less than 50 millimolar (mM); and wherein the organic solvent is acetone, ethanol, chloroform, or toluene.

18. The composition of claim 2, wherein reacting the composition with parahydrogen results in a chemical yield of parahydrogenated product of at least 30%.

19. The composition of claim 3, wherein the PHIP transfer moiety comprises an optionally substituted C1 hydrocarbon or an optionally substituted C2 hydrocarbon.

20. The composition of claim 3, wherein the PHIP transfer moiety comprises *$CH_2$, *$CH_2$—* $CH_2$, *CHY, *C=Y, *$CR_6R_7$, *$CR_6Y$, *C=Y, *$CR_8R_9$—* $CR_{10}R_{11}$, or any deuterated version thereof, wherein:
- *C is a $^{12}C$ or $^{13}C$ carbon isotope;
- $R_6$ and $R_7$ are each independently selected from: hydrogen, $^1H$, $^2H$, $^3H$, a linear, branched, or cyclic C1-C10 alkyl hydrocarbon, a C6 aryl, a benzyl, a phenyl, a heteroaryl, and a haloalkyl group;
- Y is selected from: a spin-1/2 atom, and a spin-1/2 atom covalently bonded to one or more chemical moiety chosen from: a linear, branched, or cyclic C1-C10 alkyl hydrocarbon, a C6 aryl, benzyl, phenyl, heteroaryl, halogen or haloalkyl group, or a heteroatom selected from the group consisting of N, O, S, optionally substituted with a linear, branched, or cyclic C1-C10 alkyl hydrocarbon, a C6 aryl, benzyl, phenyl, heteroaryl, halogen or haloalkyl group; and
- $R_8$, $R_9$, $R_{10}$, and $R_{11}$ are each independently selected from: $^1H$, $^2H$, $^3H$, a linear, branched, or cyclic C1-C10 alkyl hydrocarbon, a C6 aryl, a benzyl, a phenyl, a heteroaryl, and a haloalkyl group.

21. The composition of claim 3, wherein the PHIP transfer moiety includes at least one atom having a J-coupling with the non-hydrogen nuclear spin of at least 0.1 Hertz (Hz), or Z includes at least one atom having a J-coupling with the non-hydrogen nuclear spin of at least 0.1 Hertz (Hz).

22. The composition of claim 3, wherein $R_2$ is selected from: a methyl group, an ethyl group, a propyl group, an isopropyl group, an n-butyl group, an s-butyl group, a t-butyl group, an isobutyl group, a hydroxy group, a methyl alcohol group, an ethyl alcohol group, an n-propanol group, an isopropyl alcohol group, a propionic alcohol group, an n-butyl alcohol group, an s-butyl alcohol group, a t-butyl alcohol group, an isobutyl alcohol group, a methoxy group, an ethoxy group, a propoxy group, an isopropxy group, a propionic group, a butoxy group, a t-butoxy group, a s-butoxy group, an ester group, a phenyl group, a substituted phenyl group, a primary amine group, a secondary amine group, a tertiary amine group, a primary amide group, a secondary amide group, and a tertiary amide group.

23. The composition of claim 3, wherein the biorelevant imaging agent is selected from: pyruvate, glutamate, glutamine, lactate, acetate, acetoacetate, zymonate, alanine, fructose, fumarate, bicarbonate, urea, dehydroascorbate, alpha-ketoglutarate, dihydroxyacetone, glucose, ascorbate, and conjugate acids thereof.

24. The composition of claim 3, wherein the composition has a solubility in water of less than 50 millimolar (mM).

25. The composition of claim 3, wherein the composition has a solubility in an organic solvent of less than 50 millimolar (mM); and wherein the organic solvent is acetone, ethanol, chloroform, or toluene.

26. The composition of claim 3, wherein reacting the composition with parahydrogen results in a chemical yield of parahydrogenated product of at least 30%.

* * * * *